US012576042B2

(12) United States Patent
Lipton

(10) Patent No.: US 12,576,042 B2
(45) Date of Patent: Mar. 17, 2026

(54) METHODS AND COMPOSITIONS FOR TREATING NEUROLOGICAL CONDITIONS

(71) Applicant: Stuart A. Lipton, Rancho Santa Fe, CA (US)

(72) Inventor: Stuart A. Lipton, Rancho Santa Fe, CA (US)

( * ) Notice: Subject to any disclaimer, the term of this patent is extended or adjusted under 35 U.S.C. 154(b) by 85 days.

(21) Appl. No.: 18/061,081

(22) Filed: Dec. 2, 2022

(65) Prior Publication Data

US 2023/0346713 A1 Nov. 2, 2023

Related U.S. Application Data

(63) Continuation of application No. 16/635,212, filed as application No. PCT/US2018/044608 on Jul. 31, 2018, now Pat. No. 11,529,319.

(60) Provisional application No. 62/539,549, filed on Aug. 1, 2017.

(51) Int. Cl.

| | |
|---|---|
| ***A61K 31/04*** | (2006.01) |
| ***A61K 31/551*** | (2006.01) |
| ***A61P 25/00*** | (2006.01) |
| ***A61P 25/18*** | (2006.01) |
| ***C12Q 1/6883*** | (2018.01) |

(52) U.S. Cl.

CPC ............ *A61K 31/04* (2013.01); *C12Q 1/6883* (2013.01); *A61K 31/551* (2013.01); *A61P 25/00* (2018.01); *A61P 25/18* (2018.01); *C12Q 2600/106* (2013.01); *C12Q 2600/158* (2013.01)

(58) Field of Classification Search

CPC ................................ A61K 31/04; A61P 25/00

See application file for complete search history.

(56) References Cited

U.S. PATENT DOCUMENTS

| | | | |
|---|---|---|---|
| 4,994,467 | A | 2/1991 | Zimmerman |
| 8,461,148 | B2 | 6/2013 | Hollander |
| 10,555,916 | B2 | 2/2020 | Katz |
| 11,529,319 | B2 | 12/2022 | Lipton |
| 2010/0137448 | A1 | 6/2010 | Lipton et al. |
| 2011/0171291 | A1 | 7/2011 | Lipton |
| 2014/0088083 | A1 | 3/2014 | Hollander |
| 2015/0359759 | A1 | 12/2015 | Katz |

FOREIGN PATENT DOCUMENTS

| | | | |
|---|---|---|---|
| EP | 1852113 | A2 | 11/2007 |
| KR | 2007-0046185 | A | 5/2007 |
| WO | WO-01/62706 | A1 | 8/2001 |
| WO | WO-2006/034187 | A2 | 3/2006 |
| WO | WO-2006/034465 | A1 | 3/2006 |
| WO | WO-2014/015047 | A1 | 1/2014 |
| WO | WO-2015/004371 | A1 | 1/2015 |

OTHER PUBLICATIONS

Han et al., "NMDA receptor antagonist MK-801 reduces neuronal damage and preserves learning and memory in a rat model of traumatic brain injury", Neuroscience Bulletin, vol. 25, No. 6, pp. 367-375 (2009).*

Chez et al., "Memantine experience in children and adolescents with autistic spectrum disorders," Annals of Neurology 56(Suppl. 8):S109, Abstract C-10 (2004).

Erickson et al., "A retrospective study of memantine in children and adolescents with pervasive developmental disorders," Psychopharmacology (Berl). 191(1):141-7 (2007).

Extended European Search Report for European Application No. 18841846.1, dated Mar. 15, 2021 (13 pages).

International Preliminary Report on Patentability for International Application No. PCT/US2018/044608, mailed Feb. 4, 2020 (7 pages).

International Search Report for International Application No. PCT/US18/44608, mailed Dec. 3, 2018 (4 pages).

Jin et al., "A promising dual-functional neuroprotective derivative of memantine," J Pharm Biomed Sci. 6(6):392-8 (Jun. 2016).

Lipton, "Application of FDA-approved memantine and newer nitromemantine derivatives to treat neurological manifestations in rodent models of tuberous sclerosis complex," CDRMP Research award, Jun. 2015, available <https://apps.dtic.mil/sti/pdfs/ADA621184.pdf> (9 pages).

Lipton, "Application of FDA-approved memantine and newer nitromemantine derivatives to treat neurological manifestations in rodent models of tuberous sclerosis complex," CDRMP Research award, May 2014, available <https://apps.dtic.mil/dtic/tr/fulltext/u2/a604193.pdf> (7 pages).

Takahashi et al., "Pharmacologically targeted NMDA receptor antagonism by NitroMemantine for cerebrovascular disease," Sci Rep. 5:14781 (Oct. 19, 2015) (15 pages).

Tu et al., "NitroSynapsin therapy for a mouse MEF2C haploinsufficiency model of human autism," Nat Commun. 8(1):1-12 (2017).

Written Opinion for International Application No. PCT/US18/44608, mailed Dec. 3, 2018 (6 pages).

Zweier et al., "Mutations in MEF2C from the 5q14.3q15 microdeletion syndrome region are a frequent cause of severe mental retardation and diminish MECP2 and CDKL5 expression," Hum Mutat. 31(6):722-33 (2010).

Trudler et al., "Dysregulation of miRNA expression and excitation in MEF2C autism patient hiPSC-neurons and cerebral organoids", Molecular Psychiatry 30:1479-1496 (Sep. 2024) (18 pages).

Olney et al., "Pathological Changes Induced in Cerebrocortical Neurons by Phencyclidine and Related Drugs", Science, 224(4910);1360-1362 (Jun. 1986) (1 page) (Abstract).

(Continued)

*Primary Examiner* — Kevin E Weddington

(74) *Attorney, Agent, or Firm* — Clark & Elbing LLP

(57) ABSTRACT

Disclosed herein are methods for treating juvenile onset neurological conditions, such as autism (ASD), intellectual disability, or epilepsy, with an inhibitor of N-methyl-D-aspartate receptor (NMDAR). The inhibitor may be NitroSynapsin or a derivative thereof.

2 Claims, 48 Drawing Sheets

(56) References Cited

OTHER PUBLICATIONS

Ellison, "The N-methyl-D-aspartate antagonists phencyclidine, ketamine, and dizocilpine as both behavioral and anatomical models of the dementias", Brain Research Reviews 20(2):250-267 (Feb. 1995) (2 pages) (Abstract).

* cited by examiner

| Dysregulated biogroups in *Mef2c*-het mice | # of genes dysregulated | Direction | Score | *P*-value | source |
|---|---|---|---|---|---|
| neurogenesis | 33 | Down | 34.31 | 1.3E-15 | GO |
| neuron differentiation | 23 | Down | 27.51 | 1.1E-12 | GO |
| synapse | 18 | Down | 24.04 | 3.6E-11 | GO |
| regulation of neuron death | 5 | Up | 9.29 | 9.3E-05 | GO |

METHODS AND COMPOSITIONS FOR TREATING NEUROLOGICAL CONDITIONS

CROSS-REFERENCE

This application claims the benefit of U.S. Provisional Patent Application No. 62/539,549, filed Aug. 1, 2017, which is incorporated herein by reference in its entirety.

BACKGROUND OF THE INVENTION

In the brain, myocyte enhancer factor 2 (MEF2) transcription is critical for neuronal differentiation, synaptic formation, and neuronal survival. It has been shown that conditional knockout of Mef2c in nestin-expressing neural progenitor cells produced mice with impaired electrophysiological network properties and behavioral deficits reminiscent of Rett syndrome, a neurological disorder related to ASD. Regions of chromosome 5q14.3q15 microdeletions cause neurological deficit phenotypes in children identified as MEF2C haploinsufficiency. These patients exhibit signs and symptoms that include ASD, intellectual and developmental disability (IDD), poor reciprocal behavior, lack of speech, stereotyped and repetitive behavior, and epilepsy. The disorders caused by MEF2C haploinsufficiency have been collectively termed MEF2C haploinsufficiency syndrome (MCHS). Additionally, multiple MEF2 target genes have been identified as autism-related genes in human pedigrees with shared ancestry.

SUMMARY OF THE INVENTION

Disclosed herein, in some aspects, are methods of treating a juvenile-onset neurological condition in a subject in need thereof with an inhibitor of N-methyl-D-aspartate type of glutamate receptor (NMDAR). In some instances, the inhibitor of NMDAR comprises NitroSynapsin. In some instances, the inhibitor of NMDAR is NitroSynapsin. In some instances, the inhibitor of NMDAR is a compound of Formula I, or a pharmaceutically acceptable salt thereof:

Formula I

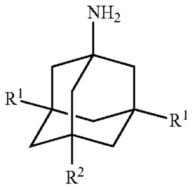

wherein each $R^1$ is independently selected from $—CH_3$ and $—CH_2CH_3$; and $R^2$ is selected from hydrogen and $—ONO_2$.

In some instances, each $R^1$ is $—CH_2CH_3$ and $R^2$ is $—ONO_2$. In some instances, the inhibitor of NMDAR is a compound of Formula II, or a pharmaceutically acceptable salt thereof:

Formula II

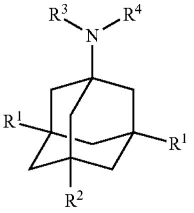

wherein each $R^1$ is independently selected from hydrogen, $C_1$-$C_6$ alkyl, cycloalkyl, heterocycloalkyl, aryl, and heteroaryl;

$R^2$ is selected from hydrogen, $C_1$-$C_6$ alkyl, and $—ONO_2$;

$R^3$ and $R^4$ are each independently selected from hydrogen and $C_1$-$C_6$ alkyl;

or $R^3$ and $R^4$ are taken together with the nitrogen atom to which they are attached to form a heterocycloalkyl.

In some instances, $R^3$ and $R^4$ are each hydrogen. In some instances, $R^2$ is selected from hydrogen and $—ONO_2$. In some instances, $R^2$ is $—ONO_2$. In some instances, each $R^1$ is independently $C_1$-$C_6$ alkyl. In some instances, each $R^1$ is independently selected from methyl and ethyl. In some instances, each $R^1$ is ethyl. In some instances, the juvenile-onset neurological condition is an Intellectual and Developmental Disability. In some instances, the juvenile-onset neurological condition is an Autism Spectrum Disorder (ASD). In some instances, the juvenile-onset neurological condition comprises epilepsy. In some instances, the juvenile-onset neurological condition is tuberous sclerosis. In some instances, the juvenile-onset neurological condition is autism. In some instances, the juvenile-onset neurological condition is Rett syndrome. In some instances, the subject is a child. In some instances, the subject is MEF2C haploinsufficient, and has MEF2C haploinsufficiency syndrome (MCHS). In some instances, selecting the subject for treatment based on an expression level of at least one gene selected from MEF2C, SLC32A1, SLC17A6, SYP, and GAD65. In some instances, the expression level is that of a cell of the subject. In some instances, the expression level is that of a cell in the brain of the subject. In some instances, the expression level is that of a circulating cell of the subject. In some instances, the expression level is an mRNA expression level. In some instances, the expression level is a protein expression level. In some instances, the subject has a MEF2C haploinsufficiency. In some instances, the gene is SLC32A1 and the expression level is significantly reduced relative to that of the average subject comprising two copies of the MEF2C gene. In some instances, the gene is SLC17A6 and the expression level is significantly increased relative to that of the average subject comprising two copies of the MEF2C gene. In some instances, the gene is SYP and the expression level is significantly reduced relative to that of the average subject comprising two copies of the MEF2C gene. In some instances, the gene is GAD65 and the expression level is significantly reduced relative to that of the average subject comprising two copies of the MEF2C gene.

BRIEF DESCRIPTION OF THE DRAWINGS

FIG. 3 shows Mef2c-het mice displayed MCHS-like phenotypes.

FIG. 4 shows downregulation of neurogenic and synaptic genes in Mef2c-het mice by microarray analysis. In FIG. 4 and subsequent FIGS. 5-19 that refer to color, the color images appear in our publication: Tu S, Lipton S A, Nakanishi N, et al. NitroSynapsin therapy for the mouse MEF2C haploinsufficiency model of human autism. *Nature Commun* 8, 1488 (2017)].

FIG. 6 shows Mef2c-het mice exhibited abnormal adult neurogenesis.

FIG. 7 shows Mef2c-het mice exhibited altered synaptic properties and excitatory/inhibitory (E/I) imbalance in synaptic neurotransmission.

FIG. 8 shows Mef2c-het mice expressed altered levels of synaptic proteins in the hippocampus.

FIG. 9 shows Mef2c-het mice exhibited impairment of hippocampal long-term potentiation (LTP) and paired-pulse facilitation (PPF) in brain slice recordings.

FIG. 10 shows NitroSynapsin rescued MCHS-like phenotypes in Mef2c-het mice. FIG. 10E shows Representative traces of mouse movement in the three-chamber social ability test. FIGS. 10G-I show Mef2c-het mice (Het/V) exhibit abnormalities in social interaction measured by time spent in each chamber (FIG. 10G); and number of visits (FIG. 10H) and duration of visits (FIG. 10I) to E (empty) or S1 (stranger mouse 1) chambers. N treatment ameliorated this deficit (Het/N). M: Middle chamber. Data are mean±s.e.m. n=7-9 per group. *P<0.05, **P<0.01 by ANOVA.

FIG. 12 shows NitroSynapsin was more effective than memantine in rescuing neurological deficits of Mef2c-het mice.

FIG. 16 shows Mef2c-het mice showed increased caspase-3 activation and apoptosis in the hippocampus.

FIG. 17 shows NitroSynapsin normalized the number of astrocytes in Mef2c-het hippocampus. FIG. 17A). The number of GFAP+ cells was restored to WT levels by chronic treatment with NitroSynapsin (FIG. 17C). ML, molecular layer of the dentate gyms (DG). Scale bar, 25 μm.

FIG. 18 shows Mef2c-het mice displayed reduction in parvalbumin+(PV+) inhibitory synapses and cells.

FIG. 21 shows effects of Memantine (M) and NitroSynapsin (N, labeled Nitromemantine in figure) treatment on synaptic integrity of $Tsc2^{+/-}$ (het) mice.

FIG. 22 shows abnormal CA1-LTP in $Tsc2^{+/-}$ (het) mice and improvement with NitroSynapsin.

DETAILED DESCRIPTION OF THE INVENTION

Figure 1:
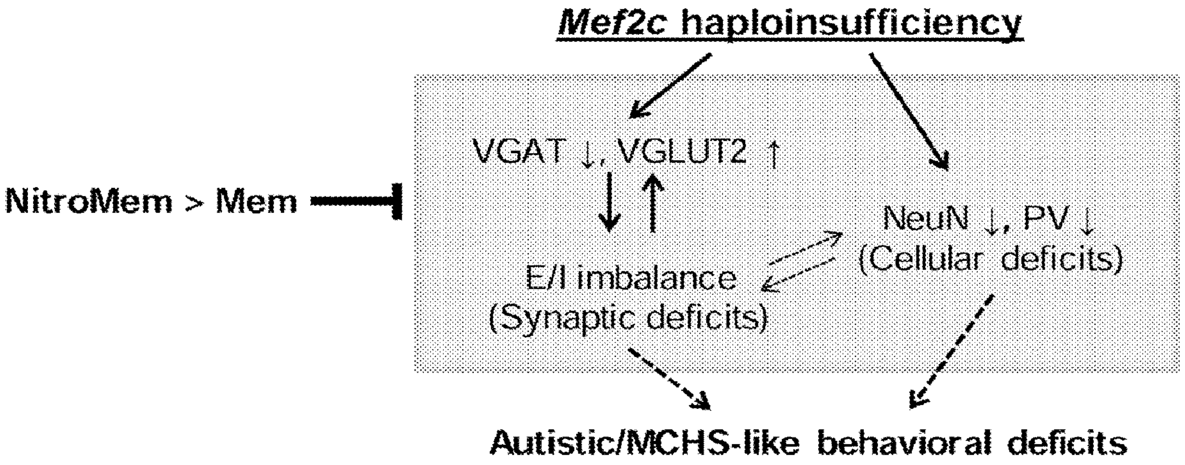
FIG. 1 shows a summary diagram of Mef2c haploinsufficiency leading to E/I imbalance and MCHS-like phenotypes that were rescued by NitroSynapsin (also known as NitroMemantine YQW-036 or NMI-6979).

In the brain, the transcription factor, myocyte enhancer factor 2 (MEF2), is critical for neuronal differentiation, synaptic formation, and neuronal survival. It has been shown that conditional knockout of Mef2c in nestin-expressing neural progenitor cells produced mice with impaired electrophysiological network properties and behavioral deficits reminiscent of Rett syndrome, a neurological disorder related to autism spectrum disorder (ASD). Regions of chromosome 5q14.3q15 microdeletions cause neurological deficit phenotypes in children identified as MEF2C haploinsufficiency. These patients exhibit signs and symptoms that include ASD, intellectual and developmental disability (IDD), poor reciprocal behavior, lack of speech, stereotyped and repetitive behavior, and epilepsy. The disorders caused by MEF2C haploinsufficiency have been collectively termed MEF2C haploinsufficiency syndrome (MCHS). Additionally, multiple MEF2 target genes have been identified as autism-related genes in human pedigrees with shared ancestry. Therefore, the claimed therapeutic method for MCHS finds utility in effectively treating other forms of ASD/IDD and epilepsy as well.

Improved therapies are needed for the treatment of ASD, IDD, epilepsy and related conditions. Along these lines, an improved series of drugs were recently synthesized based on dual memantine-like action and redox (S-nitrosylation)-based inhibition predominantly of extrasynaptic NMDA receptors (eNMDAR). Initially these compounds were called ‘NitroMemantines,’ but recently the lead compound, YQW-036 (or NMI-6979), was designated NitroSynapsin because of its ability to restore synaptic number and function in the face of multiple insults. Scheme 1 shows the structures of Memantine and NitroMemantine (aka NitroSynapsin).

Scheme 1.

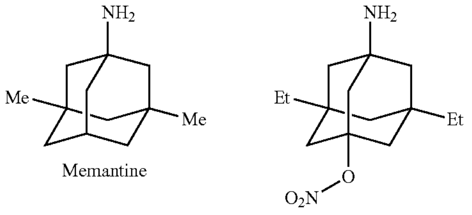

Memantine

NitroMemantine

As embodied in the Examples herein, neurobehavioral deficits, excitatory/inhibitory (E/I) imbalance, and histological damage were all ameliorated by treatment with NitroSynapsin (also known as NitroMemantine YQW-036/NMI-6979—see Structure 1) in $Mef2c^{+/-}$ (Mef2c-het) mice. Mef2c-het mice were developed as a model for the human MEF2C haploinsufficiency form of ASD. Mef2 c-het mice displayed neuronal and synaptic abnormalities, decreased inhibitory and increased excitatory synaptic transmission in the hippocampus, suppressed long-term potentiation (LTP), and MCHS-like behavioral phenotypes. Before treatment with NitroSynapsin, these mice exhibited decreased neurogenesis, enhanced neuronal apoptosis, an altered ratio of E/I neurotransmission, and a phenotype of behavioral deficits resembling those of human patients with Autism Spectrum Disorder (ASD), Intellectual and Developmental Disability (IDD) and epilepsy. Importantly, nearly all of these phenotypes were rescued or mitigated by chronic treatment with NitroSynapsin. Moreover, additional mouse models of the human diseases of Rett syndrome and Tuberous Sclerosis showed that NitroSynapsin was similarly effective in correcting phenotypes associated with these other forms of ASD/IDD and epilepsy that are associated with E/I imbalance. Mechanism notwithstanding, NitroSynapsin was shown as an effective treatment in multiple mouse models of ASD/IDD and epilepsy, and therefore should be effective for treatment of human ASD/IDD and epilepsy.

It was surprising to us that NitroSynapsin had efficacy for MCHS and other forms of ASD/IDD and epilepsy syndromes because other NMDAR antagonists, like memantine, had failed in human clinical trials for this purpose (Fung L K, Hardan A Y. Developing medications targeting glutamatergic dysfunction in autism: Progress to date. *CNS Drugs* 29, 453-463 (2015); Tu S, Lipton S A Nakanishi N, et al. NitroSynapsin therapy for the mouse MEF2C haploinsufficiency model of human autism. *Nature Commun* 8, 1488 (2017)). NitroSyanpsin works in this regard because it manifests superior efficacy while having clinically-tolerated properities of avoiding blockade of synaptic transmission and long term potentiation (LTP).

FIG. 1 shows a summary diagram of Mef2c haploinsufficiency leading to E/I imbalance and MCHS-like phenotypes that were rescued by NitroSynapsin. Mef2c haploinsufficiency leads to decreased VGAT and increased VGLUT2 protein levels, resulting in E/I imbalance (overexcitability) and synaptic dysfunction. Mef2c haploinsufficiency also causes neuronal loss, notably a reduced number of PV+ inhibitory interneurons. These synaptic and cellular abnormalities are likely the underlying cause of the MCHS-like behavioral phenotypes observed in Mef2c-het mice. The histological and behavioral phenotypes are ameliorated by chronic treatment with NitroSynapsin (NitroMem) to a significantly greater degree than the FDA-approved drug memantine (Mem).

Neurological Conditions

Provided herein, in some aspects, are methods of treating at least one neurological condition in a subject. Methods may comprise delivering a compound disclosed herein to the subject. Methods may comprise delivering a combination of compounds disclosed herein to the subject. The neurological condition may be associated with E/I imbalance, as those skilled in the art know how to assess. In brief, E/I can be assessed by a number of methods, for example, patch-clamp electrical recording to show hyperexcitability or deficits in inhibitory transmission (Tu et al., 2017 ibid.). Histological assessment of excitatory and inhibitory synapses as described in Tu et al., 2017 (ibid.) can also be used in part to assess E/I imbalance. Neurological conditions in humans or other animals that may be treated according to methods disclosed herein include, but are not limited to any form of autism (ASD), MEF2C haploinsufficiency syndrome (MCHS), Intellectual and Developmental Disabilities (IDD), epilepsy, Rett syndrome, and Tuberous Sclerosis.

Methods of treatment disclosed herein comprise treating a juvenile-onset neurological condition. A juvenile-onset neurological condition is one in which one or more neurological or behavioral abnormalities appear during childhood. In some instances, childhood is considered between the ages of 0 and 18 years of age. In some instances, the child is between 0 and 12 years of age. Non-limiting examples of neurological and behavioral abnormalities include hand clasping, lack of eye contact, slow head growth, seizures, repetitive motions, reduction or loss of language, hand-wringing, clapping, tapping, random grasping and releasing, breathing irregularities, reduction or loss of social interaction, reduction or loss of social interaction of communication skills, unsteady gait, apraxia, motor difficulties, muscle weakness, rigidity, spasticity, psychomotor delay, generalized hypotonia, poor eye contact, hand-mouth stereotypies, strabismus, and facial dimorphism s. Non-limiting examples of juvenil e-onset neurological conditions include Autism Spectrum Disorders (ASD), Intellectual and Developmental Disabilities (IDD), epilepsy, MEF2C haploinsufficiency syndrome (MCHS), and Tuberous Sclerosis. In some instances IDD comprises conditions that fall under ASD, including autism itself. Autism Spectrum Disorders include, but are not limited to autism, Asperger's Syndrome, and Rett Syndrome. Additional conditions that may be considered juvenile-onset neurological conditions include attention deficit disorder, attention deficit hyperactive disorder, pervasive developmental disorder, and obsessive compulsive disorder. In some instances, the juvenile-onset neurological condition is due to brain injury caused by disease/infection, head trauma, or toxicity.

Methods of treatment disclosed herein may result in restoring synaptic plasticity to improve E/I imbalance. Methods of treatment disclosed herein may result in preventing neuronal loss. Methods of treatment disclosed herein may result in an increase of synaptic markers. Methods of treatment disclosed herein may result in long-term potentiation (LTP). Methods of treatment disclosed herein may result in an increase of neuronal number. Methods of treatment disclosed herein may result in corrected E/I imbalance. Methods of treatment disclosed herein may result in improved autistic/MCHS-like behavioral deficits. Methods of treatment disclosed herein may result in increased inhibitory interneuron/parvalbumin (PV)+ synapses. Methods of treatment disclosed herein may result in normalizing VGAT and/or VGLUT2 levels. Methods of treatment disclosed herein may result in normalizing a ratio of VGLUT1 to VGAT, a ratio of VGLUT2 to VGAT, or the combination thereof. Methods of treatment disclosed herein may rescue apoptotic neurons. Methods of treatment disclosed herein may reduce the number of apoptotic neurons observed in the brain of the subject. Methods of treatment disclosed herein may result in reducing or preventing cognitive deficits. Methods of treatment disclosed herein may result in reducing or preventing repetitive behavior. Methods of treatment disclosed herein may result in reducing or preventing impaired social interactions. Methods of treatment disclosed herein may result in reducing or preventing anxiety. Methods of treatment disclosed herein may result in reducing or preventing aberrant motor behaviors. Methods of treatment disclosed herein may result in reducing or preventing hand clasping. Methods of treatment disclosed herein may result in reducing or preventing abnormal social behavior. Methods of treatment disclosed herein may improve memory. Methods of treatment disclosed herein may improve learning.

In some instances, methods disclosed herein comprise treating a subject with Autism Spectrum Disorder (ASD). Subjects who fall under ASD include subjects diagnosed with autism, Asperger syndrome, and pervasive developmental disorder not otherwise specified (PDD-NOS), and childhood disintegrative disorder. These subjects exhibit difficulty with social communication and interaction. They may also exhibit repetitive behaviors. Diagnosis of ASD may be performed based on criteria published in the most current Diagnostic and Statistical Manual of Mental Disorders and/or International Statistical Classification of Diseases and Related Health Problems (ICD). Practitioners may administer assessments such as the Autism Diagnostic Interview-Revised and the Autism Diagnostic Observation Schedule. Other conditions, such as epilepsy, tuberous sclerosis (non-malignant tumors), anxiety, depression, schizophrenia, attention deficit hyperactivity disorder (ADHD), and sensory processing disorder are often comorbid with ASD. Methods disclosed herein may comprise assessing the severity of ASD or a condition comorbid with ASD. Methods may comprise assessing the presence and/or severity of one or more symptoms of ASD or a condition comorbid with ASD before delivering a compound disclosed herein to the subject. Methods may comprise assessing the presence and/or severity of one or more symptoms of ASD or a condition comorbid with ASD after delivering a compound disclosed herein to the subject. Methods disclosed herein may result in reducing the severity of one or more symptoms of ASD or a condition comorbid with ASD. In some instances, methods comprise delivering a compound disclosed herein to a subject with ASD and providing a behavioral therapy to the subject, such as speech and language therapy and occupational therapy.

In some instances, methods disclosed herein comprise treating a subject with an Intellectual and Developmental Disability (IDD). An IDD is a condition that affects the subject's physical, cognitive, and/or emotional development. The subject with the IDD may have difficulty learning, reasoning, problem solving, and/or socializing. The subject with the IDD may exhibit one or more behavioral disorders, speech impediments, language issues, seizures, and physical disabilities. The subject with the IDD may have impaired vision. The subject with the IDD may have impaired hearing. The subject with the IDD may have a metabolic disorder. In some instances, these issues worsen with age. Examples of IDDs, or conditions associated with IDDs, include, but are not limited to, cerebral palsy, Down syndrome, Fragile X syndrome, autism spectrum disorders (ASDs), phenylketonuria (PKU) and congenital hypothyroidism. Methods disclosed herein may comprise assessing the severity of an IDD or a condition comorbid with IDD. Methods may comprise assessing the presence and/or severity of one or more symptoms of the IDD before delivering a compound disclosed herein to the subject. Methods may comprise assessing the presence and/or severity of one or more symptoms of the IDD after delivering a compound disclosed herein to the subject. Methods disclosed herein may result in reducing the severity of one or more symptoms of the IDD. In some instances, methods comprise delivering a compound disclosed herein to a subject and providing a behavioral therapy to the subject with the IDD, such as speech and language therapy and occupational therapy.

In some instances, methods disclosed herein comprise treating a subject with epilepsy. Epilepsy is a term to describe a variety of neurological disorders characterized by epileptic seizures. These seizures are believed to be caused by excessive and/or abnormal activity in the brain. In many cases, seizures can be controlled with medication, surgery, neurostimulation, dietary restriction, or a combination thereof. Methods may comprise delivering one or more compounds disclosed herein to a subject with epilepsy in combination with medication, surgery, neurostimulation, dietary restriction, or a combination thereof. Methods may comprise assessing the presence and/or severity of the subject's seizures before delivering a compound disclosed herein to the subject. Methods may comprise assessing the presence and/or severity of the subject's seizures after delivering a compound disclosed herein to the subject. Methods disclosed herein may result in reducing the severity of the subject's seizures. Methods disclosed herein may result in reducing the number of occurrences of the subject's seizures. Methods disclosed herein may result in reducing the frequency of the subject's seizures. Methods disclosed herein may result in reducing the duration of the subject's seizures.

In some instances, methods disclosed herein comprise treating a subject with Rett syndrome. Rett syndrome is a neurological disorder that is characterized by challenges with language and coordination, and repetitive movements. In some instances subjects with Rett syndrome have seizures, scoliosis, and sleeping problems. Other symptoms include decreased head growth (before age 4), reduction or loss of hand control, reduction or loss of language, hand-wringing, clapping, tapping, random grasping and releasing, breathing irregularities, reduction or loss of social interaction, reduction or loss of social interaction of communication skills, unsteady gait, apraxia, motor difficulties, muscle weakness, rigidity, and spasticity. Methods may comprise delivering one or more compounds disclosed herein to a subject with Rett syndrome in combination with medications used to treat Rett syndrome, including, but not limited to sleep aids, selective serotonin reuptake inhibitors, anti-psychotics, and beta-blockers, or a combination thereof. Methods may comprise assessing the presence and/or severity of the subject's symptoms before delivering a compound disclosed herein to the subject with Rett syndrome. Methods may comprise assessing the presence and/or severity of the subject's symptoms after delivering a compound disclosed herein to the subject with Rett syndrome. Methods disclosed herein may result in reducing the severity of one or more of the subject's with Rett syndrome symptoms. Methods disclosed herein may result in alleviating one or more of the subject's with Rett syndrome symptoms.

In some instances, methods disclosed herein comprise treating a subject with Tuberous Sclerosis. Tuberous sclerosis (TSC) is an autosomal dominant disorder caused by heterozygous mutations in the TSC1 or TSC2 gene. TSC is often associated with neurological, cognitive, and behavioral deficits. TSC patients may express co-morbidity with anxiety and mood disorders. TSC-related neurological symptoms may be accompanied by excessive glutamatergic activity and altered synaptic spine structures. Tuberous Sclerosis is a condition typically characterized by benign tumors. These tumors can appear in organs such as the brain, heart, kidney, liver, eye, lungs and skin. Symptoms include, but are not limited to signs of ASD, seizures, cognitive disabilities, behavioral abnormalities (e.g., aggression, attention deficit hyperactivity disorder, obsessive compulsive disorder, self-injury), skin conditions, lung disease and kidney disease. There are few treatment options for this condition, but Everolimus has been approved for treatment of tumors in the brain and kidneys. Methods may comprise delivering one or more compounds disclosed herein to a subject with Tuberous Sclerosis in combination with Everolimus, neurosurgical intervention, or a combination thereof. Methods may comprise assessing the presence and/or severity of the subject's symptoms before delivering a compound disclosed herein to the subject with Tuberous Sclerosis. Methods may comprise assessing the presence and/or severity of the subject's symptoms after delivering a compound disclosed herein to the subject with Tuberous Sclerosis. Methods disclosed herein may result in reducing the severity of one or more of the subject's with Tuberous Sclerosis symptoms. Methods disclosed herein may result in alleviating one or more of the subject's with Tuberous Sclerosis symptoms.

In some instances, methods disclosed herein comprise treating a subject with MEF2C haploinsufficiency. MEF2C haploinsufficiency syndrome (MCHS) is a neurodevelopmental disorder associated with intellectual disability, autistic features, epilepsy, and abnormal movements. Symptoms include, but are not limited to psychomotor delay, generalized hypotonia, poor eye contact, hand-mouth stereotypies, strabismus, and minor facial dimorphisms. Some symptoms may be due to an altered excitatory to inhibitory ratio (E/I ratio) of the normal electrical activity in the brain. Methods disclosed herein may comprise restoring the E/I ratio toward a normal range (e.g, that of a person without a MEF2C haploinsufficiency) and improving signs of ASD. Methods may comprise assessing the presence and/or severity of the subject's symptoms before delivering a compound disclosed herein to the subject with MEF2C haploinsufficiency. Methods may comprise assessing the presence and/or severity of the subject's symptoms after delivering a compound disclosed herein to the subject with MEF2C haploinsufficiency. Methods disclosed herein may result in reducing the severity of one or more of the subject's with MEF2C haploinsufficiency symptoms. Methods disclosed herein may result in alleviating one or more of the subject's with MEF2C haploinsufficiency symptoms.

In some instances, methods disclosed herein comprise treating a subject, wherein the subject is a child. The child may be less than about 14 years old, less than about 13 years old, less than about 12 years old or less than about 10 years old. In some instances, the subject is more than 1 year old, more than 2 years old, more than 3 years old, more than 4 years old, or more than 5 years old.

Methods disclosed herein may comprise selecting a subject for treatment. In some instances, the subject is selected based on expression of a gene in the subject. In some instances, the subject is selected based on a sequence of a gene in the subject. In some instances, the subject is selected based on a mutation in a gene in the subject. The mutation may be a deletion mutation. The deletion mutation may be a haploinsufficiency (e.g., MEF2C haploinsufficiency). The mutation may be a frameshift mutation. The mutation may be a single nucleotide polymorphism. In some instances, the subject is selected based on the subject's expression of a protein encoded by the gene. In some instances, the subject is selected based on activity of the protein encoded by the gene. The gene may be MEF2C, which encodes myocyte enhancer factor 2C (MEF2C). The gene may be SLC32A1, which encodes vesicular γ-aminobutyric acid (GABA) transporter (VGAT). The gene may be SLC17A6, which encodes vesicular glutamate transporter 2 (VGLUT2). The gene may be SYP, which encodes the protein synaptophysin, also known as major synaptic vesicle protein p38. The gene may be GAD65, which encodes glutamic acid decarboxylase.

Methods may comprise obtaining an expression level of a gene disclosed herein. Methods may comprise obtaining an expression level of a protein disclosed herein. Methods may comprise obtaining information about activity of a protein disclosed herein. Methods may comprise analyzing an expression level of a gene disclosed herein. Methods may comprise analyzing an expression level of a protein disclosed herein. Methods may comprise analyzing information about activity of a protein disclosed herein. Methods may comprise quantifying an expression level of a gene disclosed herein. Methods may comprise quantifying an expression level of a protein disclosed herein. Methods may comprise quantifying information about activity of a protein disclosed herein. Quantifying and analyzing expression and activity of genes and proteins, respectively, are well known in the art. Non-limiting examples of quantifying and analyzing gene expression are q-PCR, microarray, sequencing, and Northern blot. Methods may comprise analyzing allele-specific expression. Non-limiting examples of quantifying and analyzing protein expression and activity are immunohistochemistry, Western blot, immunoprecipitation, flow cytometry, immunofluorescence, and combinations thereof. Methods may comprise sequencing a gene disclosed herein.

Methods may comprise obtaining an expression level of a gene disclosed herein, wherein the expression level is that of a cell of the subject. Methods may comprise obtaining a cell from the subject. Methods may comprise isolating a cell from the subject. The cell may be a brain cell. The cell may be a circulating cell. The cell may be a cell circulating in cerebrospinal fluid. The cell may be a blood cell. The cell may be a skin cell. The cell may be an epithelial cell. The cell may be a human induced pluripotent stem cell derived from a patient skin biopsy and differentiated into a neuron or other brain cells (e.g., astrocytes, oligodencrocytes, and microglia) and assayed in a two-dimensional (2D) culture system or in a 3D cerebral organoid, a small brain like structure produced in vitro and thus able to model a "disease-in-a-dish."

Obtaining the expression level of the gene may comprise isolating a cell-free nucleic acid from the subject. The cell-free nucleic acid may comprise RNA. The cell-free nucleic acid may comprise messenger RNA. The cell-free nucleic acid may consist essentially of messenger RNA. The cell-free nucleic acid may comprise DNA. The DNA may be methylated DNA. Obtaining the expression level of the gene may comprise isolating a cell-free nucleic acid from the subject. The cell-free nucleic acid may be circulating cell-free nucleic acid. Methods may comprise obtaining a sample from the subject, wherein the sample contains the cell-free nucleic acid. Non-limiting examples of such samples are whole blood, plasma, serum, urine, cerebrospinal fluid, and saliva.

Methods disclosed herein may comprise quantifying an expression level of SLC32A1 in a subject, or a cell thereof, or a biological fluid thereof. The subject may have a MEF2C haploinsufficiency. The subject may not have a MEF2C haploinsufficiency. The subject may have a significantly reduced SLC32A1 expression level relative to that of the average of a plurality of control subjects having two copies of the MEF2C gene. The subject may have a significantly reduced SLC32A1 expression level relative to that of the average of a plurality of control subjects exhibiting no signs of or symptoms of a neurological disorder. The subject may have a significantly reduced SLC32A1 expression level relative to that of the average of a plurality of control subjects exhibiting no signs of or symptoms of a neurological disorder disclosed herein. Significantly reduced may be at least about 10% reduced, at least about 20% reduced, at least about 30% reduced, at least about 40% reduced, at least about 50% reduced, at least about 75% reduced, or about 100% reduced.

Methods disclosed herein may comprise quantifying an expression level of SLC17A6 in a subject, or a cell thereof, or a biological fluid thereof. The subject may have a MEF2C haploinsufficiency. The subject may not have a MEF2C haploinsufficiency. The subject may have a significantly increased SLC17A6 expression level relative to that of the average of a plurality of control subjects having two copies of the MEF2C gene. The subject may have a significantly increased SLC17A6 expression level relative to that of the average of a plurality of control subjects exhibiting no signs of or symptoms of a neurological disorder. The subject may have a significantly increased SLC17A6 expression level relative to that of the average of a plurality of control subjects exhibiting no signs of or symptoms of a neurological disorder disclosed herein. Significantly increased may be at least about 10% increased, at least about 20% increased, at least about 30% increased, at least about 40% increased, at least about 50% increased, at least about 75% increased, or about 100% increased.

Methods disclosed herein may comprise quantifying an expression level of synaptophysin (SYP), a presynaptic protein, in a subject, or a cell thereof, or a biological fluid thereof. The subject may have a MEF2C haploinsufficiency. The subject may not have a MEF2C haploinsufficiency. The subject may have a significantly reduced SYP expression level relative to that of the average of a plurality of control subjects having two copies of the MEF2C gene. The subject may have a significantly reduced SYP expression level relative to that of the average of a plurality of control subjects exhibiting no signs of or symptoms of a neurological disorder. The subject may have a significantly reduced SYP expression level relative to that of the average of a plurality of control subjects exhibiting no signs of or symptoms of a neurological disorder disclosed herein. Significantly reduced may be at least about 10% reduced, at least about 20% reduced, at least about 30% reduced, at least about 40% reduced, at least about 50% reduced, at least about 75% reduced, or about 100% reduced.

Methods disclosed herein may comprise quantifying an expression level of GAD65 in a subject, or a cell thereof, or a biological fluid thereof. The subject may have a MEF2C haploinsufficiency. The subject may not have a MEF2C haploinsufficiency. The subject may have a significantly reduced GAD65 expression level relative to that of the average of a plurality of control subjects having two copies of the MEF2C gene. The subject may have a significantly reduced GAD65 expression level relative to that of the average of a plurality of control subjects exhibiting no signs of or symptoms of a neurological disorder. The subject may have a significantly reduced GAD65 expression level relative to that of the average of a plurality of control subjects exhibiting no signs of or symptoms of a neurological disorder disclosed herein. Significantly reduced may be at least about 10% reduced, at least about 20% reduced, at least about 30% reduced, at least about 40% reduced, at least about 50% reduced, at least about 75% reduced, or about 100% reduced.

Compounds

Disclosed herein is a method of treating Autism Spectrum Disorder (ASD), Intellectual and Developmental Disability (IDD), epilepsy, Rett syndrome, and/or Tuberous Sclerosis in a subject in need thereof with a compound of Formula I, or a pharmaceutically acceptable salt thereof:

Formula I

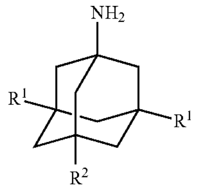

wherein each $R^1$ is independently selected from $-CH_3$ and $-CH_2CH_3$; and $R^2$ is selected from hydrogen and $-ONO_2$.

In some embodiments of a compound of Formula I, or a pharmaceutically acceptable salt thereof, $R^2$ is hydrogen. In some embodiments, $R^2$ is $-ONO_2$.

In some embodiments of a compound of Formula I, or a pharmaceutically acceptable salt thereof, each $R^1$ is different. In some embodiments, each $R^1$ is the same. In some embodiments, each $R^1$ is $-CH_3$. In some embodiments, each $R^1$ is $-CH_2CH_3$.

In some embodiments of a compound of Formula I, or a pharmaceutically acceptable salt thereof, each $R^1$ is $-CH_2CH_3$ and $R^2$ is $-ONO_2$.

Also disclosed herein is a method of treating other forms of Autism Spectrum Disorder (ASD), Intellectual and Developmental Disability (IDD), epilepsy, Rett syndrome, and/or Tuberous Sclerosis in a subject in need thereof with a compound of Formula II, or a pharmaceutically acceptable salt thereof:

Formula II

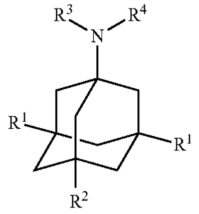

wherein each $R^1$ is independently selected from hydrogen, $C_1$-$C_6$ alkyl, cycloalkyl, heterocycloalkyl, aryl, and heteroaryl;

$R^2$ is selected from hydrogen, $C_1$-$C_6$ alkyl, and $-ONO_2$;

$R^3$ and $R^4$ are each independently selected from hydrogen and $C_1$-$C_6$ alkyl;

or $R^3$ and $R^4$ are taken together with the nitrogen atom to which they are attached to form a heterocycloalkyl.

In some embodiments of a compound of Formula II, or a pharmaceutically acceptable salt thereof, $R^3$ and $R^4$ are independently selected from hydrogen, methyl, ethyl, n-propyl, i-propyl, n-butyl, i-butyl, s-butyl, and t-butyl. In some embodiments, $R^3$ and $R^4$ are independently selected from hydrogen and methyl. In some embodiments, $R^3$ and $R^4$ are the same. In some embodiments, $R^3$ and $R^4$ are different. In some embodiments, $R^3$ and $R^4$ are hydrogen.

In some embodiments of a compound of Formula II, or a pharmaceutically acceptable salt thereof, $R^3$ and $R^4$ are taken together with the nitrogen atom to which they are attached to form a heterocycloalkyl. In some embodiments, $R^3$ and $R^4$ are taken together with the nitrogen atom to which they are attached to form a monocyclic heterocycloalkyl.

In some embodiments of a compound of Formula II, or a pharmaceutically acceptable salt thereof, $R^2$ is hydrogen. In some embodiments, $R^2$ is $C_1$-$C_6$ alkyl. In some embodiments, $R^2$ is —$ONO_2$. In some embodiments, $R^2$ is hydrogen or —$ONO_2$.

In some embodiments, the compound of Formula II, or a pharmaceutically acceptable salt thereof, is a compound of Formula III, or a pharmaceutically acceptable salt thereof:

Formula III

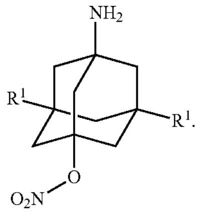

In some embodiments of a compound of Formula II or Formula III, or a pharmaceutically acceptable salt thereof, each $R^1$ is independently selected from hydrogen, $C_1$-$C_6$ alkyl, cycloalkyl, heterocycloalkyl, and aryl. In some embodiments, each $R^1$ is independently selected from hydrogen and $C_1$-$C_6$ alkyl. In some embodiments, each $R^1$ is independently selected from $C_1$-$C_6$ alkyl. In some embodiments, each $R^1$ is independently selected from methyl, ethyl, n-propyl, i-propyl, n-butyl, i-butyl, s-butyl, and t-butyl. In some embodiments, each $R^1$ is independently selected from methyl, ethyl, and n-propyl. In some embodiments, each $R^1$ is independently selected from methyl and ethyl. In some embodiments, each $R^1$ is the same. In some embodiments, each $R^1$ is different. In some embodiments, each $R^1$ is methyl. In some embodiments, each $R^1$ is ethyl. In some embodiments, each $R^1$ is n-propyl.

Formulations

Methods may comprise delivering to a subject a dose of about 1 mg to about 25 mg of a compound disclosed herein. Methods may comprise delivering to a subject a dose of about 1 mg to about 20 mg of a compound disclosed herein. Methods may comprise delivering to a subject a dose of about 1 mg to about 5 mg of a compound disclosed herein. Methods may comprise delivering to a subject a dose of about 5 mg to about 10 mg of a compound disclosed herein. Methods may comprise delivering to a subject a dose of about 10 mg to about 15 mg of a compound disclosed herein. Methods may comprise delivering to a subject a dose of about 15 mg to about 20 mg of a compound disclosed herein. Methods may comprise delivering to a subject a dose of about 1 mg to about 10 mg of a compound disclosed herein. Methods may comprise delivering to a subject a dose of about 10 mg to about 20 mg of a compound disclosed herein. Doses of 1 to 5 mg of compound for a child (pediatric patient) may be sufficient per day. The dose may be slowly increased as tolerated up to about 20 mg per day in divided dosage. The dose may be slowly increased over one or more weeks.

Methods may comprise delivering a dose of a compound disclosed herein once per day. Methods may comprise delivering a dose disclosed herein once per day. Methods may comprise delivering a dose disclosed herein twice per day. Methods may comprise delivering a first dose at a first time point during a day and a second dose at a second time point during the day. The first dose and the second dose may be the same. The first dose and the second dose may be different.

Methods disclosed herein may comprise increasing a daily dose of a compound disclosed herein over time. For example, methods may comprise delivering at least one compound disclosed herein at a first dose for a first week, and delivering the at least one compound at a second dose for a second week, wherein the first dose and the second dose are different. In some instances, the second dose is greater than the first dose. In some instances, the second dose is less than the first dose.

Methods disclosed herein may comprise orally delivering to a subject at least one compound disclosed herein. The compound may be delivered orally via a tablet or capsule. The compound may be delivered orally as a liquid solution. The liquid solution may be swallowed. The liquid solution may be delivered via a dropper or pipet. Alternatively or additionally, delivering may comprise injecting the compound (parenteral administration), applying the compound topically, inhaling the compound, administering the compound transnasally to the brain, or any combination thereof.

Methods disclosed herein may comprise delivering a pharmaceutical composition comprising at least one compound disclosed herein. The pharmaceutical composition may comprise a pharmaceutically acceptable diluent, excipient, carrier, or a combination thereof. The term "pharmaceutically acceptable" as used herein, refers to a material that does not abrogate the biological activity or properties of the compounds described herein, and is relatively nontoxic (i.e., the toxicity of the material significantly outweighs the benefit of the material). In some instances, a pharmaceutically acceptable material may be administered to an individual without causing significant undesirable biological effects or significantly interacting in a deleterious manner with any of the components of the composition in which it is contained.

Pharmaceutical compositions herein may be formulated using one or more physiologically acceptable carriers including excipients and auxiliaries which facilitate processing of the active agents into preparations which are used pharmaceutically. Proper formulation is dependent upon the route of administration chosen. A summary of pharmaceutical compositions is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999).

Pharmaceutical compositions disclosed herein may comprise a pharmaceutically acceptable diluent(s), excipient(s), or carrier(s). The pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions also contain other therapeutically valuable substances.

Pharmaceutical compositions disclosed herein may be administered to a subject by any suitable administration route, including but not limited to, parenteral (intravenous, subcutaneous, intraperitoneal, intramuscular, intravascular, intrathecal, intravitreal, infusion, or local), topical, oral, or nasal administration.

Formulations suitable for intramuscular, subcutaneous, peritumoral, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity is maintained, for example, by the use of a coating such as lecithin, by the maintenance of the required particle size in the case of dispersions, and by the use of surfactants. Formulations suitable for subcutaneous injection also contain optional additives such as preserving, wetting, emulsifying, and dispensing agents.

For intravenous injections, an active agent may be optionally formulated in aqueous solutions, preferably in physiologically compatible buffers such as Hank's solution, Ringer's solution, or physiological saline buffer.

Parenteral injections optionally involve bolus injection or continuous infusion. Formulations for injection are optionally presented in unit dosage form, e.g., in ampoules or in multi dose containers, with an added preservative. The pharmaceutical composition described herein may be in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an active agent in water soluble form. Additionally, suspensions are optionally prepared as appropriate oily injection suspensions.

EXAMPLES

The following illustrative examples are representative of embodiments of the software applications, systems, and methods described herein and are not meant to be limiting in any way.

Example 1 Mef2c-het Mice Manifest MCHS-like Behaviors and Reduced Viability

Figure 2:
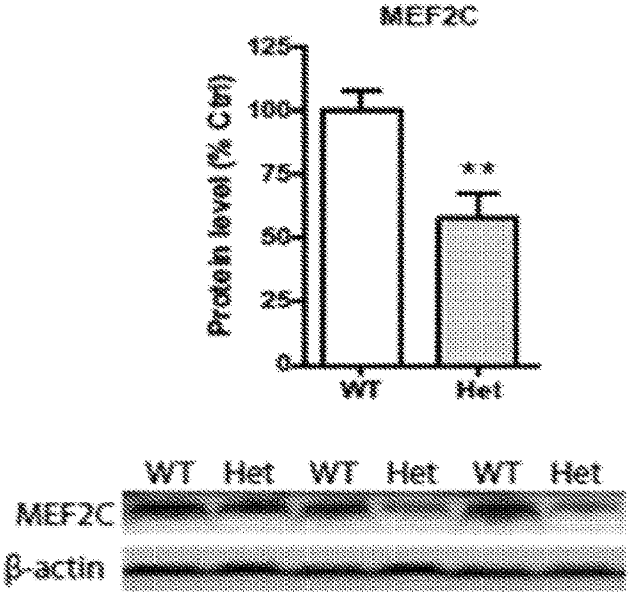
FIG. 2 shows MEF2C protein levels were decreased in Mef2c-het brains. Immunoblotting of forebrain tissue lysates showed decreased MEF2C in Mef2c-het mice compared to WT. Protein levels normalized to β-actin (% control). Representative blots illustrated at bottom. Values are mean+s.e.m., n=5; **P<0.01 by Student's t-test.
Figure 3A:
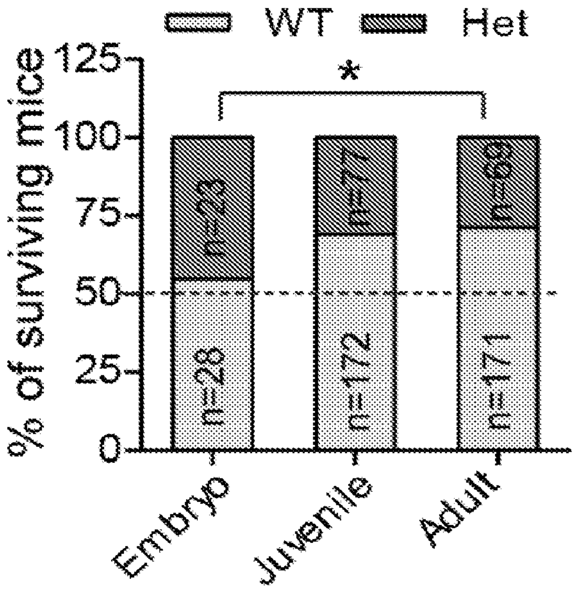
FIG. 3A shows Mef2c-het mice die prematurely. The number of Mef2c-het compared to WT mice was nearly equal at E18, but ~45% that of WT by adulthood (~3 months) (*P<0.05 by Chi-square).

MEF2C protein expression was significantly lower ($P<0.01$) in Mef2c-het mice than in wild-type (WT) littermates FIG. 2), and a significant number of early deaths in the Mef2c-het mice was observed (FIG. 3A). The number of viable animals from crosses between WT and Mef2c-het parents were counted. While the number of WT and Mef2c-het offspring were approximately equal on embryonic day (E)18 (28 vs. 23, respectively), the ratio of surviving Mef2c-het to WT mice was 44% and 40% by postnatal day (P)21 and 90, respectively. The difference between survival at E18 and adult was significant ($P<0.05$ by Chi-square). In addition to reduced viability, Mef2c-het mice that survived to 3 months of age exhibited a decrease (~14%) in body weight compared to their WT counterparts (31.9±1.0 gm for WT vs. 27.4±0.8 gm for Mef2c-het; $P<0.001$ by Student's t-test).

Figure 3B:
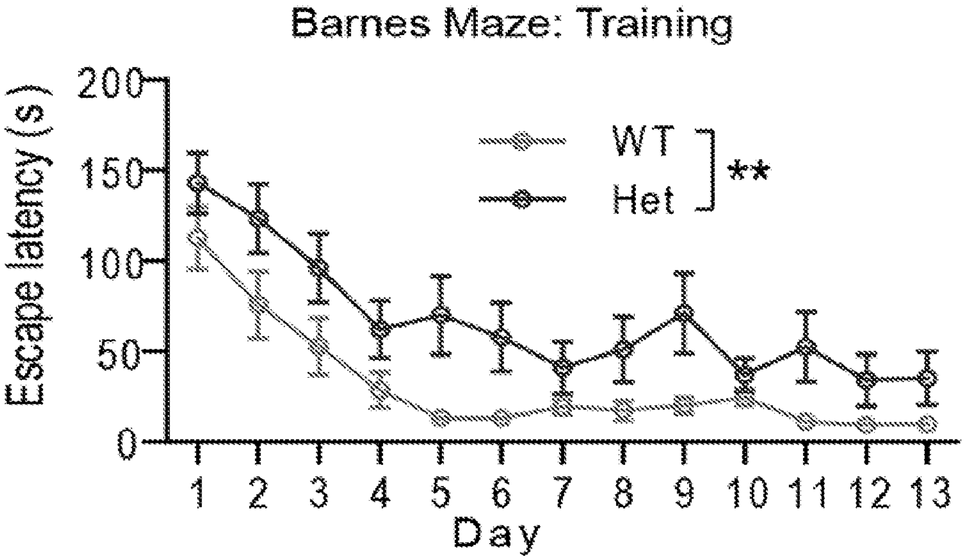
FIG. 3B and FIG. 3C show impaired spatial learned and memory in the Barnes maze of Mef2c-het mice during training (FIG. 3B) and on subsequent probe tests (FIG. 3C).
Figure 3C:
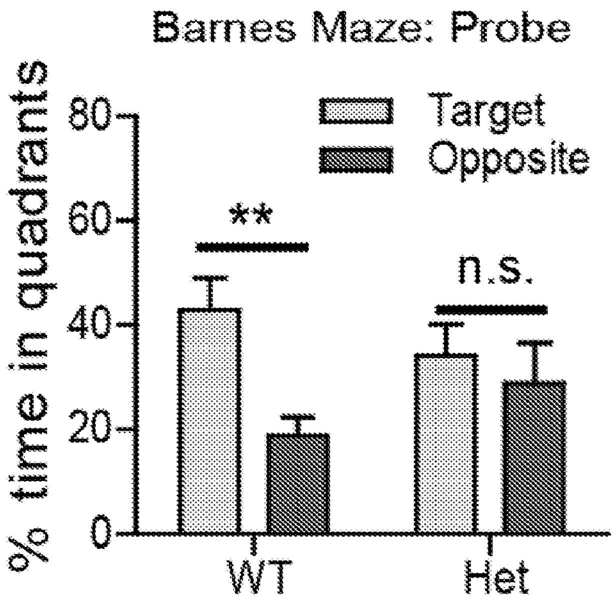
Figure 3D:
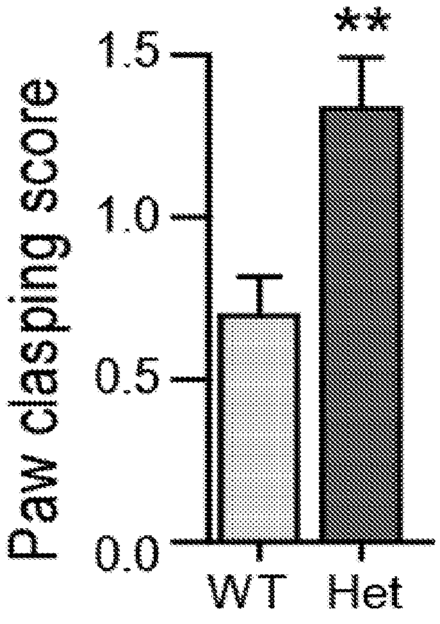
FIG. 3D and FIG. 3E show increased paw clasping (FIG. 3D) and repetitive head dipping (FIG. 3E) of Mef2c-het mice in hole-board exploration. Data are mean±s.e.m.; n=9-11 mice per genotype in FIGS. 3 B, C and E; n=30 (WT) and 21 (het) in d; n.s. not significant, *P<0.05, **P<0.01 by Student's t-test (FIGS. 3C-E) or ANOVA (FIG. 3B).
Figure 3E:
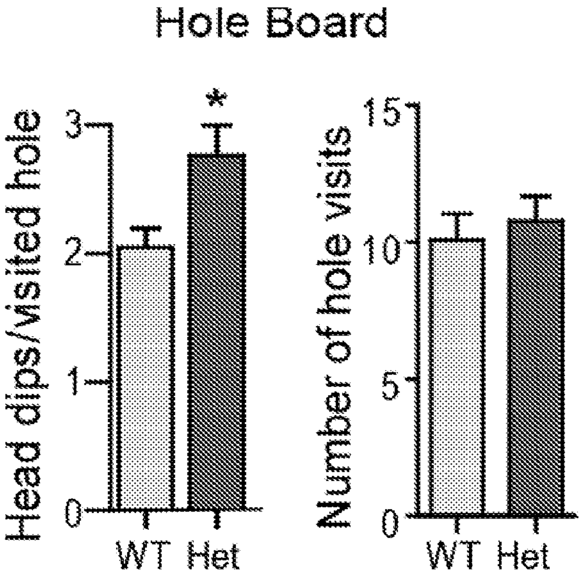

To determine whether adult Mef2c-het mice display MCHS-like phenotypes, behavioral tests were performed on male Mef2c-het mice and their WT littermates (≥3 months of age). Similar to human patients showing cognitive impairment, Mef2c-het mice performed poorly in the Barnes maze, a test that measures spatial learning and memory function. Mef2c-het mice took a significantly longer time to find the escape tunnel during training sessions (FIG. 3B). In subsequent probe tests, WT mice, but not Mef2c-het mice, showed a preference for the target quadrant compared to the opposite quadrant (FIG. 3C), suggesting impaired spatial memory in the Mef2c-het mice. Mef2c-het mice manifested stereotypies, including abnormal paw-clasping behavior (FIG. 3D) and repetitive head dipping on the hole-board exploration test (FIG. 2E). Taken together, these results suggest that Mef2c-het mice display a wide range of MCHS-like phenotypes modeling MCHS.

Figure 4A:
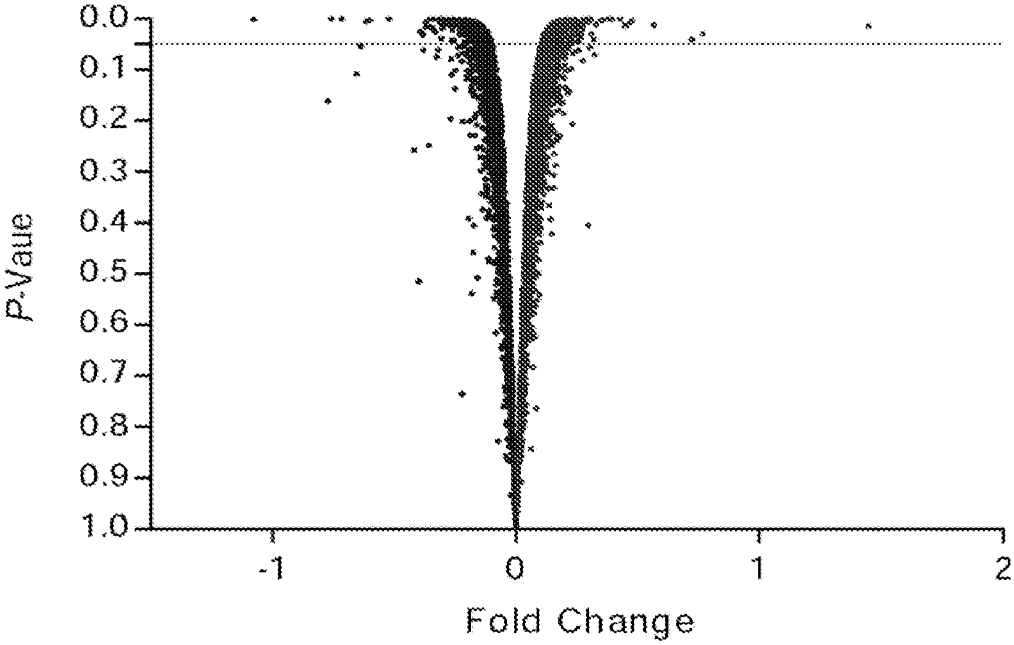
FIG. 4A shows volcano plot shows RNA expression profiling in postnatal day (P)30 Mef2c-het and WT hippocampus (Red=Up, Blue=Down, P<0.05 indicated by green line). [NOTE.
Figures 4B, 4C:
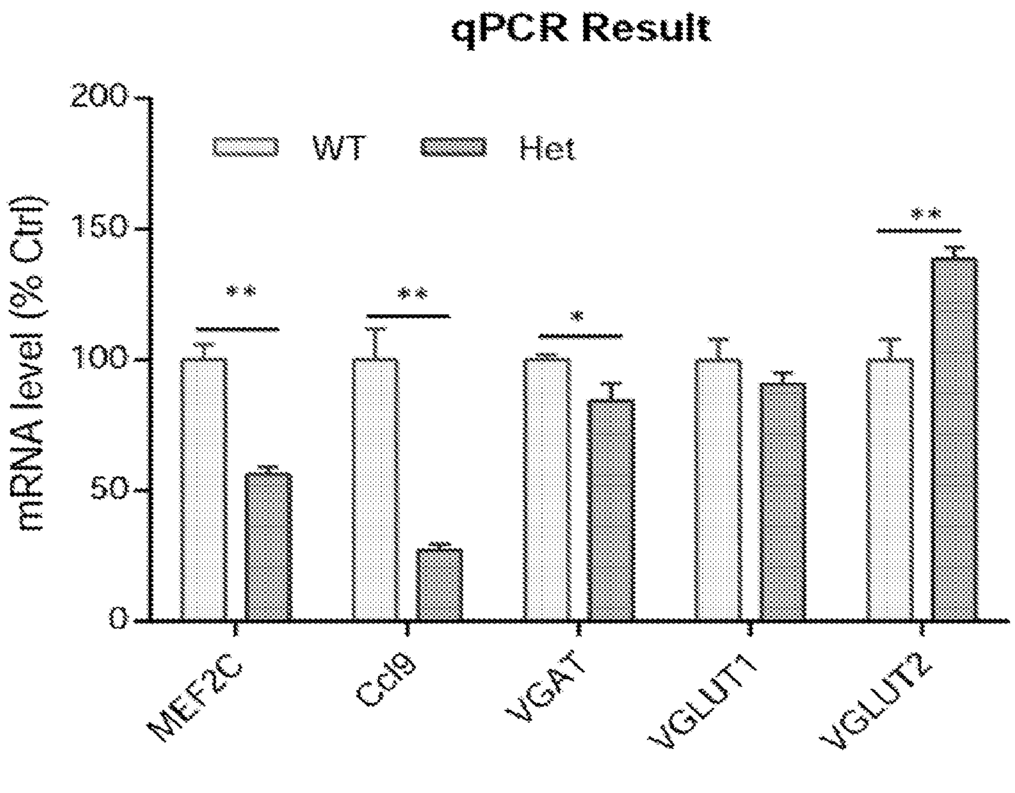
FIG. 4B shows pathway-enrichment analysis of all genes with significantly altered expression in Mef2c-het relative to WT using NextBio and Gene-Ontology (GO-term) filtering.
FIG. 4C shows a graph of qPCR experiments showing expression levels of mRNA (relative to 18S) in Mef2c-het mice as percentage of WT control (% Ctrl; n=4 per group). Data are mean±s.e.m.; *P<0.05, **P<0.01 by Student's t-test.

Example 2 Genes Regulating Neurogenesis and Synaptic Function are Downregulated in Mef2c-het Mice To identify molecular pathways underlying the pathogenesis of MCHS, gene expression of Mef2c-het mice vs. WT littermates were examined by microarray. A total of 783 genes were identified whose expression levels were significantly altered in the hippocampus, including 394 downregulated and 389 upregulated in Mef2c-het mice (FIG. 4A, above green line). With these data, using NextBio pathway analysis, the top neuronal biogroups that were downregulated by Mef2c haploinsufficiency in mice were identified, including biogroups for neurogenesis, neuronal differentiation, and synaptic function (FIG. 4B). Concurrently, the biogroup for regulation of neuronal cell death was upregulated (FIG. 4B). The microarray results were confirmed by qPCR using RNAs extracted from 3-month-old mice (FIG. 4C). Consistent with the NextBio analysis, the mRNA level of vesicular γ-aminobutyric acid (GABA) transporter VGAT (encoded by Slc32a1), representing an inhibitory presynaptic marker, was significantly decreased in Mef2c-het mice. The mRNA level of vesicular glutamate transporters ½ (VGLUT1/2), representing excitatory synaptic markers, was also examined and it was found that the level of VGLUT2, but not VGLUT1, was significantly increased in Mef2c-het mice, indicating dysfunction of both excitatory and inhibitory neurotransmission in these mice.

Figure 5A:
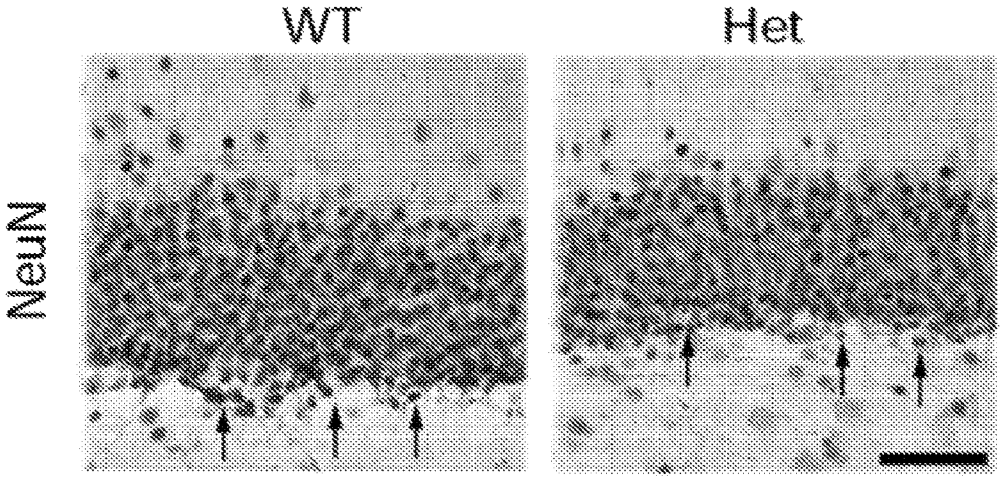
FIG. 5A shows immunohistochemistry showing NeuN+ cells in the dentate gyms (DG) of WT and Mef2c-het mice.
Figure 5B:
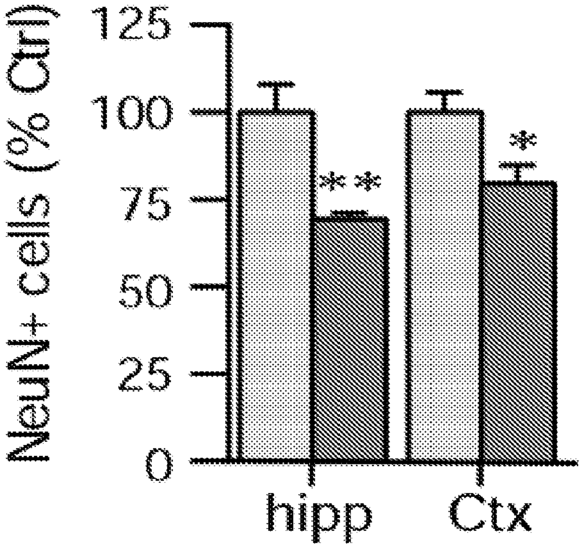
FIG. 5B presents quantification showing decreased NeuN+ cell counts in hippocampus (hipp) and cortex (Ctx) in Mef2c-het mice relative to WT. Hippocampal measurements were obtained on granule cells in the molecular layer of the DG, and the cortical measurement on frontal lobe layers IV and V. FIG. SC and FIG. 5D show increased number of GFAP+ cells consistent with astrocytosis in Mef2c-het mice.
Figure 5C:
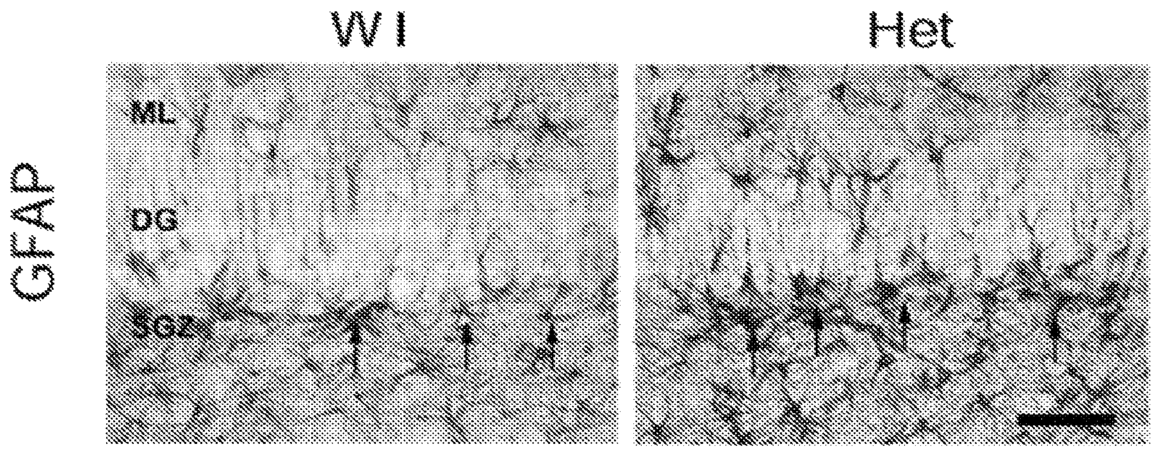
FIG. 5 shows Mef2c-het mice exhibited abnormal neuronal properties.
FIG. 5E shows neurolucida drawing of representative dendrites visualized by Golgi staining in V1 (primary visual cortex), M2ML (secondary visual cortex mediolateral area), and LPtA (lateral parietal association cortex) of the visual cortex of WT and Mef2c-het mice.
FIG. 5F and FIG. 5G show summary graphs of Sholl analysis showing reduction in cumulative number of dendritic intersections (FIG. 5F) and dendritic lengths (FIG. 5G) in Mef2c-het neurons. Scale bar: 50 μm. Data are mean±s.e.m.; n=4 per group. *P<0.05, **P<0.01 by Student's t-test in FIGS. 5A-D and ANOVA in FIG. 5F and FIG. 5G.
Figure 5D:
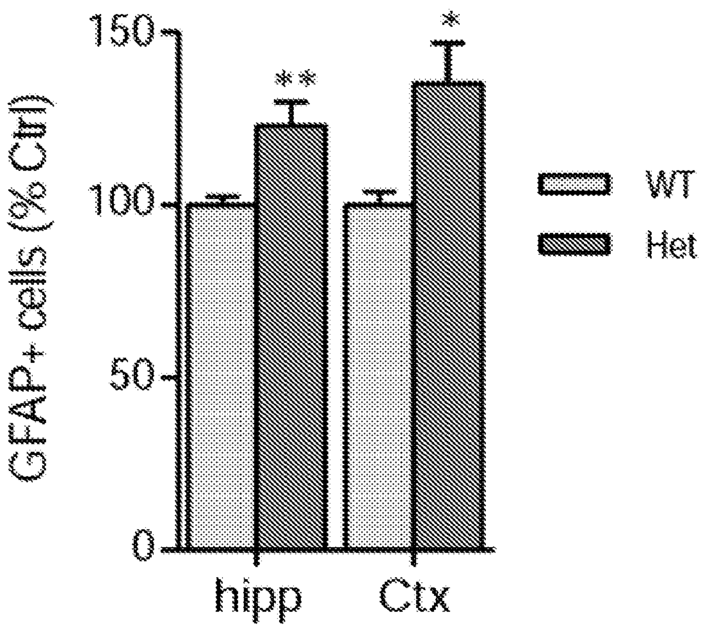

Example 3. Neuronal Reduction and Impaired Excitatory/Inhibitory (E/I) Synaptic Transmission in Mef2c-het Mice In histological experiments using the optical dissector as an unbiased stereological counting method, the total number of NeuN+ cells (i.e., neurons) was significantly decreased in Mef2c-het mice compared to WT in the hippocampus (69.5±1.6% of WT control value, $P<0.01$ by Student's t test) and frontal cortex (79.8±5.1% of WT control, $P<0.05$) (FIG. 5A, FIG. 5B). In contrast to NeuN+ cells, the number of glial fibrillary acid protein (GFAP)+ cells was significantly increased in Mef2c-het mice compared to WT in both the hippocampus (123.0±6.8% of WT control, $P<0.01$) and frontal cortex (135.16±11.70% of WT control, $P<0.05$) (FIG. 5C, FIG. 50).

Figure 5E:
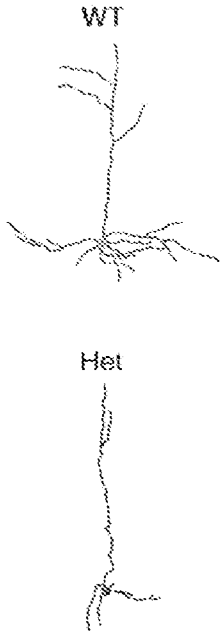
Figure 5F:
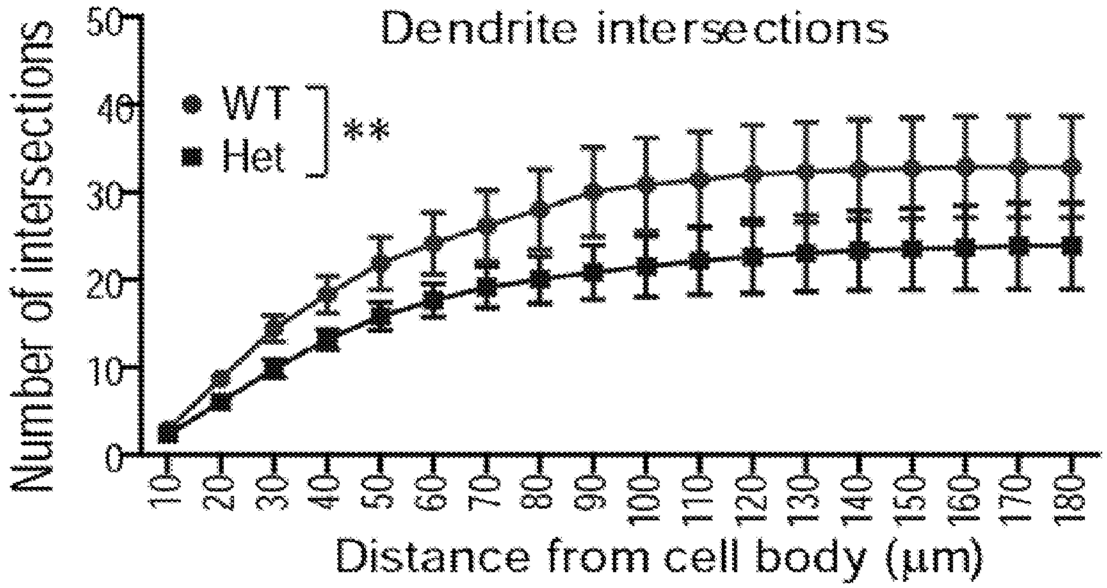
Figure 5G:
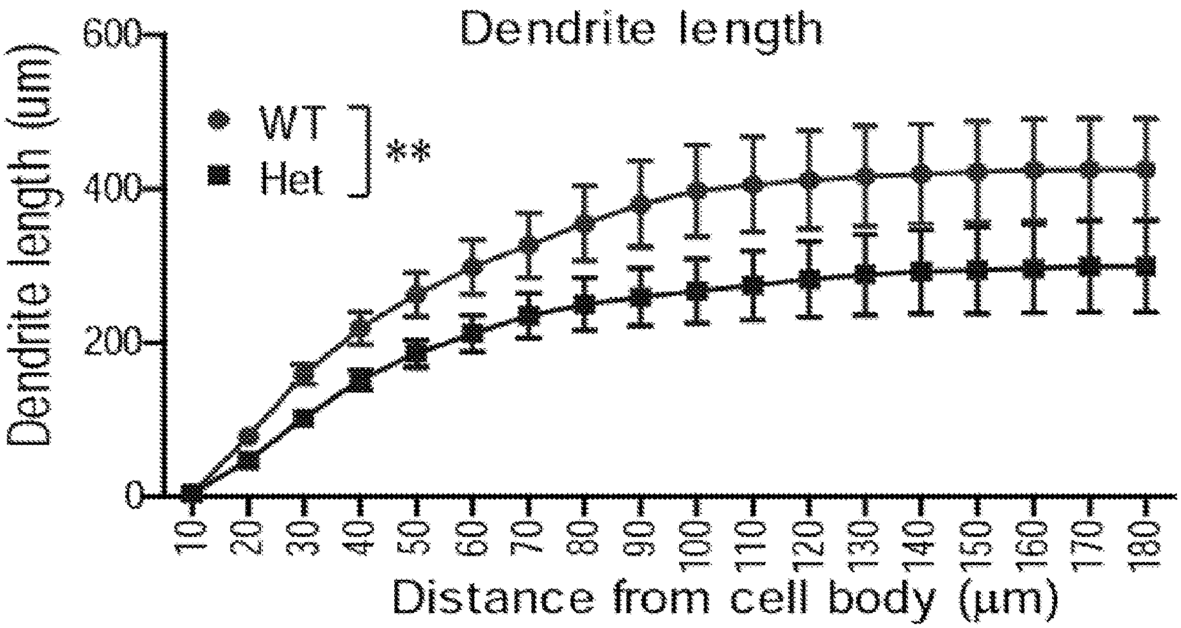

Golgi staining was performed in both Mef2c-het and WT brains to determine dendritic branching patterns of pyramidal cells in layer V of the cerebrocortex using Neurolucida software on 3D montage images (FIG. 5E). Sholl analyses indicated that the dendritic complexity of Mef2c-het neurons was significantly reduced, as demonstrated by decreased dendritic interactions (FIG. 5F) and decreased total dendritic lengths (FIG. 5G).

Figure 6A:
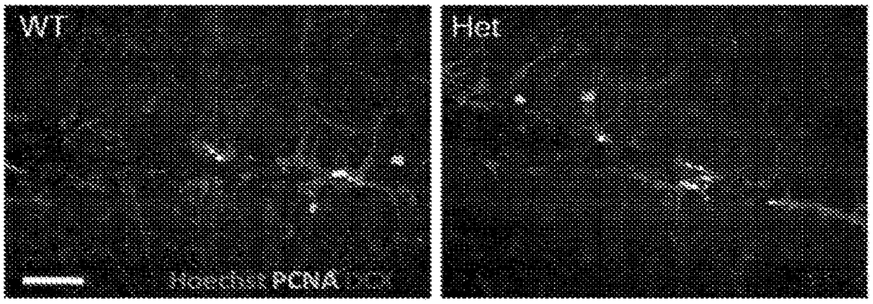
FIG. 6A Confocal images showing PCNA (green) and DCX (red) double staining in the subgranular zone (SGZ) of the DG in 8-week-old WT and Mef2c-het mice.
Figure 6B:
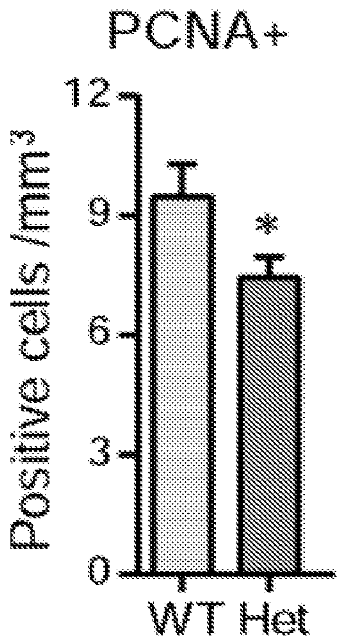
FIG. 6B and FIG. 6C show quantification of PCNA+ and DCX+ cells revealed reduction in the number of proliferating cells (FIG. 6B) and developing neurons (FIG. 6C) in Mef2c-het DG.
Figure 6C:
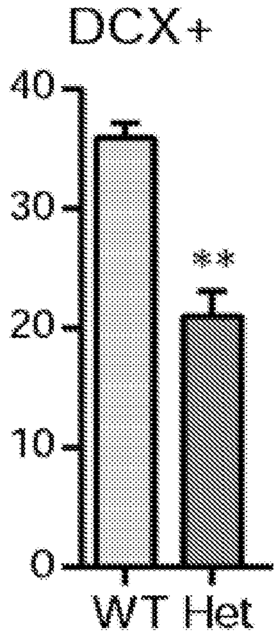
Figure 6D:
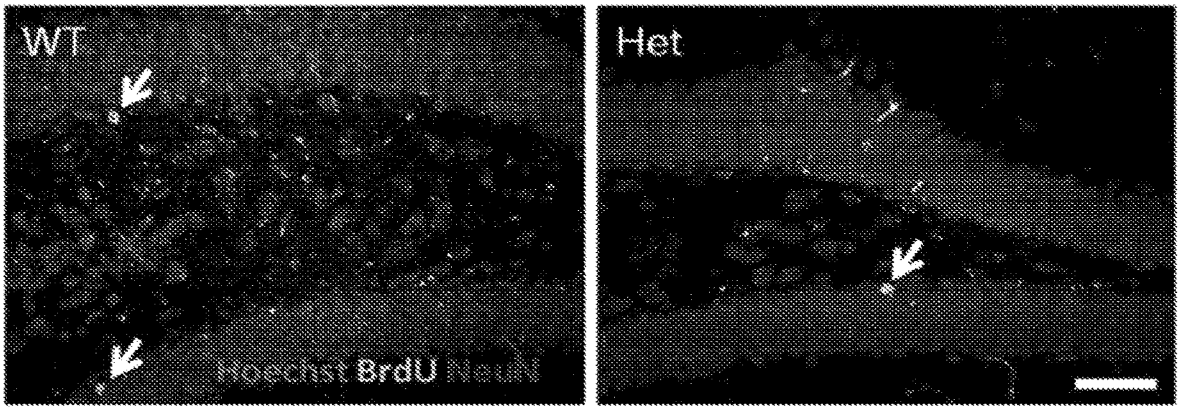
FIG. 6D shows BrdU (green) and NeuN (red) double staining 4 weeks after BrdU injection in 8-week-old WT and Mef2c-het mice revealed newly-born DG neurons (arrows: BrdU+/NeuN+).
Figure 6E:
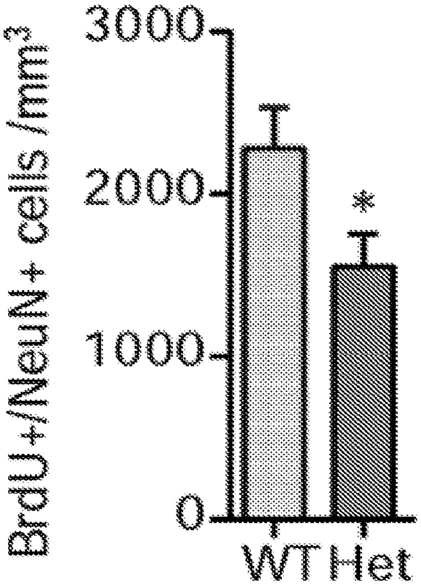
FIG. 6E shows reduction in BrdU+/NeuN+ cells in Mef2c-het DG; n=4 mice per genotype in panel A-E.
Figure 6F:
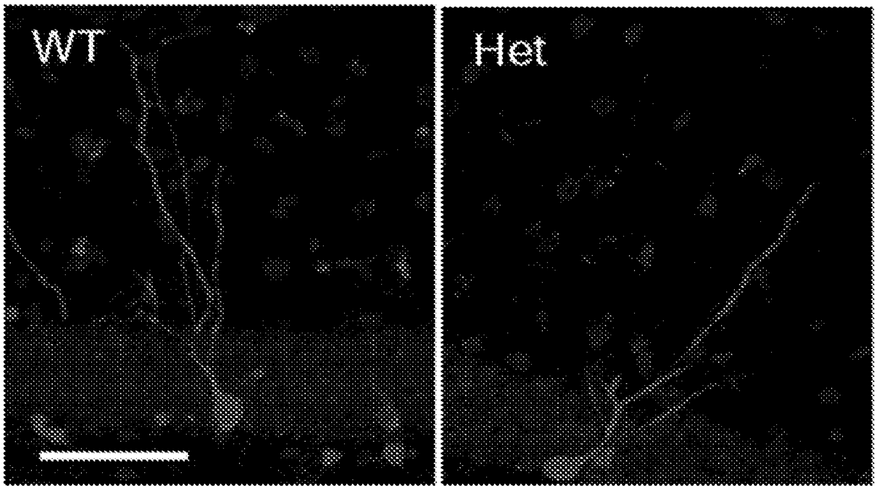
FIG. 6F shows examples of morphological development of neurons born in adult Mef2c-het and WT mice. Dividing cells in the dentate gyrus (DG) were labeled with mCherry via retroviral-mediated gene transduction. Mice were sacrificed 4 weeks later.
Figure 6G:
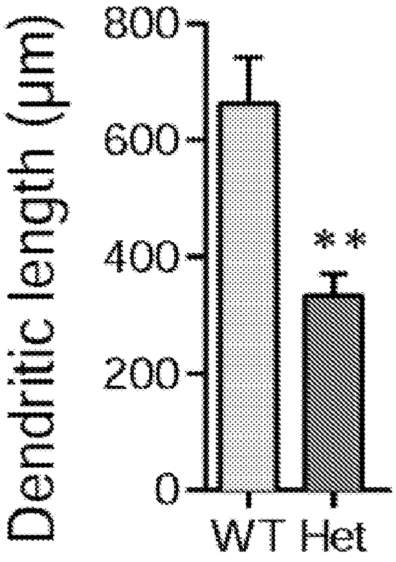
FIG. 6G shows quantification of total dendritic length of 4-week-old neurons revealed reduced dendritic length in Mef2c-het mice (n=17) compared to WT mice (n=12).
Figure 6H:
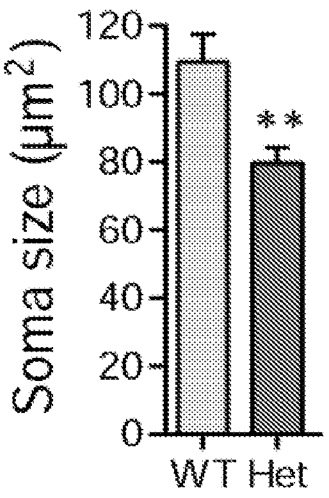
FIG. 6H shows quantification showed reduced somal size in Mef2c-het mice (n=71) compared to WT mice (n=28).
Figure 6I:
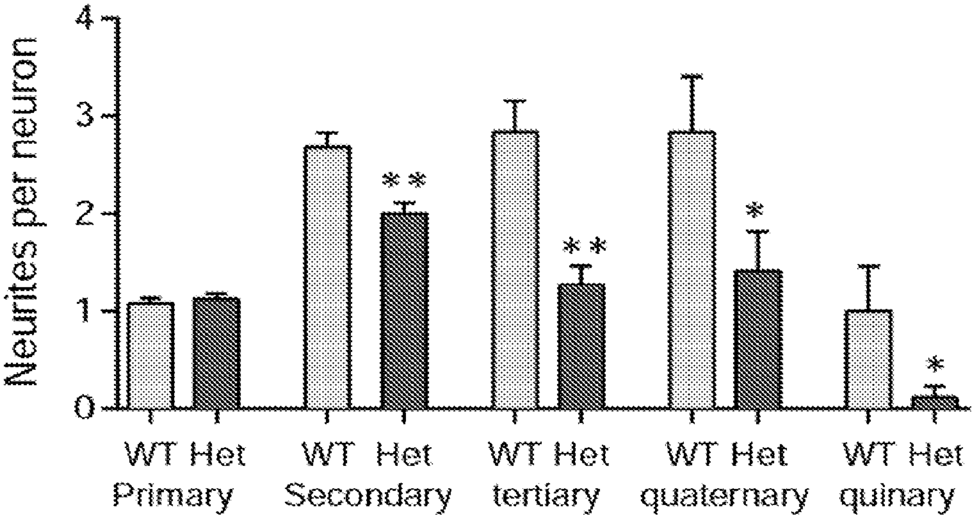
FIG. 6I shows quantification of neurite number showed normal number of primary neurites ($n_{WT}$=25, $n_{Het}$=55), but reduced number of secondary ($n_{WT}$=25, $n_{Het}$=55), tertiary ($n_{WT}$=25, $n_{Het}$=55), quaternary ($n_{WT}$=12, $n_{Het}$=17), and quinary ($n_{WT}$=12, $n_{Het}$=17) neurites of 4-week-old neurons in Mef2c-het compared to WT brain. Section thickness: 40 μm. Scale bar: 50 μm. Values are mean±s.e.m., *P<0.05; ***P<0.001 by Student's t-test.

To further account for the decrease in neuronal number, in addition to the known reduction in embryonic neurogenesis mediated by MEF2C deficiency, adult neurogenesis was characterized in the subgranular zone (SGZ) of the dentate gyms (DG) of 2-3 month-old Mef2c-het mice and a decrease in both the number of proliferating cells (PCNA+, FIG. 6A, FIG. 6B) and developing neurons was observed (DCX+, FIG. 6A, FIG. 6C). The number of BrdU-labeled NeuN+ cells was also reduced in the DG (FIG. 6D, FIG. 6E). These results suggest that reduced adult neurogenesis in Mef2c-het mice contributes to the reduction in neurons. Additionally, the development and complexity of newly formed neurons, visualized via retroviral-mediated gene transduction of mCherry, were also decreased in the Mef2c-het DG, as indicated by decreased somal size and dendritic length (FIG. 6F-I). Therefore, Mef2c haploinsufficiency results in decreased neuronal number, impaired adult neurogenesis, and decreased dendritic complexity in mice.

Figure 7A:
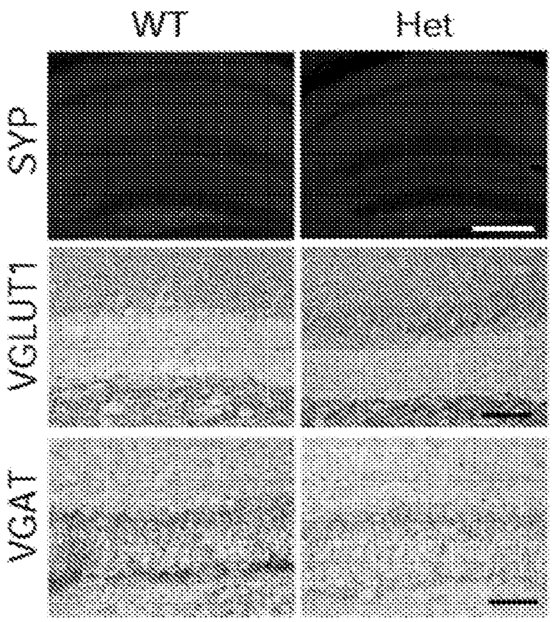
FIG. 7A shows immunohistochemistry of synaptophysin (SYP), VGLUT1, and VGAT in WT and Mef2c-het hippocampus. Scale bars: 500 μm (top panel), 50 μm (middle and bottom panels).
Figure 7B:
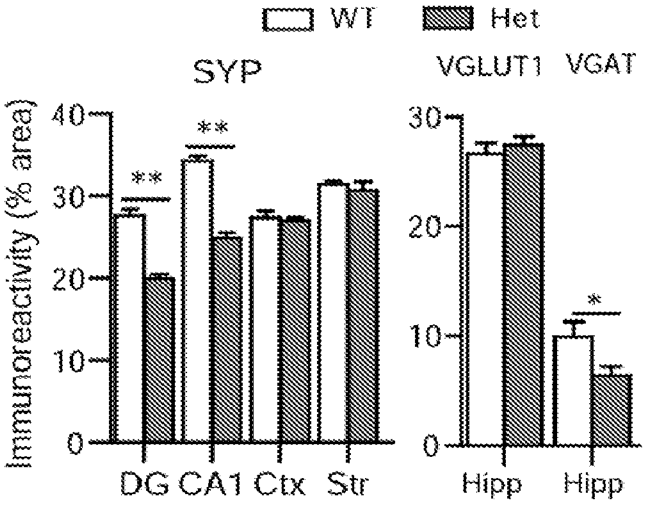
FIG. 7B shows reduced immunoreactivity of SYP in the dentate gyrus (DG) and CA1 regions of Mef2c-het hippocampus but not cortex (Ctx) or striatum (str, left). DG measurements were performed in the molecular layer, CA1 in the pyramidal cell layer, Ctx in frontal cortical layers IV and VI, and str in the putamen at the level of the nucleus accumbens. Reduced expression of VGAT but not VGLUT1 in Mef2c-het hippocampus (right). Data are mean±s.e.m., n=4 per group; *P<0.05, P<0.01 by Student's t-test.
Figure 8A:
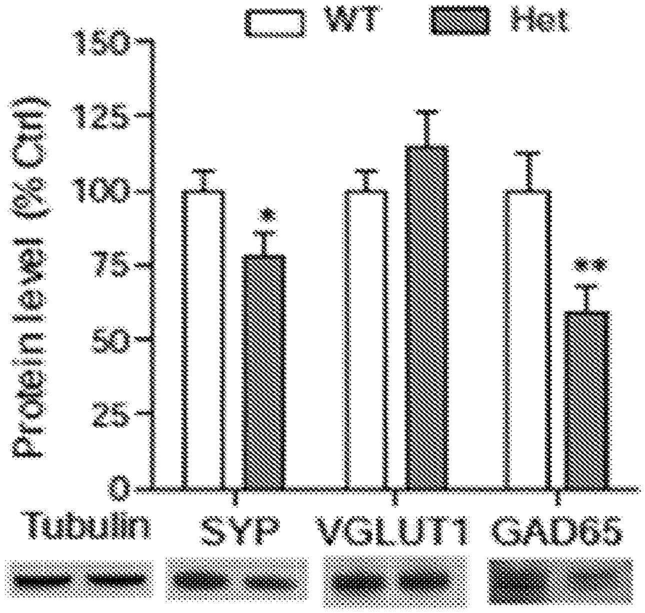
FIG. 8A shows immunoblots of synaptosome-enriched hippocampal lysates showed decreased synaptophysin (SYP) and GAD65 but not VGLUT1 in Mef2c-het mice. Protein levels normalized to α-tubulin (% control). Representative blots illustrated at bottom.
Figure 8B:
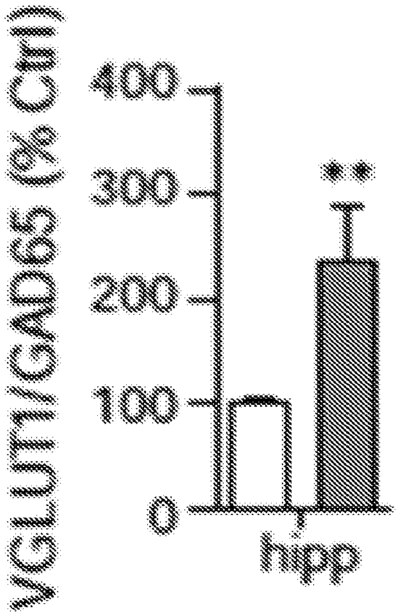
FIG. 8B shows Ratio of VGLUT1 to GAD65.
Figure 8C:
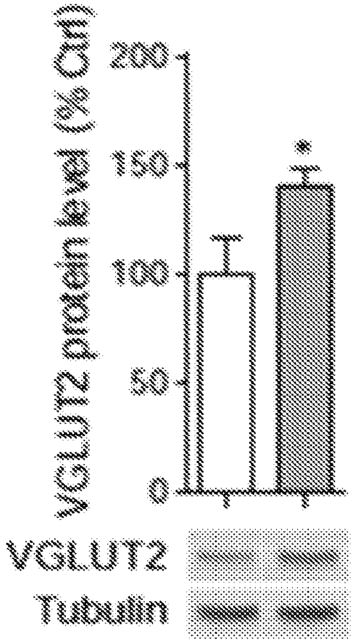
FIG. 8C shows immunoblots of synaptosome-enriched hippocampal lysates showed increased VGLUT2 normalized to α-tubulin in Mef2c-het mice. Representative blots at bottom. Data are mean+s.e.m., n=4 per genotype; *P<0.05, **P<0.01. Statistical significance was determined by Student's t-test.

Synapses in Mef2c-het mice were subsequently examined. Consistent with the microarray analysis predicting an alteration in synaptic proteins, quantitative confocal immunohistochemistry showed that expression of synaptophysin (SYP), a presynaptic marker, was significantly decreased in the hippocampus of Mef2c-het mice (FIG. 7A, FIG. 7B). To better define the synaptic deficit, expression levels of the predominant excitatory synaptic protein VGLUT1 were examined and the inhibitory synaptic protein VGAT by quantitative confocal immunohistochemistry in the hippocampus (FIG. 7A). Expression of VGAT, but not VGLUT1, was significantly decreased in Mef2c-het mice (FIG. 7B). Additionally, immunoblot experiments were performed on hippocampal synaptosome-enriched lysates and it was found that the levels of SYP and GAD65 (another inhibitory neuronal marker), but not VGLUT1, were downregulated in Mef2c-het mice (FIG. 8A). The ratio of VGLUT1 (excitatory neurons) to GAD65 (inhibitory neurons) was significantly increased in Mef2c-het mice (FIG. 8B), a sign of E/I imbalance. Moreover, in contrast to VGLUT1 and in line with mRNA findings, VGLUT2 protein, which is normally expressed only at very low levels in adult hippocampus, was significantly upregulated in Mef2c-het vs. WT (FIG. 8C). Taken together, these findings indicate aberrant excitatory and inhibitory synaptic protein expression in Mef2c-het hippocampus.

Figure 7C:
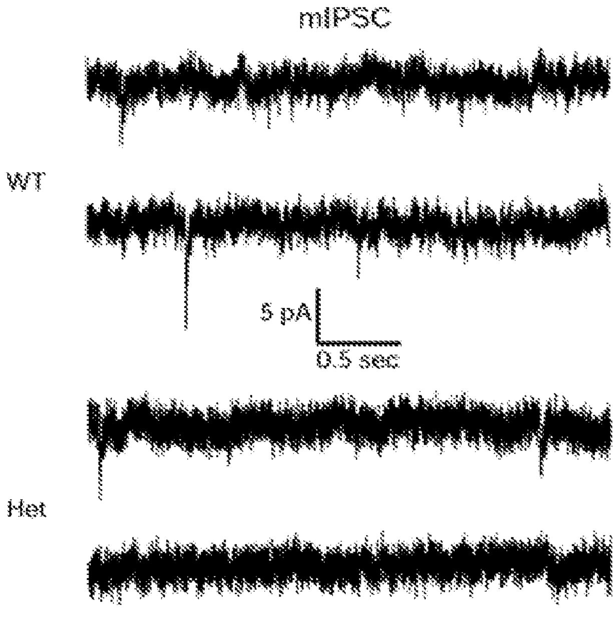
FIGS. 7C and 7D show representative traces of mIPSCs (FIG. 7C) and miniature excitatory postsynaptic currents (mEPSCs) (FIG. 7D) from slice recordings of DG neurons of WT and Mef2c-het mice.

To determine whether these alterations in E/I marker expression were accompanied by abnormalities in functional synaptic transmission, spontaneous miniature excitatory and inhibitory postsynaptic currents (mEPSCs/mIPSCs) from hippocampal slices of Mef2c-het and WT mice were recorded. From the theory of quantal release, a change in miniature frequency reflects a change in presynaptic neurotransmitter release or in the number of synapses, while a change in miniature amplitude is thought to represent a change in postsynaptic function, e.g., the number of postsynaptic receptors. Mef2c-het mice displayed decreased mIPSC frequency (manifested as increased inter-event interval in FIG. 7C, FIG. 7G), in line with the overall reduction in presynaptic VGAT, dendrites and synapses. Reduced mIPSC amplitude was also observed (FIG. 7C, FIG. 7E), possibly reflecting the fact that MEF2 levels are known to correlate with the expression of specific GABA receptor subunits. Interestingly, these mice also showed an increase in mEPSC frequency (manifest as decreased inter-event interval, FIG. 7D, FIG. 7F), similar to a previous report of increased mEPSC frequency in brain specific Mef2c-KO mice. This result was also consistent with the finding of increased expression of presynaptic VGLUT2 in the Mef2c-het hippocampus. The slight reduction in mEPSC amplitude (FIG. 7D, FIG. 7H) relates to the fact that MEF2 transcriptionally normally upregulates glutamate receptor expression. The overall change in mIPSCs and mEPSCs would be expected to result in an elevated E/I ratio in Mef2c-het mice. Indeed, as determined by the quotient of mean mEPSC to mIPSC values, Mef2c-het mice manifested a 116.2% increase in the E/I frequency ratio and a 25.7% increase in E/I amplitude ratio compared to WT mice, confirming the existence of functional E/I imbalance.

Figure 7D:
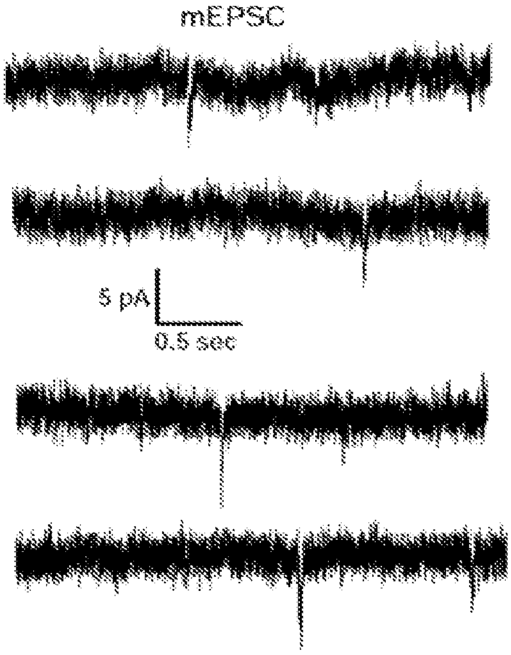
Figure 7E:
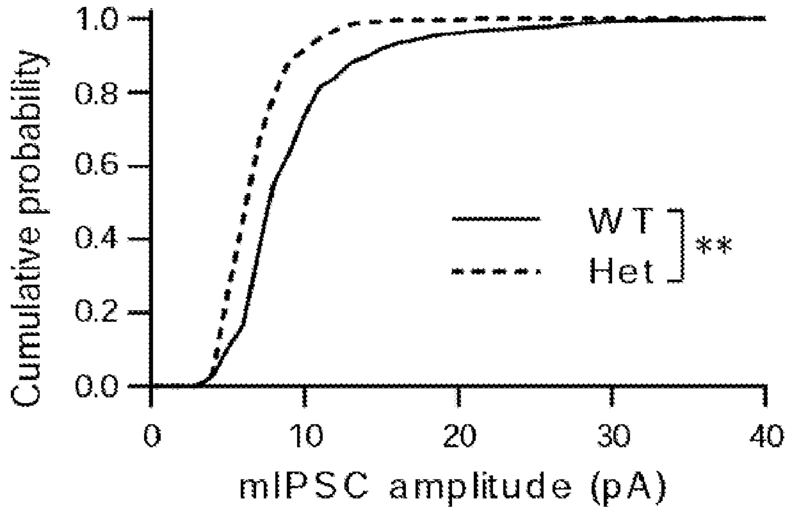
FIGS. 7E-H show cumulative plots of miniature inhibitory postsynaptic currents (mIPSC) and mEPSC amplitude and inter-event intervals. n=7-9 per genotype; P<0.01 by two-sample Kolmogorov-Smirnov test.
Figure 7F:
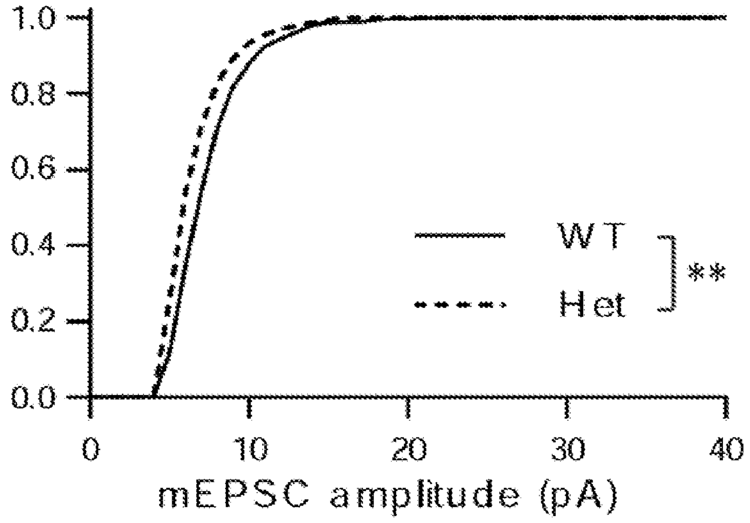
Figure 7G:
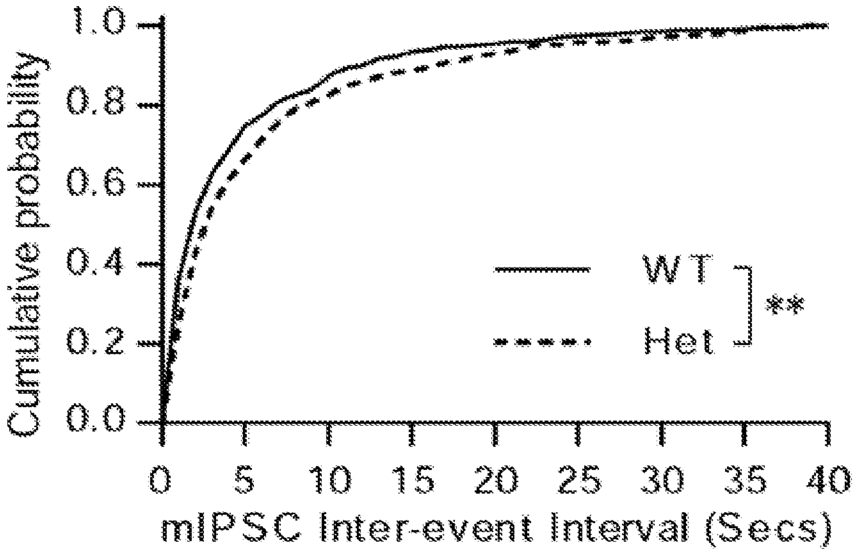
Figure 7H:
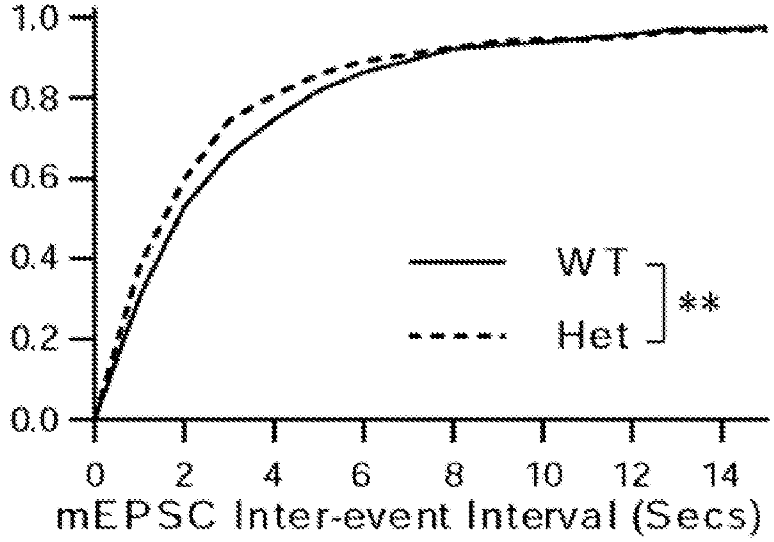
Figure 9A:
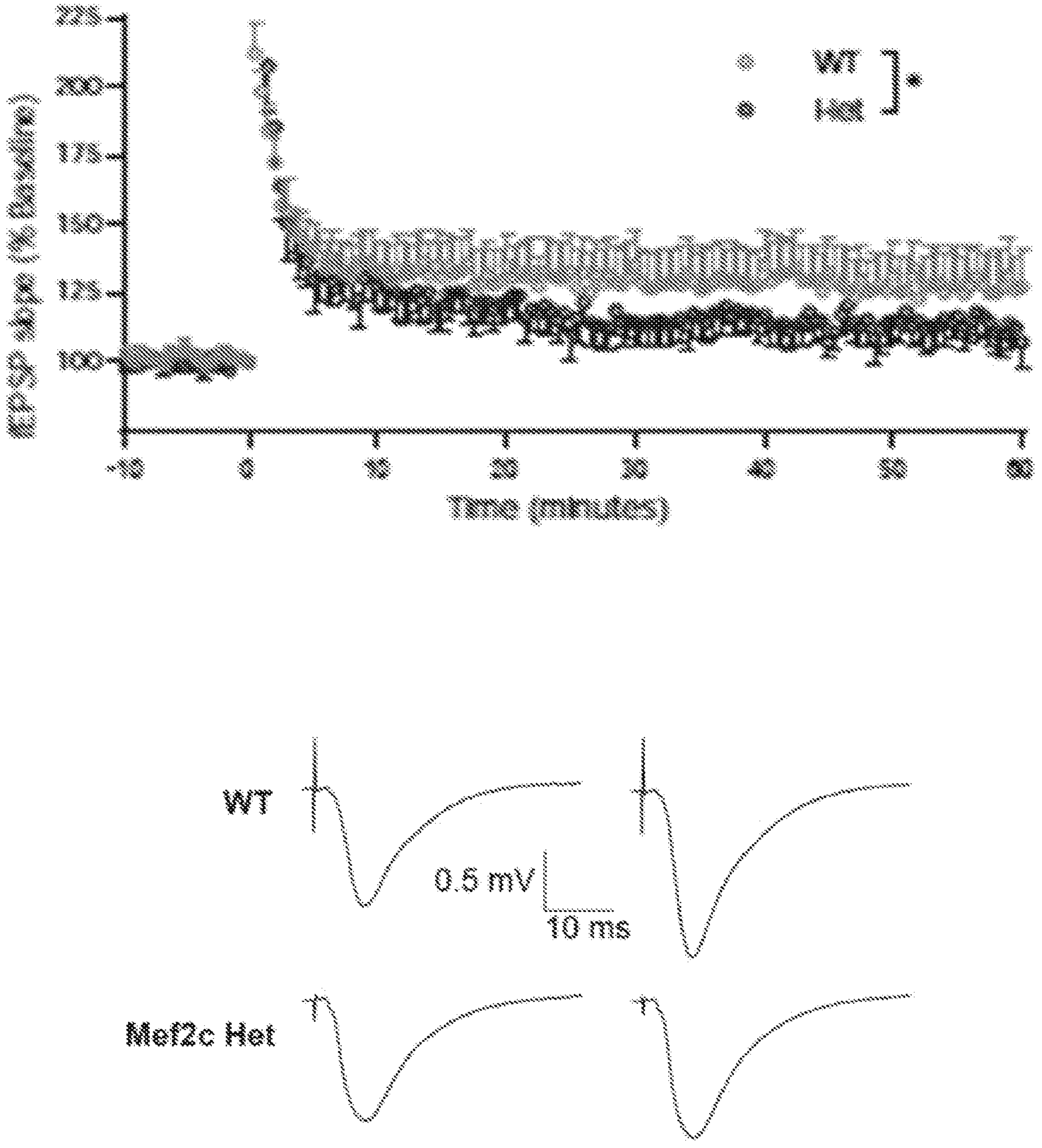
FIGS. 9A and 9B show Mef2c-het mice showed impaired LTP (FIG. 9A) and decreased PPF (FIG. 9B). Representative traces are shown below the graphs. Data are mean±s.e.m., n=5-9 per genotype. Statistical significance was determined by ANOVA (FIG. 9A, *P<0.01) or Sign test (FIG. 9B, *P<0.05).
Figure 9B:
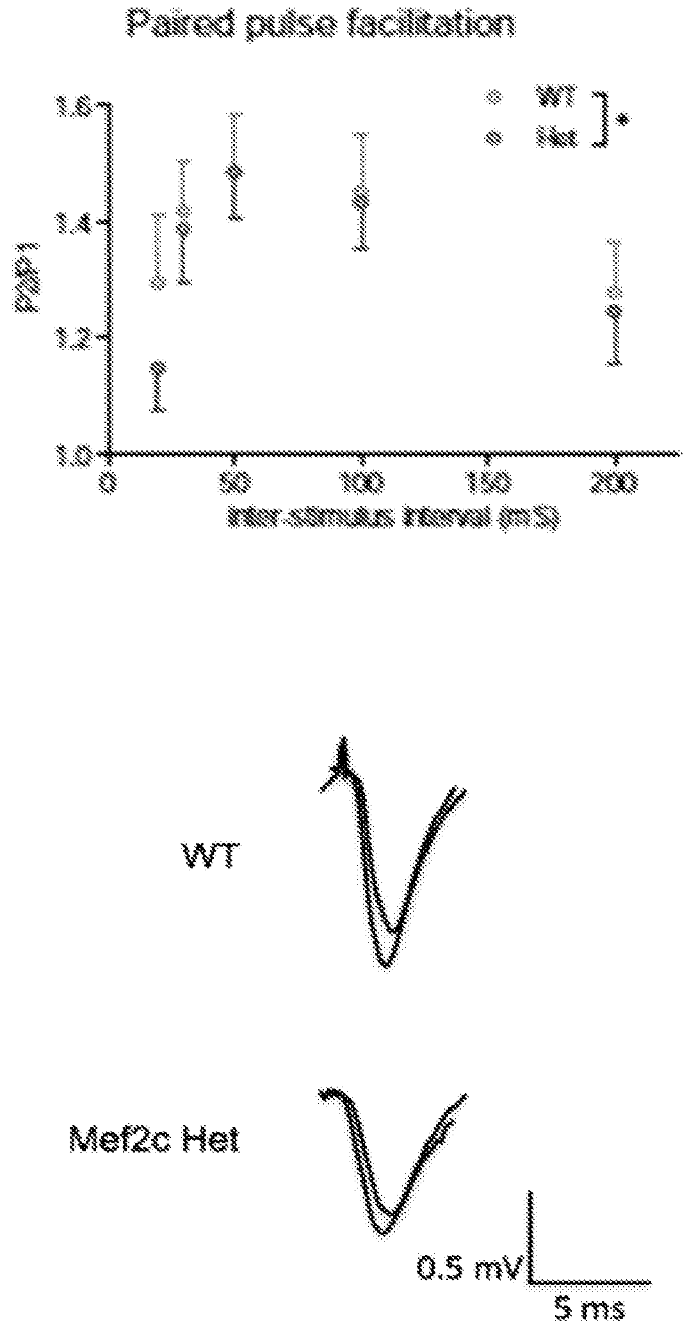

To determine if these neuronal and synaptic defects have a deleterious effect on synaptic plasticity and neuronal circuitry, hippocampal LTP was recorded. Mef2c-het mice exhibited reduced LTP in the CA1 region of the hippocampus (FIG. 9A). Paired pulse facilitation (PPF) represents short-term enhancement of presynaptic function in response to the second of two paired stimuli caused by residual $Ca^{2+}$ in the presynaptic terminal after the first stimulation. For example, decreased PPF is associated with increased probability of neurotransmitter release. A statistical decrease in PPF in Mef2c-het was observed relative to WT mice (FIG. 9B), consistent with the observed small increase in mEPSC frequency (FIG. 7D, FIG. 7F). Collectively, these results show that Mef2c-het mice manifest a reduced number of neurons, accompanied by synaptic deficits with decreased inhibitory and increased excitatory synaptic neurotransmission, thus leading to E/I imbalance.

Example 4 NitroSynapsin Rescues Autistic-Like Behaviors in Mef2c-het Mice

Male Mef2c-het or WT mice were treated with NitroSynapsin or PBS vehicle for 3 months. Behavioral, electrophysiological and histological analyses were then performed to determine the effects of this drug. Importantly, NitroSynapsin treatment of WT-mice showed no effects on the Morris water maze, EPSCs, or LTP.

Figure 10A:
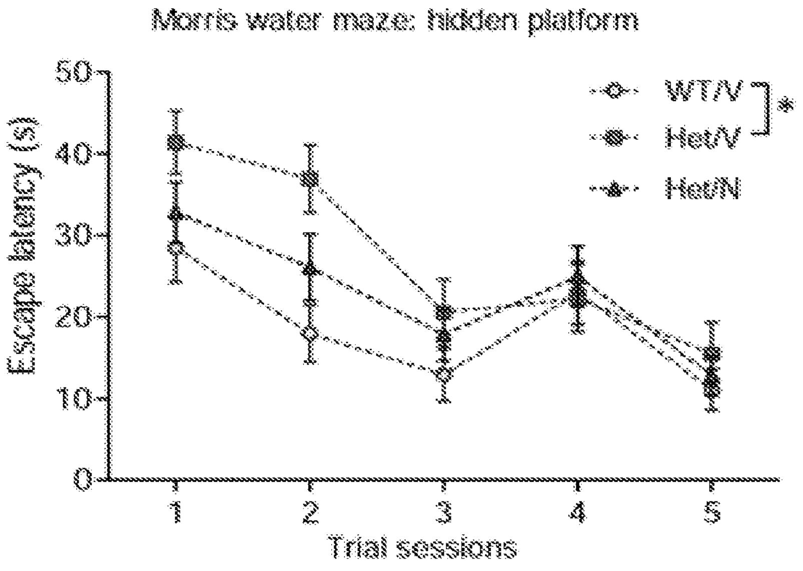
FIG. 10A shows latency of finding hidden platform during training sessions in the Morris water maze.
Figure 10B:
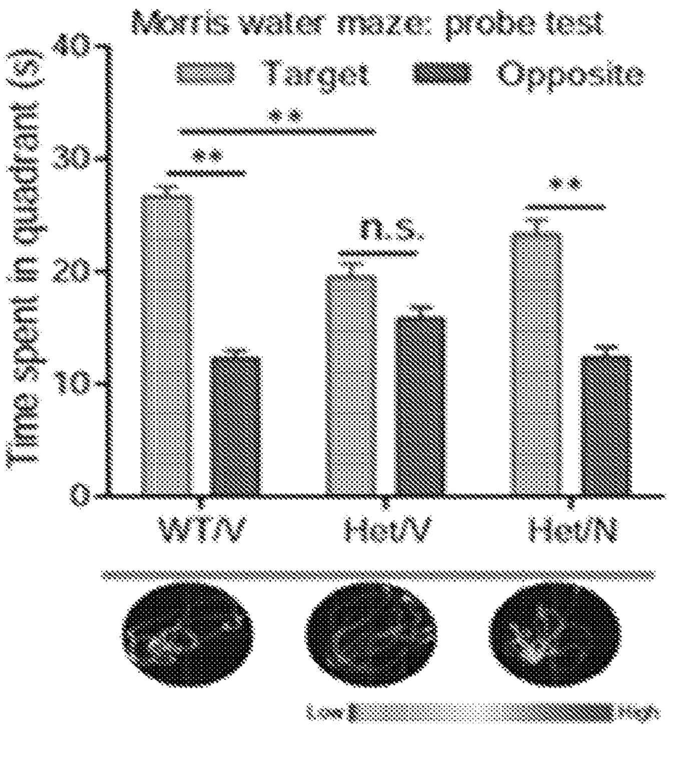
FIG. 10B shows results of a probe test; vehicle-treated Mef2c-het mice (Het/V) showed no preference between target and opposite quadrants, suggesting impaired memory. Treatment with NitroSynapsin (N) rescued this effect (Het/N). Representative swim patterns shown at bottom.
Figure 10C:
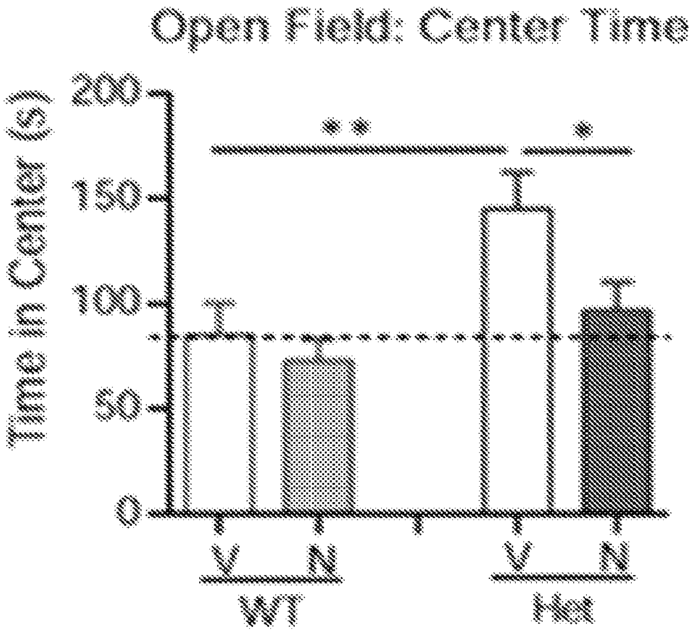
FIG. 10C and FIG. 10D show an open field test; Het/V mice exhibited increased center time that was rescued by treatment with N (FIG. 10C). In contrast, Het/V mice displayed normal total activity (FIG. 10D).
Figure 10D:
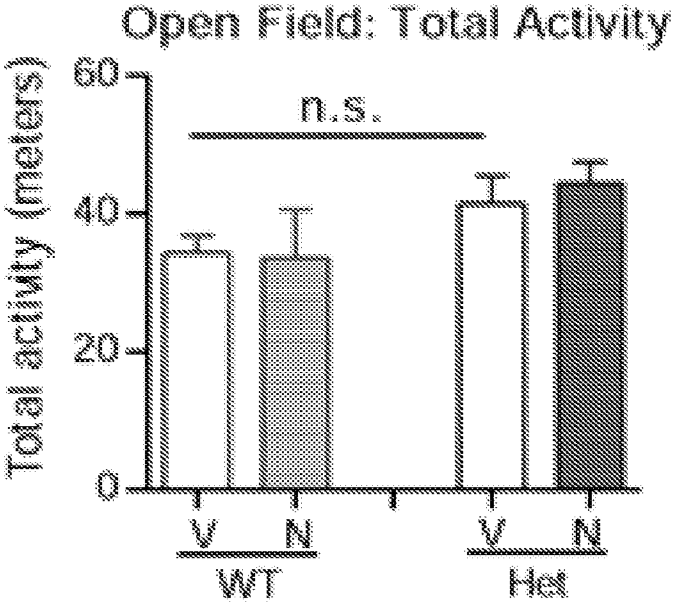
Figure 10E:
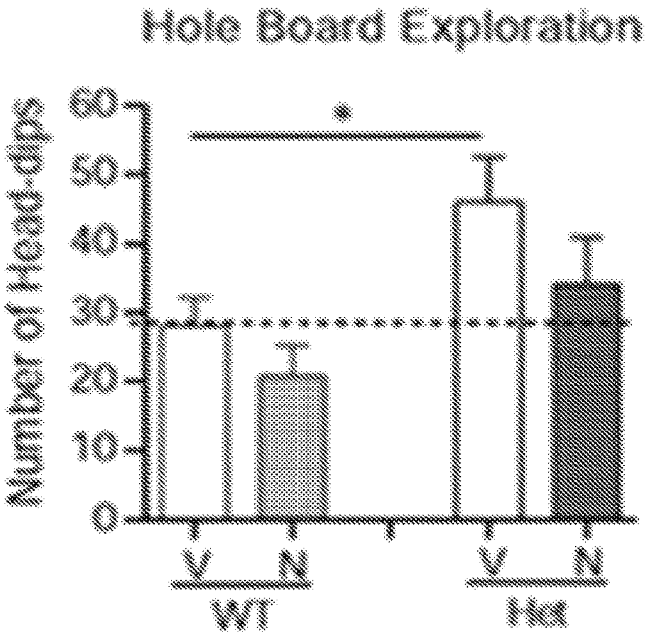
FIG. 10E shows Het/V mice displayed increased head-dips per hole, suggesting repetitive behavior. Each drug rescued.
Figure 10F:
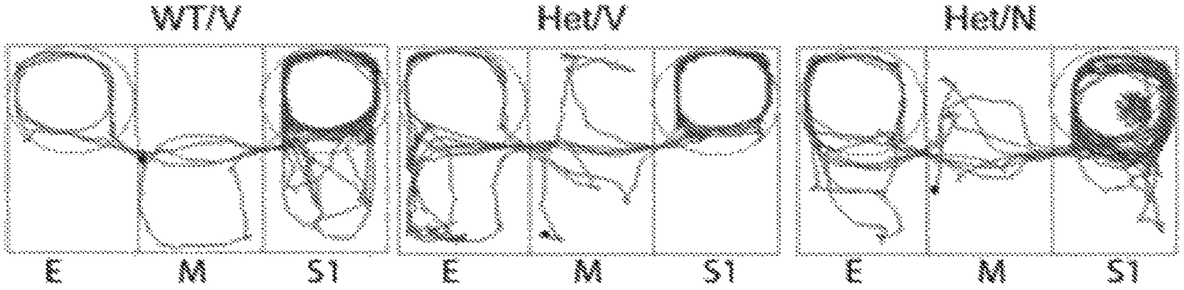
FIGS. 10F-I show N treatment rescued aberrant social ability in Mef2c-het mice.
Figure 10G:
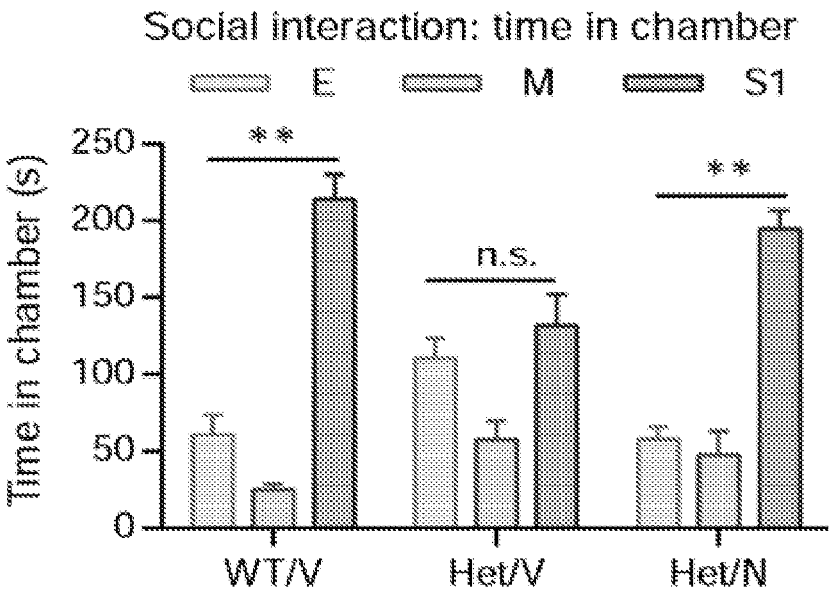
Figure 10H:
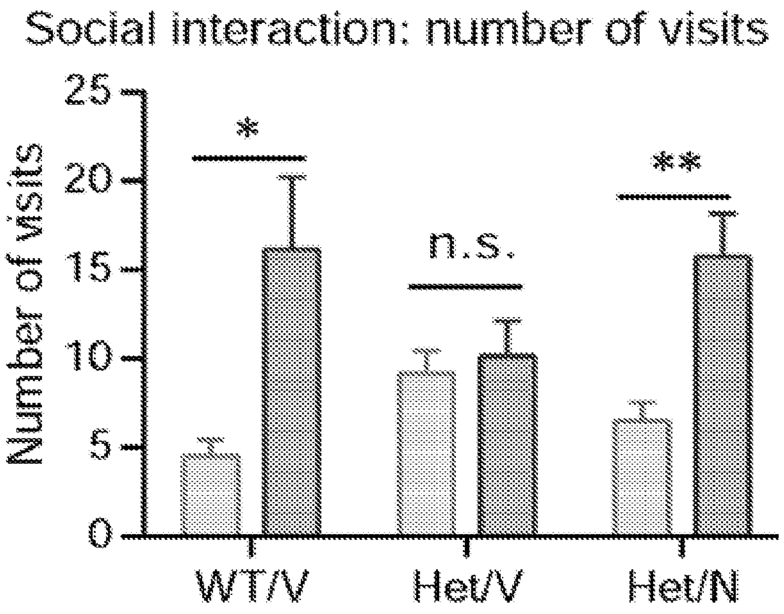
Figure 10I:
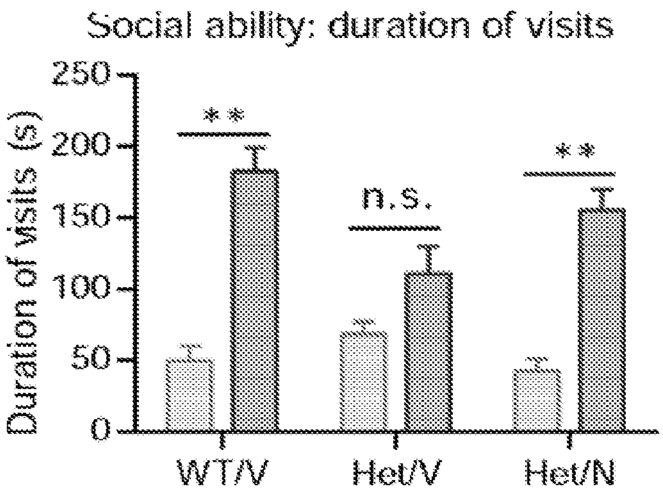
Figure 11:
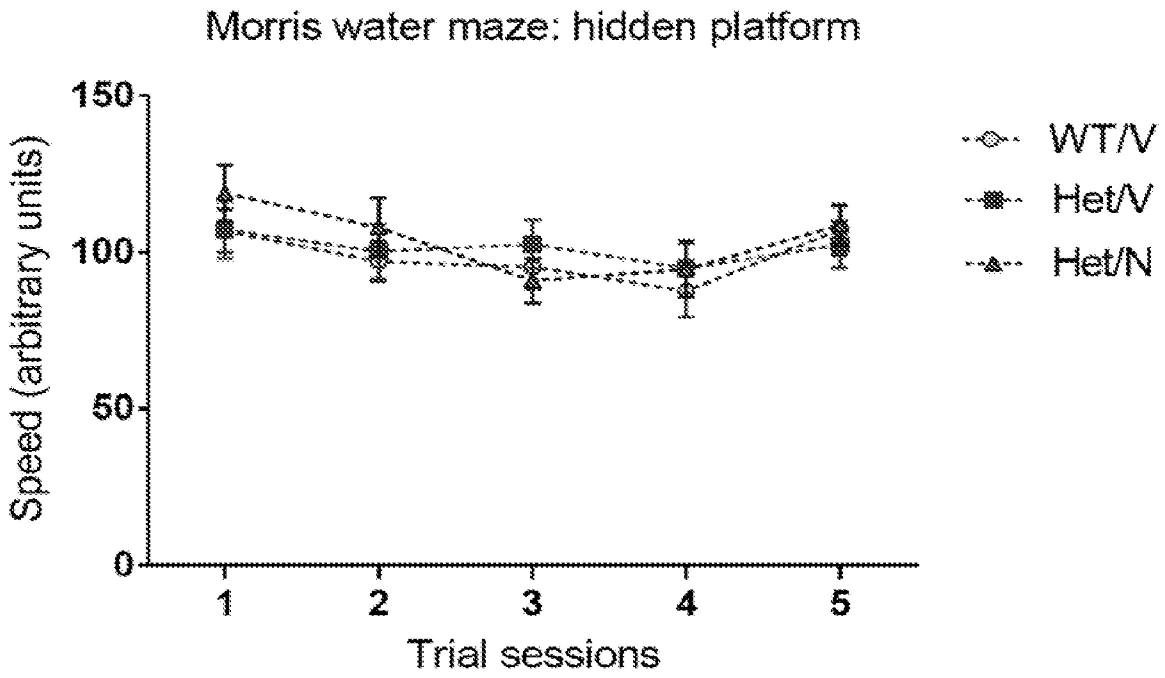
FIG. 11 shows neither Mef2c heterozygosity nor NitroSynapsin treatment altered swimming speed of mice in the Morris water maze. The speed of mice escaping to the hidden platform during the training phase of the Morris water maze was calculated as the distance divided by latency. Unlike the latency to the platform (see FIG. 10), the speed of the three groups of mice (WT/V, Het/V, and Het/N) was not significantly different. Data are mean±s.e.m., n=7-9 per group.
Figure 12A:
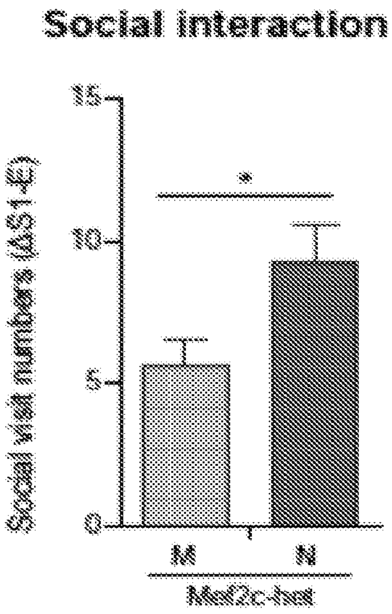
FIG. 12A presents a summary graph showing that the number of social visits by Mef2c-het mice treated with NitroSynapsin (N) was significantly greater than that of memantine (M)-treated mice in the three-chamber social interaction test. Social visits constitute the number of visits to the chamber with a stranger mouse (S1) minus the number of visits to the empty chamber (E). Data are mean+s.e.m., n=7-9 per group; *P<0.05 by Student's t-test.
Figure 13A:
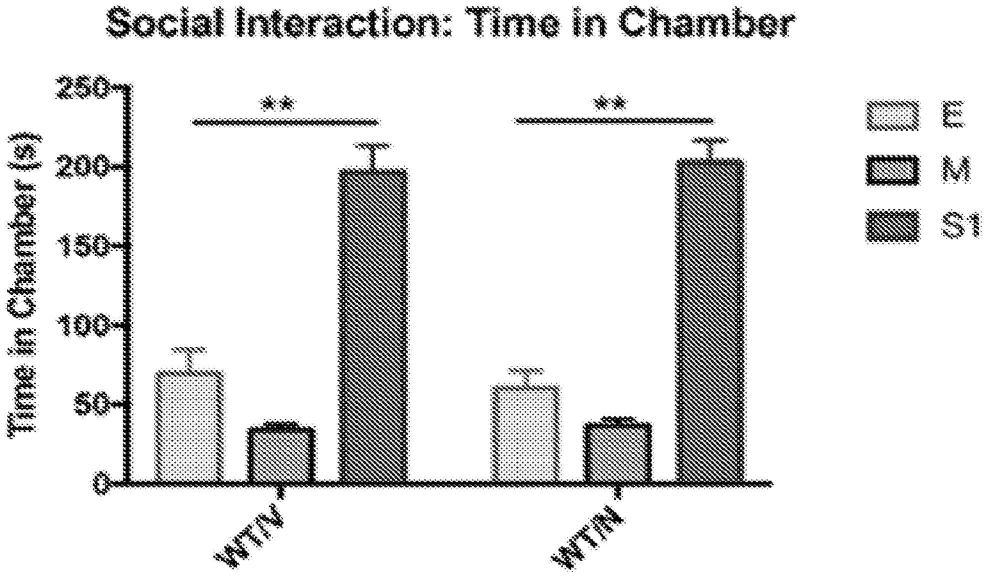
FIG. 13 shows NitroSynapsin (N) treatment did not alter the social behavior of WT mice in the three-chamber assay. Summary graphs showing time in three chambers (FIG. 13A), number of visits (FIG. 13B), and duration of visits (FIG. 13C) by WT mice after 3-month treatment with vehicle (V) or NitroSynapsin (N). NitroSynapsin treatment did not significantly alter the social behavior of WT mice. Data are mean+s.e.m., n=10 each for WT/V and WT/N groups. E: Empty chamber; S1: Stranger mouse 1 chamber. *P<0.05 and **P<0.01, compared to E by ANOVA or t-test.
Figure 13B:
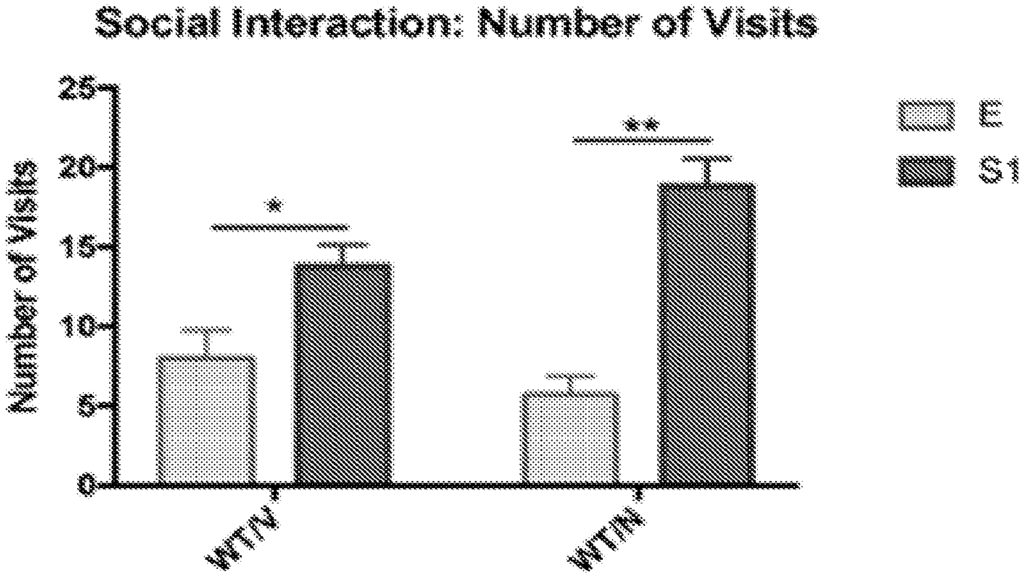
Figure 13C:
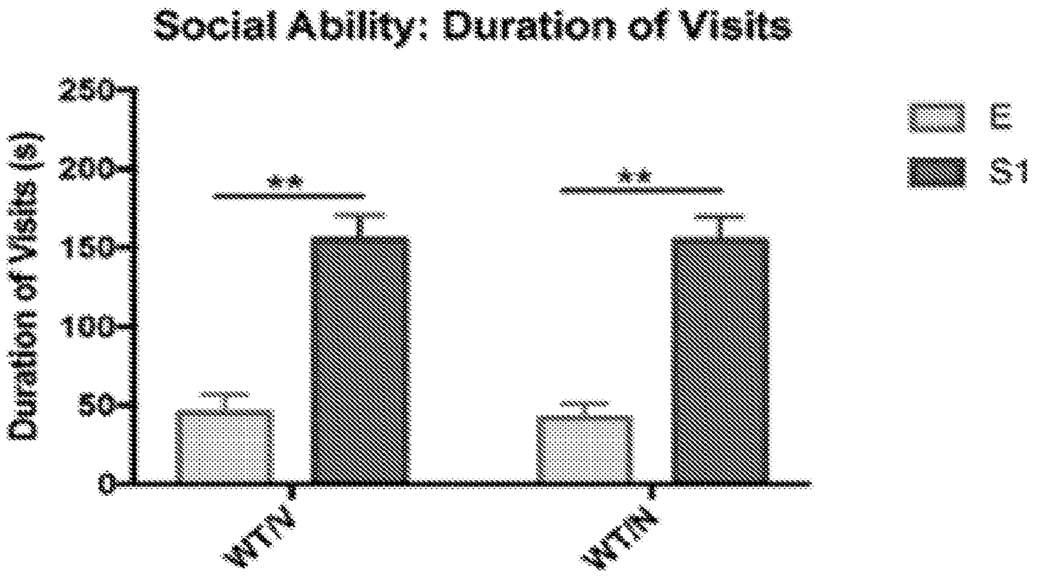

Neurobehavioral tests were used to determine whether treatment of Mef2c-het mice with NitroSynapsin could rescue autistic/MCHS-like behavioral phenotypes. The Morris water maze was first performed to test the effect on spatial learning and memory (FIG. 10A, FIG. 10B). During hidden platform training sessions, vehicle-treated Mef2c-het (Het/V) mice showed impaired spatial learning in the first two days by taking longer to find the hidden platform than vehicle-treated WT (WT/V) mice (FIG. 10A). However, Mef2c-het mice treated with NitroSynapsin (Het/N) showed improved performance relative to vehicle during these tests. This improvement could not be attributed to an increase in swimming speed per se, neither Mef2c heterozygosity nor NitroSynapsin treatment affected swimming speed (FIG. 11). Twenty-four hours after all groups of mice reached the criteria (20 sec to find the hidden platform), probe tests to examine memory retention were performed. As shown in FIG. 10B, WT/V mice displayed normal memory retention by spending a significantly longer time in the target quadrant, where the hidden platform was previously located. In contrast, Het/V mice displayed impaired memory by not showing a preference to the target quadrant over the opposite quadrant. Interestingly, Het/N mice spent significantly more time in the target quadrant than in the opposite quadrant, a sign that NitroSynapsin treatment normalized memory function (FIG. 10A, FIG. 10B). An open field test, a 30-minute test to assay general locomotor activity, was performed next. Het/V mice showed enhanced center activity (FIG. 10C), but not total activity (FIG. 10D). This abnormal behavior was rescued by chronic treatment with NitroSynapsin. The drug also corrected the abnormal repetitive behavior of increased head dipping of Mef2c-het mice in the hole-board exploration test (FIG. 10E). Additionally, a social interaction behavioral test was performed. WT/V mice spent significantly more time in a chamber with a stranger mouse 1 (S1) than in a chamber with a similar but empty cage (FIG. 10E). However, Het/V mice showed no preference for time spent in either chamber (FIG. 10F, FIG. 10G), a sign of impaired social ability. Additionally, Het/V mice paid significantly fewer visits to S1 and for shorter times per visit than WT/V mice (FIG. 10H, FIG. 10I). Treatment with NitroSynapsin improved this abnormal social behavior. Importantly, initial feasibility experiments, in which Mef2c het mice were treated with equimolar memantine or NitroSynapsin in a head-to-head comparison, demonstrated the superiority of NitroSynapsin in these behavioral paradigms (FIG. 12A). In addition, NitroSynapsin treatment did not significantly alter the social behavior of WT mice (FIG. 13).

Figure 14A:
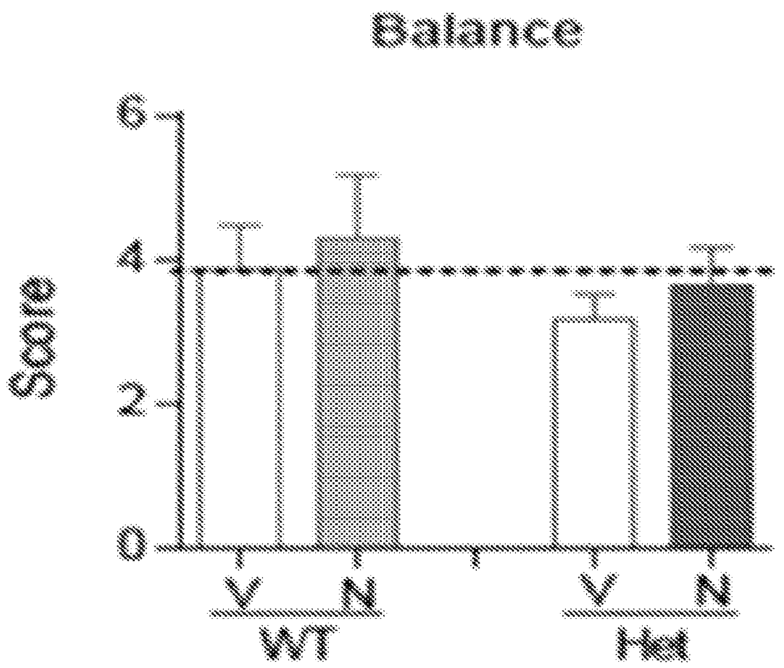
FIG. 14 shows Mef2c-het mice did not exhibit abnormal motor behaviors, except paw clasping, which was not rescued by NitroSynapsin. Summary graphs showing motor behaviors of WT and Mef2c-het mice after 3-month treatment with vehicle (V) or NitroSynapsin (N). Mef2c-het mice did not exhibit significantly altered behaviors on the balance beam (FIG. 14A), cylindrical rod (FIG. 14B), traction capacity (FIG. 14C), suspension test (FIG. 14D), or vertical pole tests (FIG. 14E). In these experiments, treatment with NitroSynapsin had no significant effect on behaviors of either WT or Mef2c-het mice. The abnormal paw clasping activity observed in Mef2c-het mice was not rescued by NitroSynapsin treatment (FIG. 14F). Data are mean+s.e.m., n=12, 5, 11, and 13 for WT/V, WT/N, Het/V, and Het/N groups, respectively. *P<0.05 compared to WT/V by ANOVA.
Figure 14B:
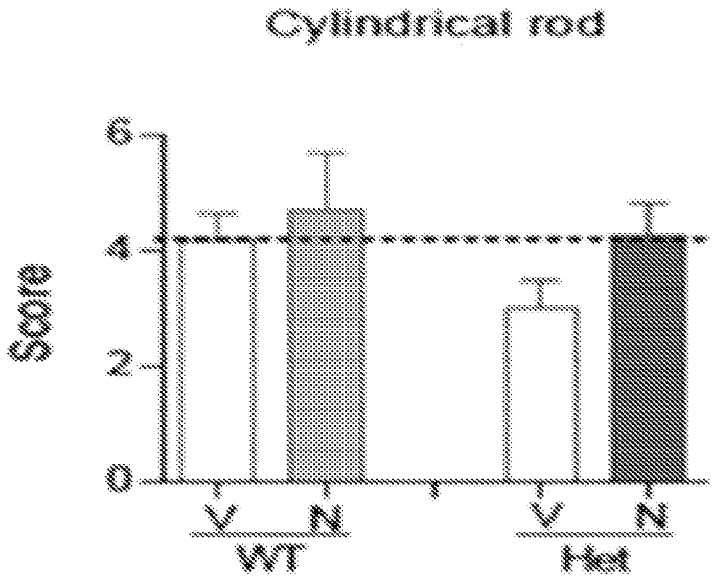
Figure 14C:
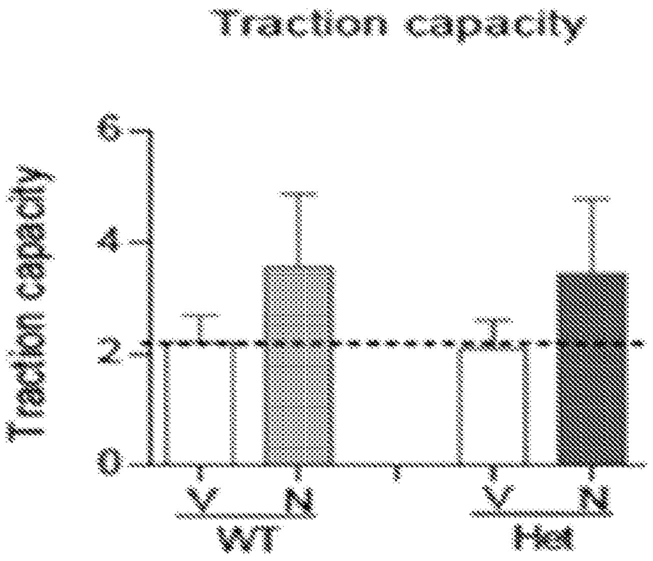
Figure 14D:
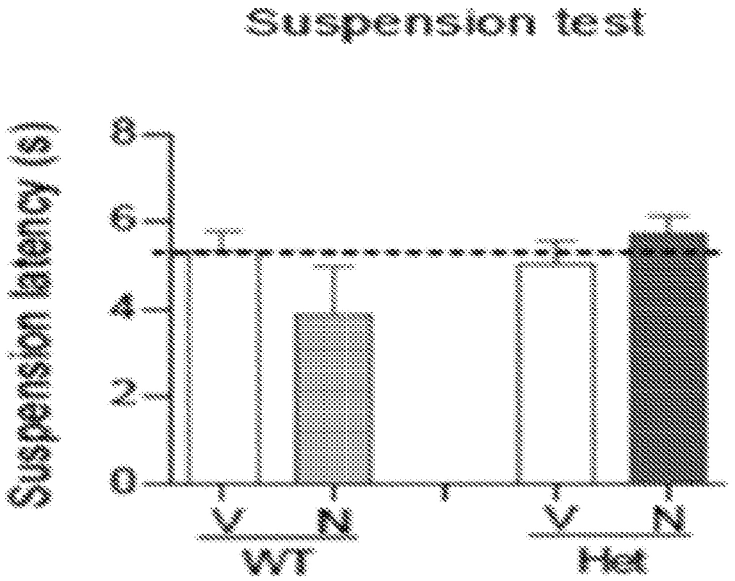
Figure 14E:
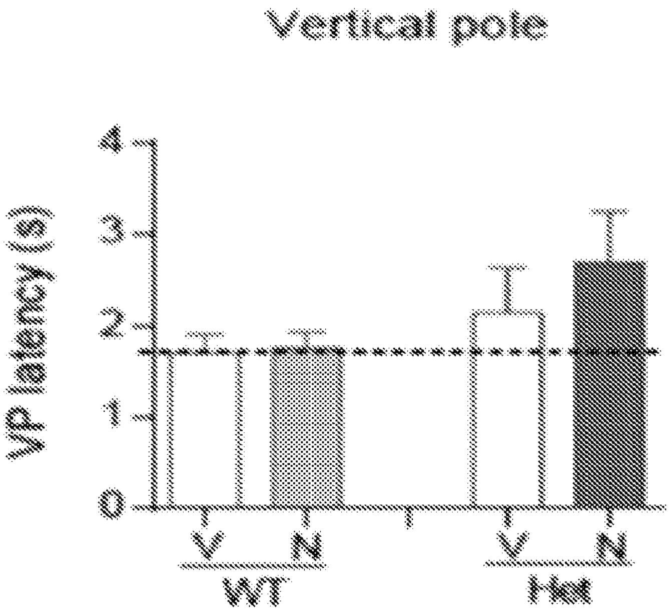
Figure 14F:
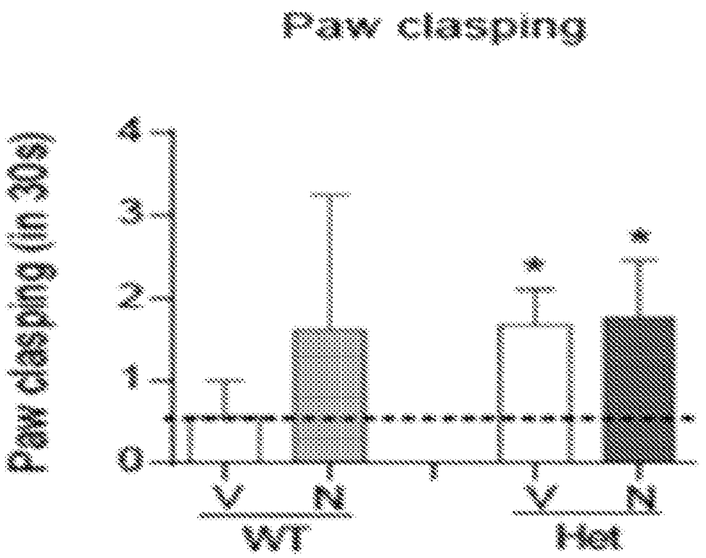

Taken together, these results show that chronic treatment of Mef2c-het mice with NitroSynapsin significantly improved cognitive deficits, repetitive behavior, impaired social interactions, and possibly altered anxiety. Of note, Mef2c-het mice did not exhibit aberrant motor behaviors except for paw clasping (FIG. 14A-E). However, NitroSynapsin treatment did not improve the paw clasping phenotype (FIG. 14F).

Figure 12B:
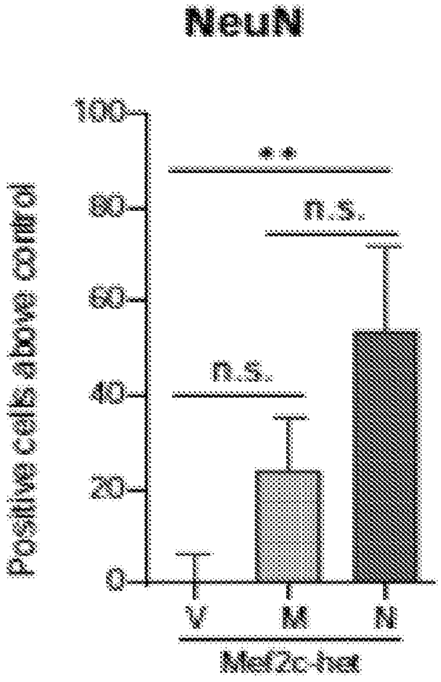
FIG. 12B presents a summary graph showing that the number of hippocampal NeuN+ cells in Mef2c-het mice treated with NitroSynapsin (N), but not memantine (M), was significantly greater than in vehicle (V)-treated mice. Data are mean+s.e.m., n=4-5 per group; **P<0.01 by ANOVA.

Example 5 Beneficial Effects of Nitrosynapsin on Neuronal Cell Loss, Altered E/I Markers, and Impaired LTP in Mef2c-het Mice Immunohistochemistry was performed to determine the effects of drug treatment on neuronal loss and altered expression of VGAT or VGLUT2 in the hippocampus of Mef2c-het mice (FIG. 15A-G). Specifically, monitored by stereology using the optical dissector method, the total number of NeuN+ cells in the hippocampus of Het/N mice was significantly greater than in Het/V mice (FIG. 15B), consistent with the efficacy of NitroSynapsin in the prior behavioral experiments. Additionally, in the initial feasibility experiments, a significantly greater effect of NitroSynapsin over memantine on NeuN+ cell counts was observed (FIG. 12B).

Figure 16A:
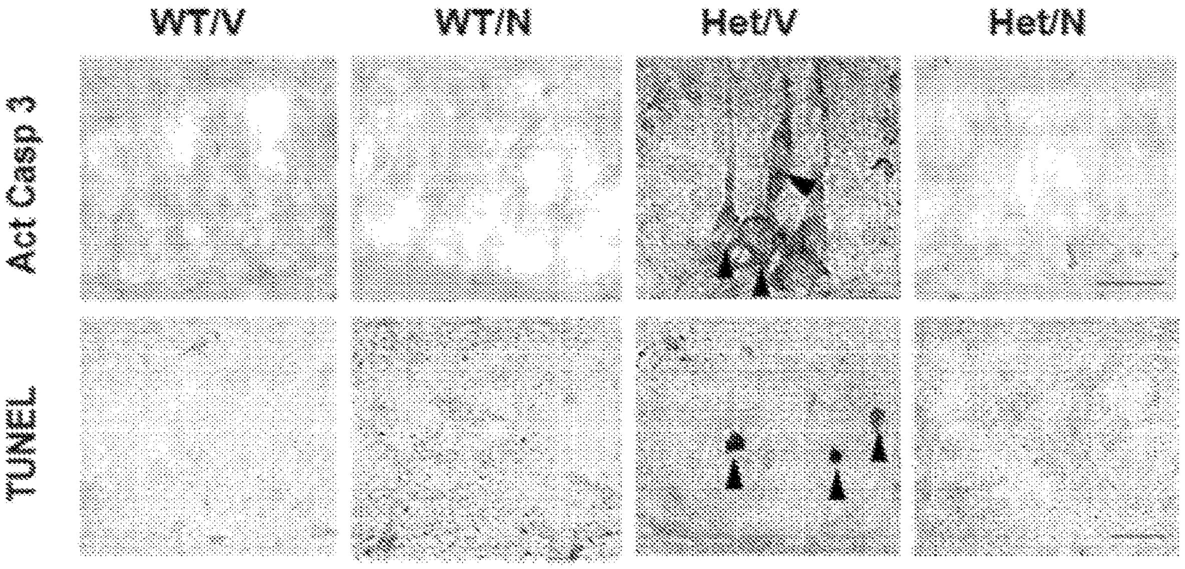
FIG. 16A shows immunohistochemistry of activated caspase-3 (Act Casp 3, top panels) and TUNEL staining (bottom panels) in the hippocampal CA3 region of WT mice treated with vehicle (WT/V) or NitroSynapsin (WT/N), and in Mef2c-het mice treated with vehicle (Het/V) or NitroSynapsin (Het/N). Scale bars, 25 μm.
Figure 16B:
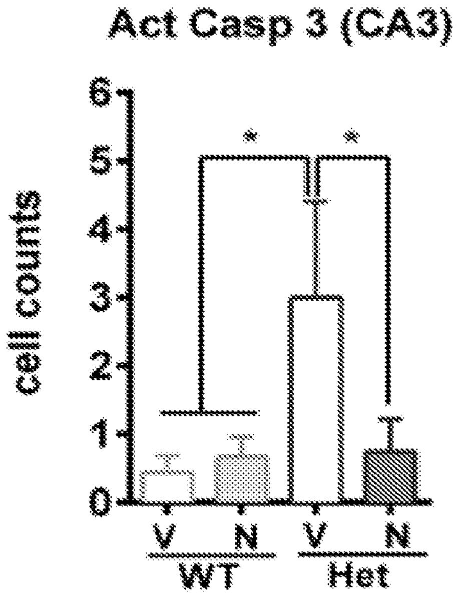
FIG. 16B and FIG. 16C present histograms showing that caspase-3+(FIG. 16B) and TUNEL+ neurons (FIG. 16C) were significantly increased in Het/V mice compared to control WT/V mice. Furthermore, both of these phenotypes were ameliorated in Het/N mice. Data are mean+s.e.m., n=4-5 per group; *P<0.05, by ANOVA.
Figure 16C:
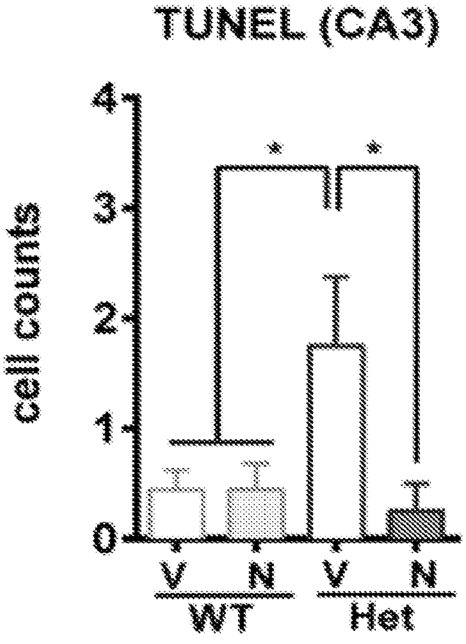
Figure 17A:
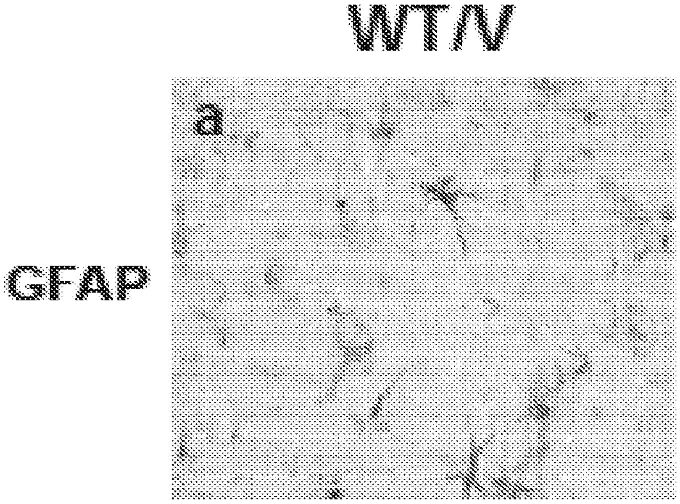
FIG. 17A-C present representative images showing increased GFAP+ cells with morphology of astrocytes in Mef2c-het mice vs. WT (FIG. 17B vs.
Figure 17B:
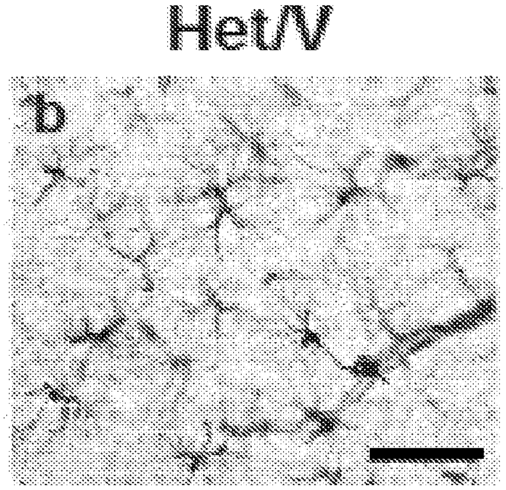
Figure 17C:
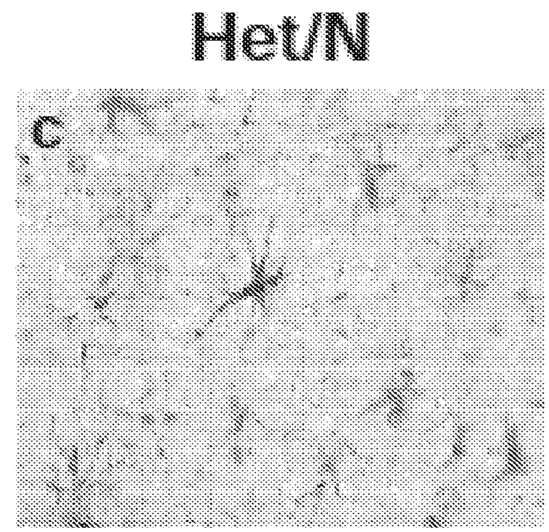
Figure 17D:
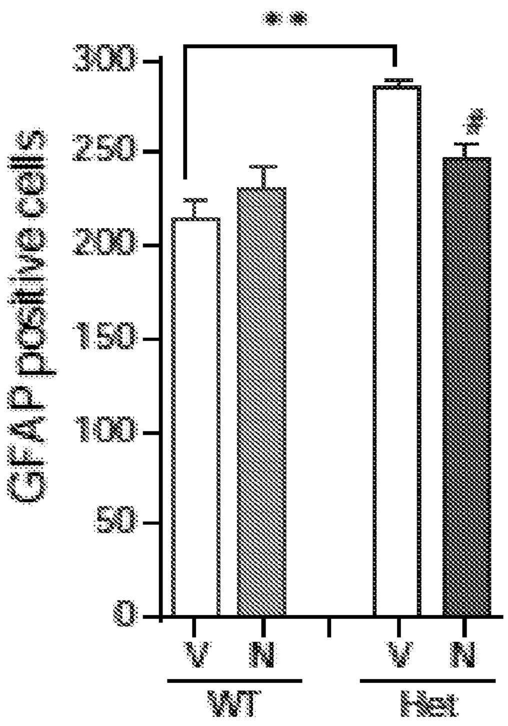
(FIG. 17D) Quantification of GFAP+ cells in the hippocampus of WT and Mef2c-het mice treated with vehicle (V) or NitroSynapsin (N). Data are mean+s.e.m., n=4 or 5 per group; **P<0.01 compared to WT/V and #P<0.05 compared to Het/V by ANOVA.

The reduction in NeuN+ cells in Mef2c-het mice could be accounted for at least in part by apoptotic cell loss because the number of neurons staining for active caspase-3 and for terminal deoxynucleotidyl transferase dUTP nick end labeling (TUNEL) in the CA3 region of the hippocampus was significantly increased in Mef2c-het mice compared to WT ($P<0.012$, FIG. 16). Moreover, while the number of activated caspase 3-positive and TUNEL-positive cells was increased in Het/V, it was reduced back to normal in Het/N mice (FIG. 16). This result was consistent with the notion that apoptotic neurons observed in Mef2c-het mice were significantly rescued by NitroSynapsin. Moreover, treatment with NitroSynapsin also normalized the number of GFAP+ cells with astrocytic morphology in Mef2c-het mice (FIG. 17).

Figure 15A:
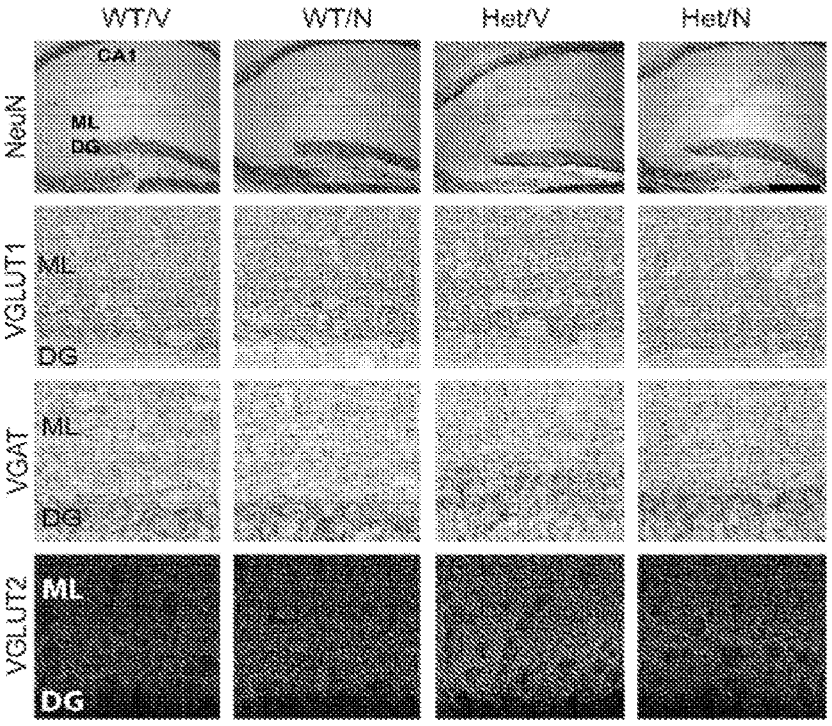
FIG. 15A shows immunohistochemical images of NeuN, VGLUT1, VGAT, and VGLUT2 in the molecular layer (ML) of the hippocampal dentate gyms (DG) of WT and Mef2c-het mice treated with vehicle (V) or NitroSynapsin (N). Scale bars: 500 μm (top panel), 25 μm (middle panels), 40 μm (bottom panel).
Figure 15B:
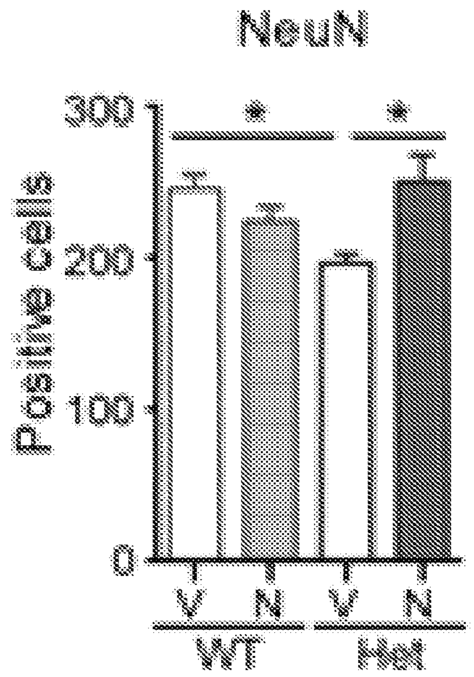
FIG. 15B-F presents summary graphs showing rescue by NitroSynapsin of decreased number of total NeuN+ cell counts (FIG. 15B), reduced immunoreactivity of VGAT (FIG. 15D) and VGLUT2 (FIG. 15F), and increased ratio of VGLUT1/VGAT (e) or VGLUT2/VGAT (FIG. 15G) in the hippocampus of Mef2c-het mice.
Figure 15C:
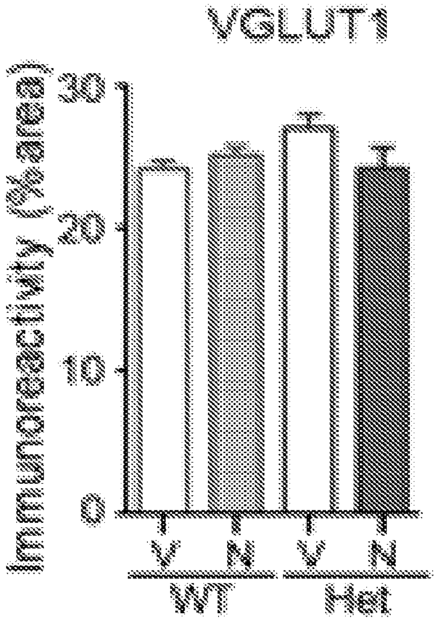
Figure 15D:
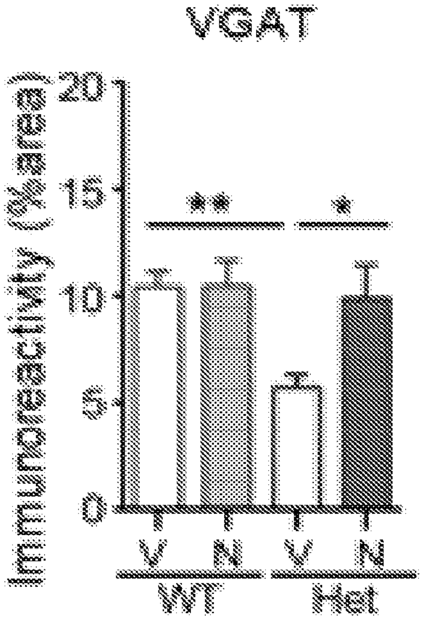
Figure 15E:
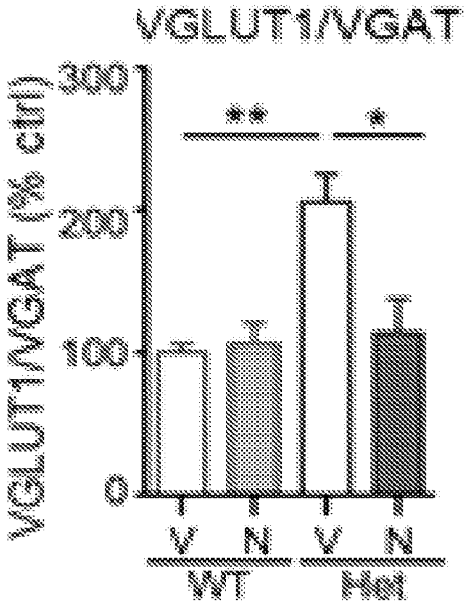
Figure 15F:
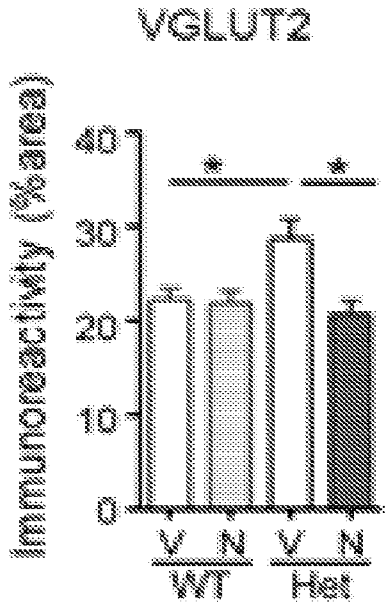
Figure 15G:
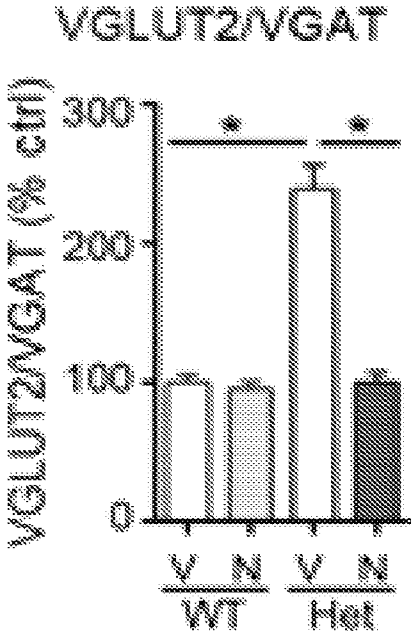
FIG. 15 shows NitroSynapsin rescued abnormal neuronal and synaptic properties in Mef2c-het mice.
FIG. 15H shows impaired LTP in Mef2c-het mice was also rescued by NitroSynapsin. Data are mean±s.e.m., n=4-5 per group in FIGS. 15A-G and 7-9 in FIG. 15H. *P<0.05, **P<0.01, by ANOVA.
Figure 15H:
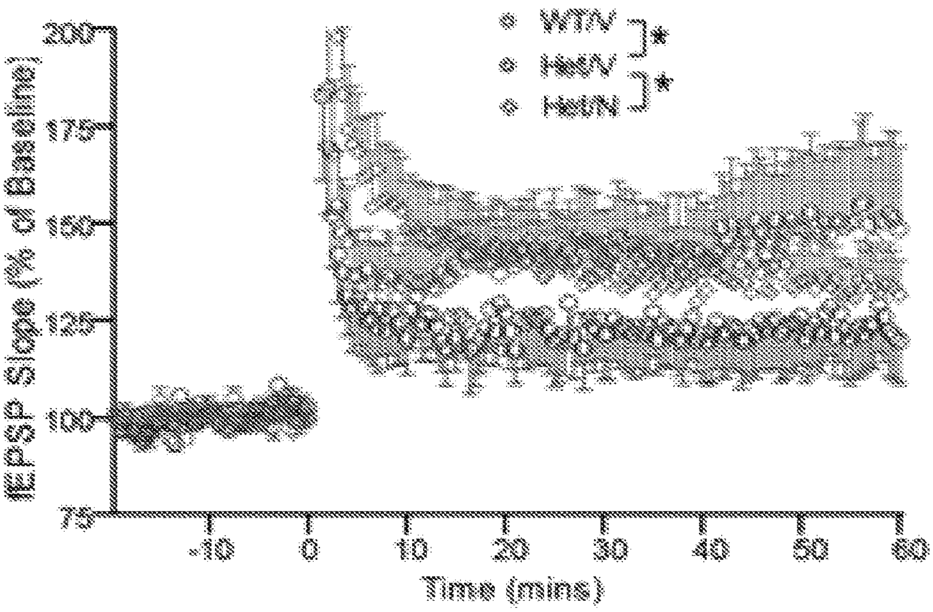
Figure 18A:
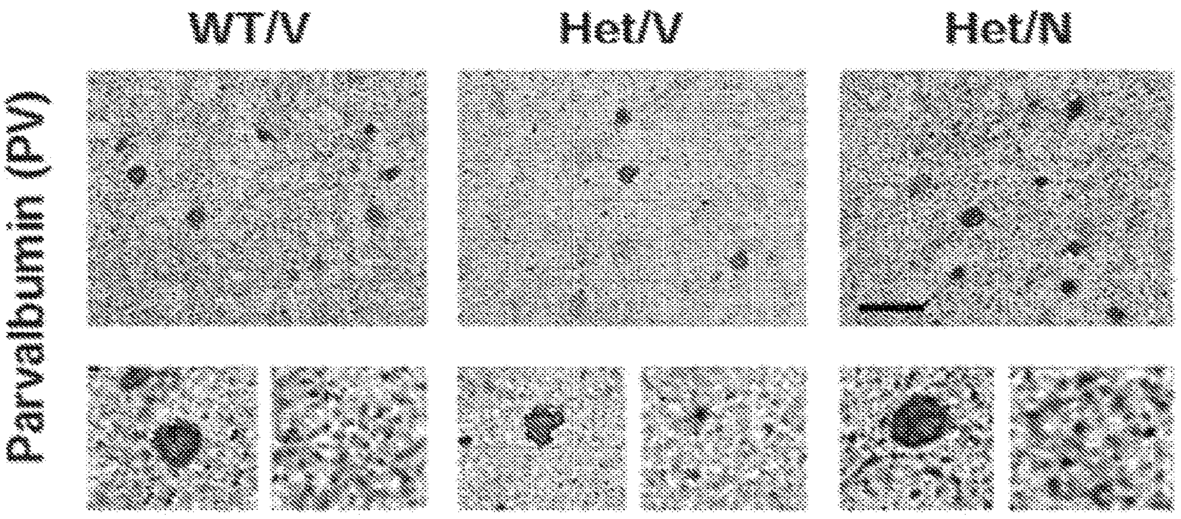
FIG. 18A presents representative images showing PV+ immunoreactivity in the hippocampus of WT mice treated with vehicle (WT/V) and in Mef2c-het mice treated with vehicle (Het/V) or NitroSynapsin (Het/N). Higher magnification of PV+ neurons (bottom left of each panel) or synapses (bottom right of each panel). Scale bar, 25 μm.
Figure 18B:
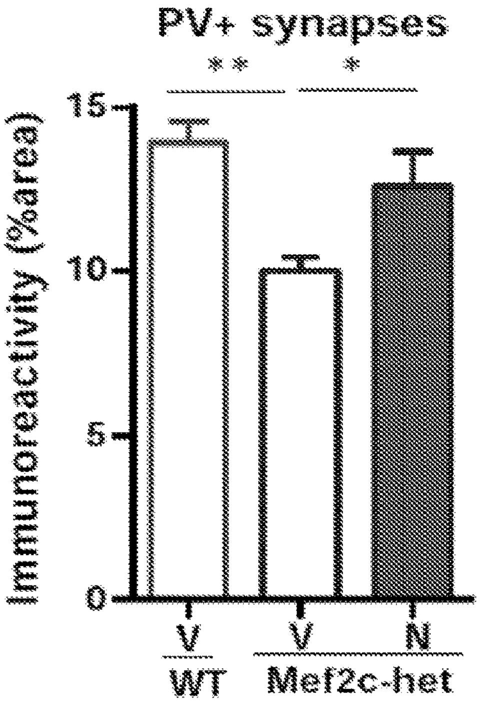
FIG. 18B presents a histogram showing reduction in PV-immunoreactive synapses in Het/V mice compared to WT/V mice. This reduction was significantly ameliorated after NitroSynapsin treatment.
Figure 18C:
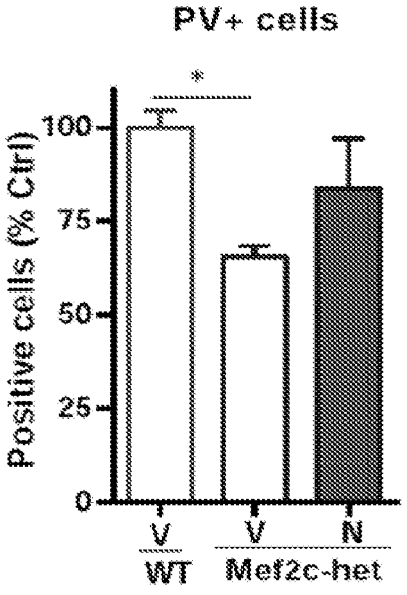
FIG. 18C presents a histogram showing reduction in the number of PV-immunoreactive cells in Het/V mice but not in Het/N mice compared to WT/V mice. Data are mean+s.e.m., n=4-5 per group; *P<0.05, **P<0.01 by ANOVA.
Figure 19:
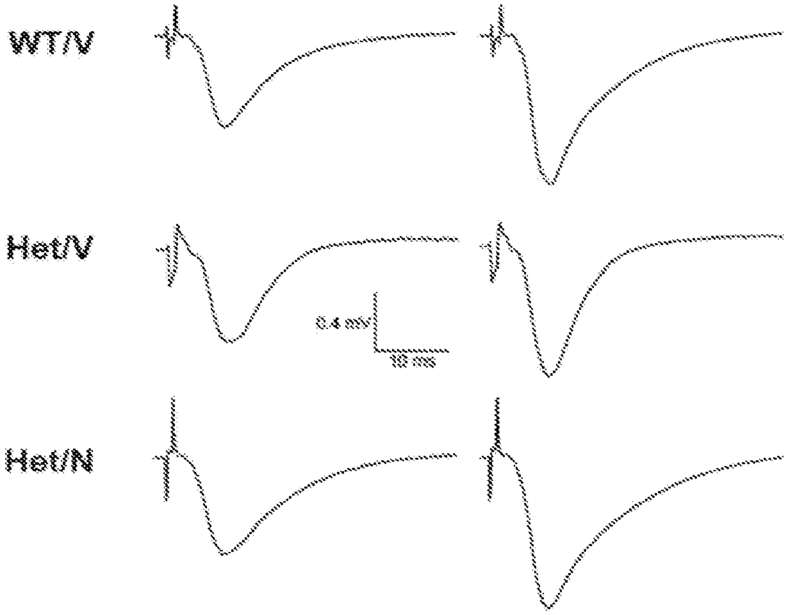
FIG. 19 shows NitroSynapsin treatment rescued deficits in LTP in Mef2c-het mice. Representative traces of evoked currents before (left) and after (right) induction of hippocampal LTP in slices prepared from WT/V-, Het/V-, and Het/N-treated mice. fEPSP slopes for each group of animals is presented in FIG. 15H in the text.

The effect of NitroSynapsin on altered expression of E/I markers in Mef2c-het mice was determined by quantitative confocal immunohistochemistry. While the level of VGLUT1 immunoreactivity was unaltered by NitroSynapsin treatment, VGAT and VGLUT2 levels as well as the ratio of VGLUT1/VGAT or VGLUT2/VGAT were normalized by NitroSynapsin treatment in Mef2c-het mice (FIG. 15C-G). The numbers of both parvalbumin (PV)-expressing basket-interneurons and PV-positive synapses were significantly reduced in Mef2c-het mice (FIG. 18), while NitroSynapsin significantly increased PV+ synapses (% area) (FIG. 18). These results suggest that NitroSynapsin restores E/I balance in Mef2c-het mice. Finally, chronic treatment with NitroSynapsin also significantly rescued impaired hippocampal LTP in the Mef2c-het mice (FIG. 15H, FIG. 19).

As summarized in FIG. 1, Mef2c-het mice displayed MCHS-like behavioral deficits and thus represented a model for studying disease pathophysiology. Mef2c-het mice showed reduced viability, the cause of which is currently unknown. The Mef2c-het mice that survived to adulthood exhibit a reduced number of neurons and synaptic impairment, specifically E/I imbalance caused by reduced inhibitory and enhanced excitatory neurotransmission. Remarkably, treatment of Mef2c-het mice with the new, improved NMDAR antagonist NitroSynapsin not only corrected E/I imbalance, but also improved autistic/MCHS-like behavioral deficits, thus providing target validation and potential disease treatment.

The results provided herein showed that VGAT was significantly reduced in Mef2c-het mouse hippocampus. In accord with this finding, functional inhibitory synaptic transmission was reduced, as demonstrated in recordings of spontaneous mIPSCs. Additionally, VGLUT2 was aberrantly upregulated, consistent with an increase in excitatory neurotransmission, as documented by increased mEPSC frequency. Consequently, dysfunctional inhibitory and excitatory neurotransmission contribute to E/I imbalance in the hippocampus of Mef2c-het mice. Remarkably, NitroSynapsin significantly improved all three parameters in Mef2c-het mice, with increases in synaptic markers, LTP, and neuronal number. Most importantly, NitroSynapsin significantly improved autistic/MCHS-like behaviors in Mef2c-het mice.

Example 6 Beneficial Effects of NitroSynapsin in the TSC+/− Mouse Model of Tuberous Sclerosis Tuberous sclerosis complex (TSC) is an autosomal dominant disorder manifested by intellectual disability, epilepsy/electrophysiological deficits, and neurobehavioral abnormalities, often producing features of autism spectrum disorder (ASD). The disorder is caused by heterozygous mutations that inactivate one of two genes, Tsc1 or Tsc2. The TSC proteins form the TSC1/2 complex, which inhibits Rheb, a GTPase which activates mammalian target of rapamycin complex 1 (mTORC1). mTORC1 stimulates mRNA translation and cell growth; excessive activation of this pathway due to the inactive TSC1/2 complex may lead to TSC pathological features, such as abnormal signaling at synapses and aberrant subunit composition of AMPA receptors in a variety of neuronal types. One important etiological pathway involves overstimulation of mTOR. Hyperactivation of mTOR in TSC results in inhibition of macroautophagy, with consequent loss of synaptic spines and behavioral abnormalities; inhibition of mTOR with rapamycin can rescue these phenotypes.

Figure 20A:
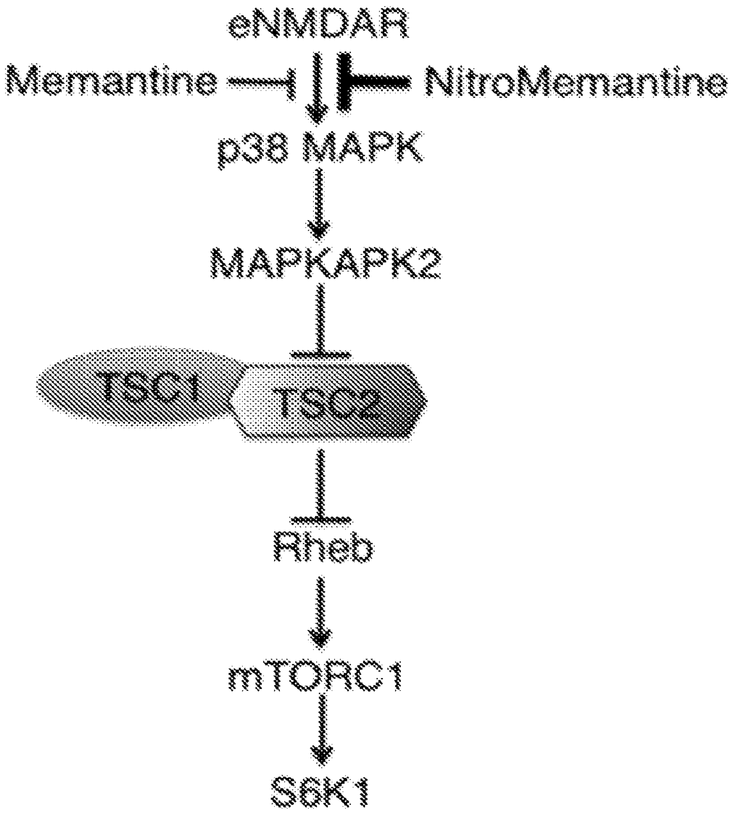
FIG. 20A shows extrasynaptic N-methyl-D-aspartate receptor (eNMDAR) activity triggered signaling that inactivated Tuberous Sclerosis Complex 2 (TSC2) and was attenuated by the NMDAR antagonist NitroMemantine (aka NitroSynapsin, YQW-036, NMI-6979) to a greater degree than Memantine. Schema shows that NMDA receptor antagonists blocked activation of the p38 MAPK cascade. NitroMemantine YQW-036 (also known as NitroSynapsin) is a more effective antagonist than Memantine, and therefore exerted an even larger beneficial effect (hence, the larger inhibitor symbol).
Figure 20B:
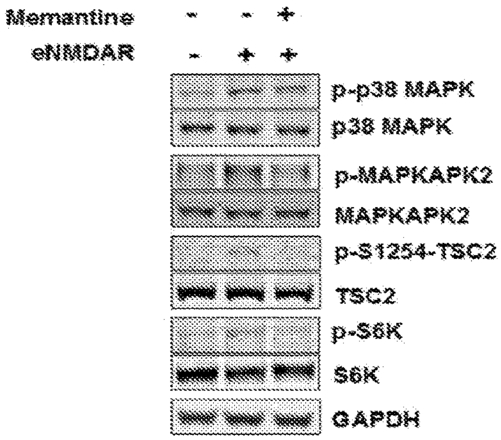
FIG. 20B shows Western blots evidence that eNMDAR stimulation increased phosphorylation/activation of the p38 MAPK/MAPKAPK2/TSC2/mTORC1/S6K1 cascade. Blockade of eNMDARs with the eNMDAR antagonist memantine (10 μM) reduced this signaling. This experiment was replicated 4 times with similar results and quantified in FIG. 20C.
Figure 20C:
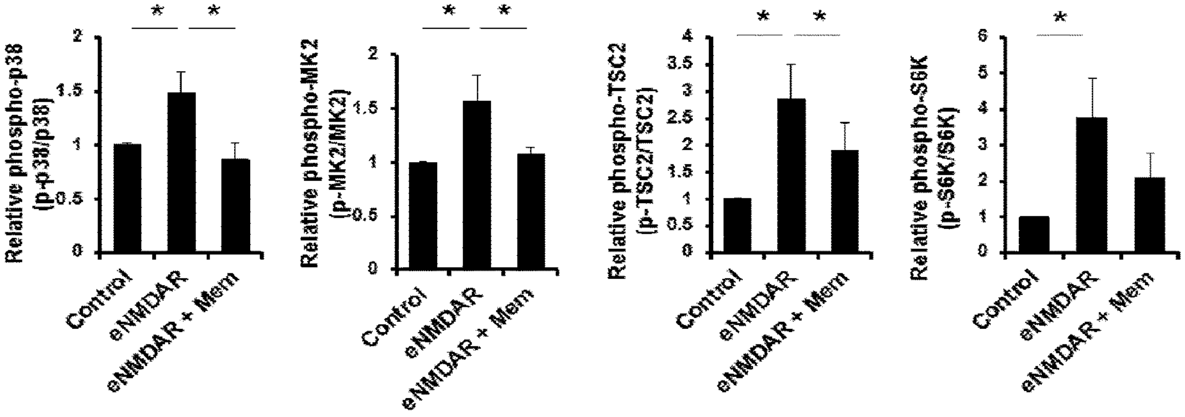
FIG. 20C shows quantification of immunoblots by unpaired t-test; mean±s.e.m., n=4, *P<0.05 (Mem, memantine).

In this example, it was found that antagonists that preferentially block tonic activity at eNMDARs, particularly the newer drug NitroSynapsin, provide biological and statistically significant improvement in $Tsc2^{+/-}$ (het) mouse phenotypes. In these studies, the $Tsc2^{+/-}$ mouse model of tuberous sclerosis was used. Accompanying this improvement was correction of activity in the p38 MAPK-TSC-Rheb-mTORC1-S6K1 pathway (FIG. 20). Deficits in hippocampal long-term potentiation (LTP), histological loss of synapses, and behavioral fear conditioning in $Tsc2^{+/-}$ mice were all improved after treatment with NitroSynapsin. Taken together, these results suggest that amelioration of excitatory/inhibitory (E/I) imbalance, by limiting excessive eNMDAR activity, may represent a novel treatment approach for TSC.

Figure 21A:
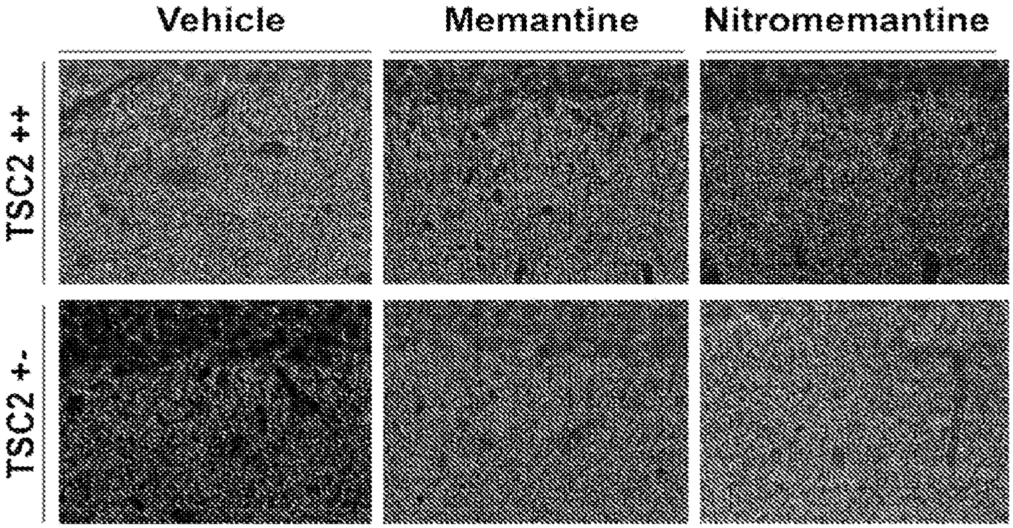
FIG. 21A shows representative histological images of brain slices from three-month-old WT and $Tsc2^{+/-}$ transgenic mice treated with vehicle, M or N. Staining for SY38 (synpatophysin)-positive synaptic terminals (red) are shown in the hippocampus.
Figure 21B:
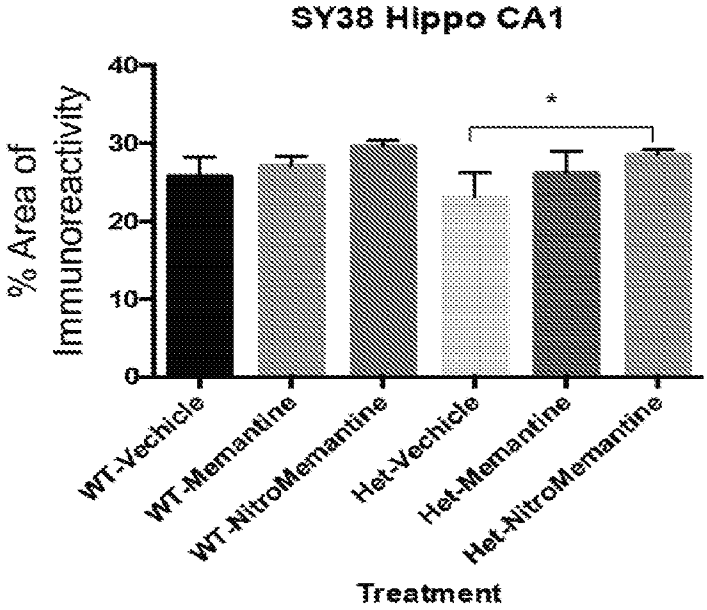
FIG. 21B shows quantification of immunoreactivity of Synaptophysin in WT and TSC2+/− transgenic mice with vehicle, M or N treatment. Synaptic integrity was measured as the percent area of occupied by immunoreactive SY38. Treatment $Tsc2^{+/-}$ mice with N raised the synaptic signal to WT levels and was significantly greater than for vehicle treated. Values presented as % area+s.e.m., *P<0.5 by t test, n=3 mice per treatment group.
Figure 22A:
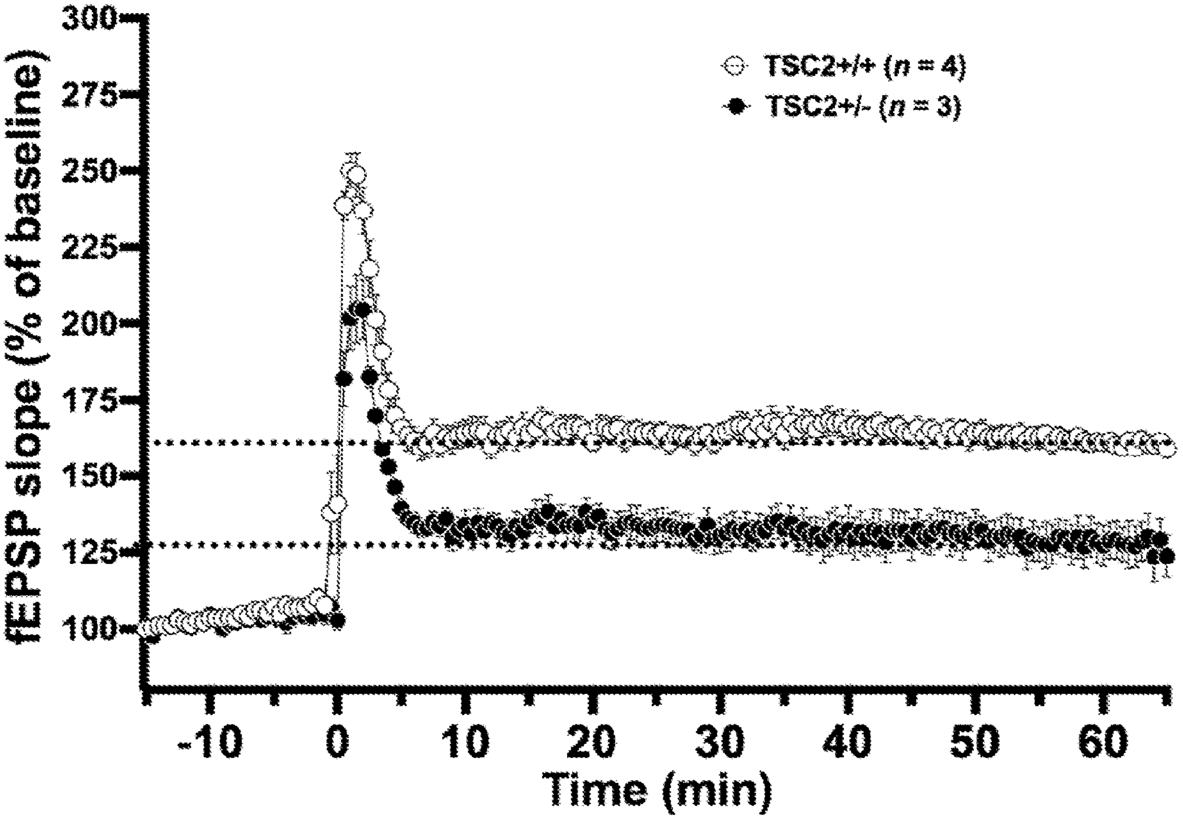
FIG. 22A shows LTP (long-term potentiation) recorded from hippocampal slices by multielectrode array (MEA). fEPSP slope is plotted every 30 s and represents mean±s.e.m. for $Tsc2^{+/+}$ and $Tsc2^{+/-}$ (n=7 slices from 7 mice).
Figure 22B:
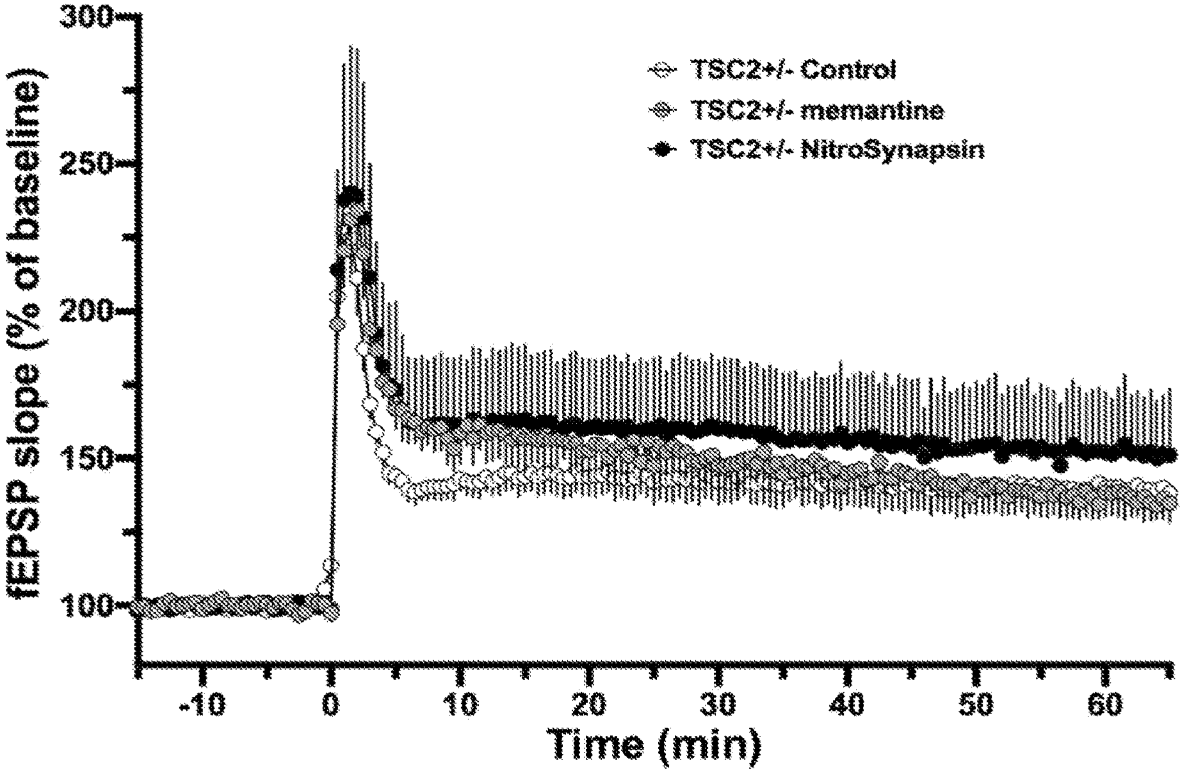
FIG. 22B shows effects of treatment with vehicle control vs. 1-2 μM memantine or NitroSynapsin on $Tsc^{+/-}$ mice (n=13 slices from 13 mice, P<0.001 for improvement of LTP by NitroSynapsin (but not memantine) monitored 55-65 min after induction).
Figure 23:
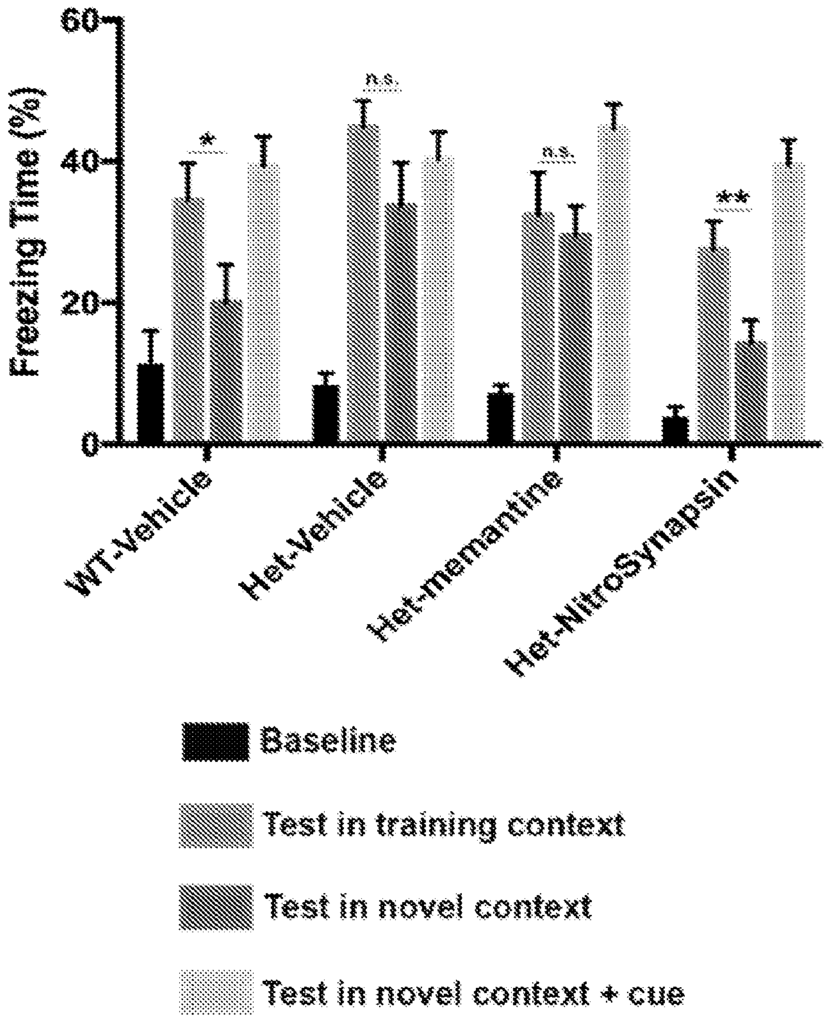
FIG. 23 shows beneficial effects of treatment with NitroSynapsin but not memantine on context discrimination in $Tsc2^{+/-}$ (het) mice assessed by the fear conditioning test. Freezing time of three-month-old WT and $Tsc2^{+/-}$ transgenic mice treated with vehicle, memantine or NitroSynapsin in fear-conditioning trials. All four groups of mice tested (WT-vehicle, Het-vehicle, Het-memantine, and Het-NitroSynapsin) showed freezing in the “training context” and the “novel context+cue,” indicating that their conditioned fear responses were unaffected by genotype or drugs. Additionally, WT mice displayed context discrimination between the training and novel contexts (*P=0.032). In contrast, vehicle- or memantine-treated $Tsc2^{+/-}$ mice showed deficits in this behavior, resulting in the lack of discrimination between the training and novel contexts (n.s.=no significant difference). NitroSynapsin (but not memantine) treatment improved this phenotype, normalizing context discrimination in $Tsc2^{+/-}$ mice (**P=0.023). Values are mean+s.e.m. (n=7-12 mice per group).

NitroSynapsin Reverses Deficits in Long-Term Hippocampal Plasticity in Tsc2 Heterozygous Mice Long-term potentiation (LTP), a form of synaptic plasticity elicited in response to excitatory input and thought to represent an electrical correlate of learning and memory in the hippocampus, was examined. Field recordings in the CA1 region of hippocampal slices were used to investigate the effects of Tsc2 mutation on this form of synaptic plasticity. For this purpose, acute hippocampal slices from one-month-old mice were prepared and field recordings in a microelectrode array (MEA) chamber perfused with artificial cerebrospinal fluid (ACSF) were performed. fEPSPs (field excitatory postsynaptic potentials) were recorded in the CA1 region after evoking LTP via stimulation of the Schaffer collaterals (four repetitions of 100 Hz pulses for one second each). The initial slope of the fEPSP was analyzed to assess LTP. However, with a stronger induction protocol as used here, we observed a decrease in LTP, monitored 60 min after induction. Strikingly, we found that a 4-hour treatment with 1-2 μM of the more efficacious eNNIDAR antagonist NitroSynapsin, but not memantine, improved LTP in Tsc2+'-mice compared to vehicle control treatment (P<0.001 at 55-65 min). As shown in FIGS. 21-23, NitroSynapsin (aka NitroMemantine) protected synapses, long term potentiation (LTP), and neurobehavior in the tuberous sclerosis complex (TSC) het model of ADD/IDD to a significantly better degree than memantine.

NitroSynapsin Treatment of Tsc2 Heterozygous Mice Reduces Synaptic Loss

To determine the effects of eNMDAR antagonists on the brain histology of $Tsc2^{+/-}$ mice, quantitative confocal immunohistochemistry was used to analyze coronal brain slices from 3-month-old wild-type (WT) and $Tsc2^{+/-}$ mice that had been treated for two and a half days with vehicle, memantine or NitroSynapsin. Tsc2+/− mice on the C57B1/6J background received via the intraperitoneal route either vehicle or a loading dose of 92 μmol/kg of memantine or NitroSynapsin, followed by 4.6 μmol/kg of drug twice daily for two-and-a-half-days, with the last dose 3 hours prior to the behavioral training session (for a total of five drug injections). This dosing regimen yields an effective concentration of drug at NMDARs in the brain of 1-10 μM.

A key feature of TSC is thought to involve loss of synapses. Importantly, $Tsc2^{+/-}$ mice treated with NitroSynapsin (NitroMemantine) manifested significantly more staining for the presynaptic marker synaptophysin (SY38) in the hippocampus than untreated heterozygous littermates, whereas the effect of memantine was not statistically significant (see FIGS. 21A and 21B).

Additional marker analysis included glial fibrillary acidic protein (GFAP, an astrocytic marker under these conditions), NeuN (a neuronal nuclei and cell body marker), and microtubule-associated protein 2 (MAP2, labeling neuronal dendritic spines). Confocal immunohistochemical images of the hippocampus revealed no difference in expression between NeuN, MAP2, or GFAP in WT vs. $Tsc2^{+/-}$ mice. Collectively, these histological results indicate that there was no significant loss of neurons/neuropil or increase in reactive astrocytosis at this stage of the disease in the hippocampus, in contradistinction to the loss of synapses.

NitroSynapsin Improves Neurobehavioral Phenotypes in Tsc2 Heterozygous Mice

Fear conditioning tests were performed on three-month-old $Tsc2^{+/+}$ and $Tsc2^{+/-}$ mice to explore the effects of eNMDAR antagonists on anxiety, and learning and memory deficits in $Tsc2^{+/-}$ mice. Vehicle, memantine or NitroSynapsin were administered for two and a half days, with the last dose of drug occurring 3-hours prior to the first training session. On the fear conditioning test (see FIG. 23), WT littermate mice exhibited a significantly increased amount of freezing time in the training context over the novel context (P=0.032), indicating that these animals could discriminate between the two conditions. FIG. 23 shows effects of treatment with memantine or NitroSynapsin on context discrimination in Tsc2+/− mice assessed by the fear conditioning test. Freezing time of three-month-old WT and $Tsc2^{+/-}$ transgenic mice treated with vehicle, memantine or NitroSynapsin in fear-conditioning trials. All four groups of mice tested (WT-vehicle, Het-vehicle, Het-memantine, and Het-NitroSynapsin) showed freezing in the "training context" and the "novel context+cue," indicating that their conditioned fear responses were unaffected by genotype or drugs. Additionally, WT mice displayed context discrimination between the training and novel contexts (*P=0.032). In contrast, vehicle- or memantine-treated $Tsc2^{+/-}$ mice showed deficits in this behavior, resulting in the lack of discrimination between the training and novel contexts (n.s.=no significant difference). NitroSynapsin treatment improved this phenotype, normalizing context discrimination in $Tsc2^{+/-}$ mice (**P=0.023). Values are mean+s.e.m. (n=7-12 mice per group). Abbreviations: Training context=training environment in which the mice were previously trained with a shock preceded by a sound cue. Novel context=new flooring and walls in the test chamber. Novel context+cue=novel context with sound cue.

In contrast, $Tsc2^{+/-}$ (het) mice were deficient in this form of context discrimination. Remarkably, while memantine failed to mitigate this deficit, NitroSynapsin improved the ability to discriminate context in $Tsc2^{+/-}$ mice to normal WT levels (P=0.023). As a control, all four groups of mice tested (WT-vehicle, Het-vehicle, Het-memantine, and Het-NitroSynapsin) displayed freezing to the conditioned cue in the novel context, indicating that hippocampal-independent fear responses were unaffected by genotype or drugs.

In summary, short-term (4 hour) application of the new, improved drug NitroSynapsin, but not memantine, was able to reverse deficits in synaptic plasticity, as monitored approximately one hour after induction of LTP in CA1 hippocampus. Importantly, a two-and-a-half-day treatment with NitroSynapsin reversed the synaptic loss observed in the hippocampus of $Tsc2^{+/-}$ mice as monitored by synaptophysin staining. As little as a two-and-a-half-day treatment with NitroSynapsin, but not with memantine, normalized context discrimination in the $Tsc2^{+/-}$ mice. NitroSynapsin offered significant benefit over memantine in an electrophysiological readout of synaptic plasticity, in neurohistological analysis of synapses, and in neurobehavioral assessments of anxiety and memory. These results suggest that NitroSynapsin should be tested as a potential therapeutic for the neurological aspects of TSC in an effort to improve quality of life.

Figure 24:
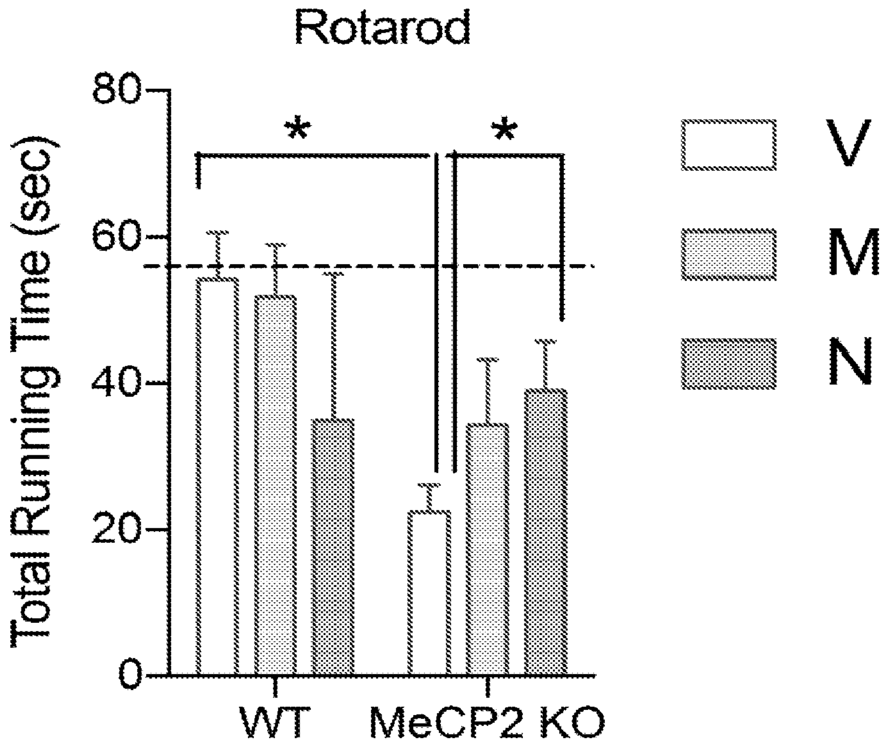
FIG. 24 shows improved rotarod performance of MeCP2 knockout (KO) mouse model of Rett syndrome by treatment with NitroSynapsin. Mice were placed on the stationary cylinder and the cylinder then slowly accelerated to 10 revolutions/min. The total time at 10 rpm before a fall from the cylinder was recorded. V=vehicle treatment (n=12 for WT and n=7 for MeCP2 KO mice; M=memantine treatment (n=16 for WT and n=13 for MeCP2 KO; N=NitroSynapsin treatment (n=5 for WT and n=14 for MeCP2 KO). Values are +s.e.m.; *P<0.05. Treatment with N but not M exerted a significantly improved motor performance on this rotarod test.

Example 7 Beneficial Effects of NitroSynapsin in the MeCP2 Null Mouse Model of Rett Syndrome As shown in FIG. 24, NitroSynapsin improved motor behavior (on the rotarod test, which is well known to one skilled in the art)) in the MeCP2 knockout (KO) mouse model of Rett syndrome, another type of ADD/IDD.

The present application demonstrates that Mef2c-het mice are a useful model for human MCHS; E/I imbalance may play a role in the pathogenesis of MCHS. Restoring synaptic plasticity and preventing neuronal loss with an appropriate NMDAR antagonist rescued or ameliorated autistic/MCHS-like phenotypes in Mef2c-het mice. The results herein describe treatment of human MCHS and other forms of ASD, IDD, and epilepsy (for example, TSC and Rett Syndrome as shown here) by administration of NitroSynapsin (also known as NitroMemantine YQW-036 or NMI-6979, see Structure 1).

Example 8. Methods

Examples 1-7 employed the following methods as described. A person skilled in the art understands that the following descriptions are exemplary and that there are inconsequential variations that could be made while obtaining the same or similar results in Examples 1-7.

Mice, Drug Treatments, and Behavioral Tests

Mef2c heterozygous knockout (Mef2c-het) mice were created by crossing mice carrying the conventional exon 2-deleted allele of Mef2c (Mef2c$^{\Delta 2}$) with their WT littermates. All procedures for maintaining and using these mice were approved by the Institutional Animal Care and Use Committee (IACUC) at the Sanford Burnham Prebys Medical Discovery Institute. In this study, only male mice were used for the behavioral assays to insure uniformity (either with or without drug treatment). Chronic treatment with memantine, NitroSynapsin (both at 4.6 μmol/kg body weight) or vehicle (PBS) was administered via i.p. injection, twice a day for at least 3 months, starting at ~2.5 weeks of age. This age was chosen because mice are still juveniles and thus treatment could begin in human at an equivalent stage. This dose and duration of drug treatment was chosen based on previous studies in which NitroSynapsin exhibited significant protective effects on neurons and synapses.

Mice were randomly distributed to memantine, NitroSynapsin, or vehicle groups before being genotyped. Laboratory workers performing the i.p. injections and behavioral tests were blinded to genotypes. After behavioral tests, mice were used for either immunohistochemistry or electrophysiology, as described below, and studied in a blinded fashion.

Locomotor Activity

Locomotor activity was measured in polycarbonate cages (42×22×20 cm) placed into frames (25.5×47 cm) mounted with two levels of photocell beams at 2 and 7 cm above the bottom of the cage (San Diego Instruments, San Diego, CA). These two sets of beams allowed recording of both horizontal (locomotion) and vertical (rearing) behavior. A thin layer of bedding material was applied to the bottom of the cage. Mice were tested for 30 or 120 min depending on the exact test.

Paw Clasping

For the paw clasping test, mice were picked up by the distal third of their tails and observed for 10 sec. They were rated in a blinded fashion with regard to genotype based on clasping of the front and/or back paws: 0—no paw clasping, 1—occasional clasping of front paws, and 3—constant clasping of front paws and occasional clasping of back paws.

Barnes Maze

The Barnes maze consisted of an opaque Plexiglas disc 75 cm in diameter, elevated 58 cm above the floor by a tripod. Twenty holes, 5 cm in diameter, were located 5 cm from the perimeter, and a black Plexiglas escape box (19×8×7 cm) was placed under one of the holes. Distinct spatial cues were located all around the maze and kept constant throughout the study. On the first day of testing, a training session was performed, which consisted of placing the mouse in the escape box and leaving it there for 1 min. One minute later, the first session was started. At the beginning of each session, the mouse was placed in the middle of the maze in a 10-cm high cylindrical black start chamber. After 10 s, the start chamber was removed, a buzzer (80 dB) and a light (400 lux) were turned on, and the mouse was set free to explore the maze. The session ended when the mouse entered the escape tunnel or after 3 min had elapsed. When the mouse entered the escape tunnel, the buzzer was turned off and the mouse allowed to remain in the dark for one minute. When a mouse did not enter the tunnel by itself, it was gently put into the escape box for 1 min. The tunnel was always located underneath the same hole (stable within the spatial environment), which was randomly determined for each mouse. Mice were tested once a day for 12 d for the acquisition portion of the study. Note, in general, the Barnes maze is often preferred in mice over the Morris water maze because it is less stressful. However, since rodents were tested with NitroSynapsin for other indications using the Morris water maze, it was also used here for drug testing to afford comparison.

Morris Water Maze

We tested spatial reference learning and memory using a version of the conventional Morris water maze. The mice were trained to swim to a platform 14 cm in diameter and submerged 1.5 cm beneath the surface of the water. The platform was invisible to the mice while swimming. If a mouse failed to find the platform within 60 s, it was manually guided to the platform and allowed to remain there for 10 s. Mice were given 4 trials a day for as many days as necessary to reach the criterion (<20 s mean escape latency). Retention of spatial training was assessed 24 h after the last training trial. Both probe trials consisted of a 60-s free swim in the pool without the platform. The ANY-maze video tracking system (Stoelting Co.) was used to videotape all trials for automated analysis.

Three-Chamber Social Interaction

This test was originally developed by the Crawley group for an animal model of autism. Autistic individuals show aberrant reciprocal social interaction, including low levels of social approach and unusual modes of interaction. A social interaction apparatus consisting of a rectangular, three chambered Plexiglas box, with each chamber measuring 20 cm (length)×40.5 cm (width)×22 cm (height) was used. Walls dividing the chamber were clear with small semicircular openings (3.5 cm radius), allowing access into each chamber. The middle chamber was empty and the two outer chambers contained small, round wire cages (Galaxy Cup, Spectrum Diversified Designs, Inc., Streetsboro, OH). The mice were habituated to the entire apparatus for 5 min. To assess social interaction, mice were returned to the middle chamber, this time with a stranger mouse (C57BL/6J of the same sex tethered to the wire cage). Time spent in the chamber with the stranger mouse and time spent in the empty wire cage-containing chamber were each recorded for 5 min, as was the number of entries into each chamber. Experimental mice were tested once, and the stranger C57BL/6J mice were used for up to 6 tests.

Hole Board Exploration

The apparatus consisted of a Plexiglas cage (32×32×30 cm) with 16 holes in a format of 4×4 (each 3 cm in diameter) equally spaced on an elevated floor. The explorative activity including the number of head-dips and the time spent head-dipping were measured for 5 min.

Hippocampal Slice Preparation and Electrophysiology

One to six-month-old mice were anesthetized with isoflurane overdose and decapitated. The brain was rapidly dissected, and hippocampal slices (350 μm in thickness) were collected in ice-cold dissection buffer containing the following (in mM): 212 sucrose, 3 KCl, 5 $MgCl_2$, 0.5 $CaCl_2$, 1 $NaH_2PO_4$, 26 $NaHCO_3$, and 10 glucose (pH 7.4). The CA3 region was cut to avoid epileptiform activity. Slices were placed at 30° C. in artificial cerebrospinal fluid (ACSF) containing the following (in mM): 124 NaCl, 5 KCl, 26 $NaHCO_3$, 1.25 $NaH_2PO_4$, 2 $CaCl_2$, 1 $MgCl_2$, and 10 glucose (pH 7.4). ACSF and dissection buffer were bubbled with 95% $O_2$/5% $CO_2$. Before recordings, slices were placed in a submersion-recording chamber, maintained at 30° C., and perfused with ACSF for ≥1 h.

For extracellular field recordings, concentric, bipolar tungsten electrodes were used to activate Schaffer collateral/commissural (SC) fibers in the hippocampal CA1 region. Extracellular glass microelectrodes filled with ACSF (resistance~1-3 MΩ) were placed in the stratum radiatum to measure field excitatory post-synaptic potentials (fEPSPs). For baseline recordings, slices were stimulated at 0.033 Hz for 20 min at stimulation intensities of 30-40% of those used to elicit the largest measured fEPSP amplitude. Long-term potentiation (LTP) was induced by applying high-frequency stimulation (HFS) consisting of three 100 Hz pulses (Duration: 1 s, Interval: 20 s). Paired-pulse facilitation (PPF) was tested by applying two pulses with interstimulus intervals (ISIs) ranging from 20 to 200 ms. A Multiclamp 700B amplifier (Molecular Devices) was used for experiments. Data were sampled at 5 kHz and analyzed using the Clampfit 10 program (Molecular Devices).

Synaptic activity was recorded from dentate gyms (DG) granule neurons using the whole-cell voltage-clamp technique. Data were acquired using a Multiclamp 700B amplifier and Clampex 10.2 software (Molecular Devices). Recordings were sampled at 200 μs and filtered at 2 kHz. ACSF was used as the external bath solution, with 50 μM picrotoxin and 1 μM tetrodotoxin (TTX) to isolate spontaneous miniature excitatory postsynaptic currents (mEPSCs), or 10 μM 6-cyano-7-nitroquinoxaline-2,3-dione (CNQX), 50 μM (2R)-amino-5-phosphonopentanoate (AP5), and 1 μM TTX to isolate spontaneous miniature inhibitory postsynaptic currents (mIPSCs). All solutions were allowed to equilibrate for at least 20 min prior to initiating recording. The pipette internal solution for the voltage-clamp experiments contained the following (in mM): 120 K-gluconate, 15 KCl, 1 $MgCl_2$, 5 HEPES, 5 EGTA, 2 Mg-ATP, pH 7.4 (300 mOsm). mEPSCs and mIPSCs were typically recorded for at least 3-5 min and analyzed using the Mini Analysis Program version 6.0.3 (Synaptosoft).

Immunohistochemistry and Unbiased Stereological Cell Counting

Mice were perfused with PBS buffer and then 2% paraformaldehyde in PBS (PFA). After perfusion, brains were removed and placed into 2% PFA overnight for post-fixation and then sunk in 30% sucrose in PBS prior to freezing. Cryostat sections were cut at a thickness of 15 μm. Sections were soaked in Antigen Unmasking Solution (Vector) and microwaved for 30 s, followed by permeabilization with 0.25% Triton X-100 in PBS for 15 min. Primary antibodies were incubated for 16 h at 4° C. and fluorescence-conjugated secondary antibodies for 2 h at 25° C. Numerous unstained cells in each field served as an internal control for staining specificity. Primary antibodies included: NeuN (mouse, EMD Millipore), activated caspase-3 (rabbit, Cell Signaling), VGLUT1 (guinea pig, SYSY), VGLUT2 (rabbit, SYSY), VGAT (mouse, SYSY), synaptophysin (mouse, Sigma), GFAP (mouse, Sigma), PCNA (mouse, Santa Cruz), DCX (goat, Santa Cruz). TUNEL assay was performed to assess apoptosis using the Roche In Situ Cell Death Detection Kit per vender's instruction. The number of cells positive or percent area occupied by NeuN, activated caspase-3, TUNEL, GFAP, PCNA, or DCX was counted in specific brain regions using an optical dissector, or estimated by quantitative confocal immunohistochemistry or optical density, as described previously.

Preparation of Brain Lysates and Western Blotting

Brain tissue was homogenized in 10 volumes of cold sucrose buffer (0.32 M sucrose, 25 mM Hepes, pH 7.4). After a brief centrifugation at 3,000 g for 5 min at 4° C., the supernatant was collected and centrifuged at 10,000 g for 12 min at 4° C. The outer ¾ of the pellet was collected and re-suspended using the same sucrose buffer by gentle pipetting, while the dark center containing mitochondria was avoided. After a second centrifugation at 10,000 g for 12 min at 4° C., the pellet without a dark center was collected in cold FIBS (25 mM Hepes, pH 7.4, 150 mM NaCl) as the synaptosome-enriched brain lysate and used for western blot experiments. Primary antibodies for immunoblotting included: VGLUT1 (guinea pig, SYSY), VGLUT2 (Rabbit, SYSY), GAD65 (rabbit, Millipore), synaptophysin (mouse, Millipore), MEF2C (rabbit, Proteintech), α-tubulin (mouse, Sigma), β-actin (mouse, Sigma) and followed by appropriate secondary antibodies[52]. Note that GAD65 was used instead of VGAT for immunoblotting because the former antibody proved superior for western blots. The immunosignals were captured on Kodak x-ray film and quantified using Image J version 1.45 s.

Golgi Staining and Sholl Analysis

Standard Golgi-Cox impregnation was performed with WT and Mef2c-het brains using the FD Rapid GolgiStain kit (FD NeuroTechnologies, Inc.) according to the manufacturer's instructions. After a 3D montage of an entire cell was taken at 40× by deconvolution microscopy and reconstructed with SlideBook 5.0 software (Intelligent Imaging Innovations), Neurolucida neuron tracing software (MBF Bioscience) was used to delineate the whole cell profile and Sholl analysis was performed, as described in detail elsewhere. Cumulative dendritic intersections and dendritic lengths were analyzed.

Adult Neurogenesis

To study adult neurogenesis, 8-week-old mice were injected i.p. twice daily for 5 consecutive days with BrdU (50 mg/kg body weight) and perfused with 4% PFA 4 weeks after the last injection. Brains were then dissected and fixed overnight in 4% PFA, rinsed, cryoprotected, and frozen in liquid $N_2$. Cryosections (30 or 40 μm in thickness) were sliced on a cryostat. Standard immunostaining procedures were used for primary antibodies with appropriate conjugated secondary antibodies. For BrdU immunostaining, sections were pretreated in 2N HCL for 30 min. Cells positive for PCNA, DCX, BrdU, NeuN, or mCherry were analyzed in serial sections through the hippocampal DG of Mef2c-het and WT mice. Positive cells were counted under a 63× objective using SlideBook software. The total number of cells was counted using an optical dissector technique. Pictures were taken with the same exposure time and contrast/brightness parameters. The mean intensity for a particular marker was determined using ImageJ software and normalized to the average intensity of DG granule neurons. A minimum of 6 pictures containing at least 40 cells was analyzed for each marker.

Motor Behavioral Tests

Balance was measured by the latency to fall off the elevated (40 cm) horizontal rod (50 cm long) in four 20 sec trials. A flat wooden rod (9 mm wide) was used in trials 1-2 and a cylindrical aluminium rod (1 cm diameter) was used in trials 3-4. In each trial, the animals were placed in a marked central zone (10 cm) on the elevated rod. A score of 0 was given if the animal fell within 20 s, 1 if it stayed within the central zone for 20 s, 2 if it left the central zone, and 3 if it reached one of the ends of the bar. Traction capacity was measured over three 5 s trials as the ability of the animal to raise the hind limbs while remaining suspended by the forepaws grasped around an elevated horizontal bar (2 mm diameter). A score of 0 was given if the animal raised no limbs, 1 if it raised one limb, and 2 it raised the two limbs. Muscle Strength was determined by one trial of 60 s in which the mice were placed in the middle of the horizontal bar in an upside-down position and the latency until falling down was measured. For the vertical pole test, mice were placed with heads pointing upwards on a vertical wooden pole covered with cloth tape (1 cm diameter; height: 75 cm in trial 1, 55 cm trials 2-3). The latency to turn downward and the total time to descend to the floor over 3 trials was recorded. If the mouse did not turn downwards, dropped or slipped down, a default value of 60 s was recorded.

Microarray and NextBio Gene Network Analysis

Total RNA was extracted from frozen tissues prepared from the hippocampi of WT and Mef2c-het mice at postnatal day 30, using the Qiagen miRNA kit. RNA concentrations were determined using a Nanodrop spectrophotometer (Thermo Fisher Scientific), and RNA quality was assessed using an Agilent Bioanalyzer. All RNA samples included in the expression analysis had an RNA integrity number (RIN) >8. MouseRef-8 v2 expression beadchip (Illumina) was used for the gene-expression microarray. Microarray data analysis was performed using the R software and Bioconductor packages. Raw expression data were log2 transformed and normalized by quantile normalization. Data quality control criteria included high inter-array correlation (Pearson correlation coefficients>0.85) and detection of outlier arrays based on mean inter-array correlation and hierarchical clustering.

For pathway enrichment analysis, all genes whose expression was statistically altered ($P<0.05$) in Mef2c-het mice relative to WT mice were clustered for GO-terms using the pathway enrichment application of NextBio (Illumina, Inc.). The background set of genes used was the entire human genome. Rank scores were assigned by NextBio based on the method described previously. Genes clustered to GO-terms related to neuronal development were prioritized for validation of changes in gene expression.

Statistical Analysis

Data are reported as mean±s.e.m. Statistical tests in each experiment are listed here, in figure legends, or in the text. All data were analyzed using the Prism 6 program (GraphPad Software, Inc.). For data with a normal distribution, statistical significance was determined by Student's t test for pairwise comparisons. An ANOVA with Tukey's, Dunnett's, or Newman-Keuls post-hoc analysis was used for multiple comparisons. For categorical data, a Chi-square test or Fisher's exact test on a 2×2 contingency table was employed. For data not fitting a normal distribution, nonparametric tests were used. $P<0.05$ was considered statistically significant.

What is claimed is:

1. A method of treating a neurological condition caused by head trauma in a human subject in need thereof by administering to the subject NitroSynapsin:

Formula I

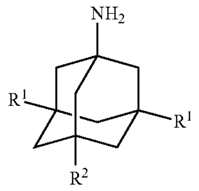

or a pharmaceutically acceptable salt thereof.

2. The method of claim 1, wherein the subject is a child.

* * * * *